(12) United States Patent
Leonard et al.

(10) Patent No.: US 12,064,562 B2
(45) Date of Patent: Aug. 20, 2024

(54) RESPIRATORY THERAPY UNIT WITH NON-CONTACT SENSING AND CONTROL

(71) Applicant: Vapotherm, Inc., Exeter, NH (US)

(72) Inventors: Scott A. Leonard, Bedford, NH (US); Jesse Bodwell, Exeter, NH (US); David Adams, Exeter, NH (US); David Winston, Exeter, NH (US); Marc Davidson, Exeter, NH (US); Joseph Jalbert, Woburn, MA (US); Nick Lauder, Woburn, MA (US)

(73) Assignee: VAPOTHERM, INC., Exeter, NH (US)

( * ) Notice: Subject to any disclaimer, the term of this patent is extended or adjusted under 35 U.S.C. 154(b) by 0 days.

(21) Appl. No.: 16/901,902

(22) Filed: Jun. 15, 2020

(65) Prior Publication Data

US 2021/0283357 A1 Sep. 16, 2021

Related U.S. Application Data

(60) Provisional application No. 62/988,583, filed on Mar. 12, 2020.

(51) Int. Cl.
*A61M 16/06* (2006.01)
*A61M 16/00* (2006.01)
(Continued)

(52) U.S. Cl.
CPC .... *A61M 16/0672* (2014.02); *A61M 16/0066* (2013.01); *A61M 16/1045* (2013.01);
(Continued)

(58) Field of Classification Search
CPC .......... A61M 16/0672; A61M 16/0666; A61M 16/0677; A61M 16/0066; A61M 16/20;
(Continued)

(56) References Cited

U.S. PATENT DOCUMENTS

| 2,414,747 A | 1/1947 | Kirschbaum |
|---|---|---|
| 2,742,040 A | 4/1956 | Moore |

(Continued)

FOREIGN PATENT DOCUMENTS

| CA | 2545570 | 9/2005 |
|---|---|---|
| CA | 2622734 A1 | 6/2007 |

(Continued)

OTHER PUBLICATIONS

International Search Report and Written Opinion for International Application No. PCT/US2007/021469 dated Oct. 13, 2008.
(Continued)

*Primary Examiner* — Tu A Vo
*Assistant Examiner* — Kelsey E Baller
(74) *Attorney, Agent, or Firm* — McDermott Will & Emery LLP

(57) ABSTRACT

The systems, devices, and methods described herein relate to providing breathing gas to a patient using a base unit and an auxiliary unit configured to be removably disposed on or at least partially in the base unit. The base unit has several couplings for improved control and sensing of the auxiliary unit and its components, wherein the couplings are configured to be non-contact with the corresponding components of the auxiliary unit and/or otherwise configured to minimize operational defects or improve efficiency. Non-contact couplings include induction heating, capacitive level sensing, a magnetically coupled rotor pump, RFID tag and reader, and Hall effect sensing. The breathing gas can be provided at high velocities by setting breathing gas flowrates based on dimensions of a nasal cannula used to direct the breathing gas into a patient's nares.

33 Claims, 18 Drawing Sheets

(51) Int. Cl.
*A61M 16/10* (2006.01)
*A61M 16/20* (2006.01)

(52) U.S. Cl.
CPC ..... *A61M 16/20* (2013.01); *A61M 2205/3334* (2013.01); *A61M 2205/583* (2013.01)

(58) Field of Classification Search
CPC ........ A61M 16/1045; A61M 2205/583; A61M 2205/3334; A61M 2205/3331; A61M 2205/502; A61M 2205/50; A61M 2205/505
USPC .................................................. 128/201.13
See application file for complete search history.

(56) References Cited

U.S. PATENT DOCUMENTS

| | | |
|---|---|---|
| 3,659,604 A | 5/1972 | Melville et al. |
| 3,734,091 A | 5/1973 | Taplin |
| 3,744,771 A | 7/1973 | Deaton |
| 3,871,373 A | 3/1975 | Jackson |
| 3,903,216 A | 9/1975 | Allan et al. |
| 3,923,057 A | 12/1975 | Chalon |
| 4,010,748 A | 3/1977 | Dobritz |
| 4,013,742 A | 3/1977 | Lang |
| 4,028,444 A | 6/1977 | Brown et al. |
| 4,028,445 A | 6/1977 | Hickmann et al. |
| 4,036,919 A | 7/1977 | Komendowski et al. |
| 4,051,205 A | 9/1977 | Grant |
| 4,098,853 A | 7/1978 | Brown et al. |
| 4,110,419 A | 8/1978 | Miller |
| 4,163,371 A | 8/1979 | Groninger |
| 4,172,105 A | 10/1979 | Miller et al. |
| 4,319,566 A | 3/1982 | Hayward et al. |
| 4,325,413 A | 4/1982 | Lenhart et al. |
| 4,354,984 A | 10/1982 | Richardson et al. |
| 4,366,105 A | 12/1982 | Nowacki |
| 4,369,777 A | 1/1983 | Lwoff et al. |
| 4,381,267 A | 4/1983 | Jackson |
| 4,430,994 A | 2/1984 | Clawson et al. |
| 4,463,755 A | 8/1984 | Suzuki |
| 4,500,480 A | 2/1985 | Cambio, Jr. |
| 4,532,088 A | 7/1985 | Miller |
| 4,584,996 A | 4/1986 | Blum |
| 4,589,409 A | 5/1986 | Chatburn et al. |
| 4,621,633 A | 11/1986 | Bowles et al. |
| 4,632,677 A | 12/1986 | Blackmer |
| 4,644,790 A | 2/1987 | Mizoguchi |
| 4,648,395 A | 3/1987 | Sato et al. |
| 4,652,408 A | 3/1987 | Montgomery |
| 4,657,713 A | 4/1987 | Miller |
| 4,665,911 A | 5/1987 | Williams et al. |
| 4,682,010 A | 7/1987 | Drapeau et al. |
| 4,753,758 A | 6/1988 | Miller |
| 4,765,327 A | 8/1988 | Shim |
| 4,765,340 A | 8/1988 | Sakai et al. |
| 4,810,854 A | 3/1989 | Jursich et al. |
| 4,838,258 A | 6/1989 | Dryden et al. |
| 4,889,116 A | 12/1989 | Taube |
| 4,910,384 A | 3/1990 | Silver |
| 4,921,642 A | 5/1990 | LaTorraca |
| 4,941,469 A | 7/1990 | Adahan |
| 4,943,704 A | 7/1990 | Rabenau et al. |
| 4,955,372 A | 9/1990 | Blackmer et al. |
| 4,957,107 A | 9/1990 | Sipin |
| 4,973,231 A | 11/1990 | Colliver |
| 5,003,985 A | 4/1991 | White et al. |
| 5,031,612 A | 7/1991 | Clementi |
| 5,036,847 A | 8/1991 | Boussignac et al. |
| 5,038,840 A | 8/1991 | Fair |
| 5,065,756 A | 11/1991 | Rapoport |
| 5,103,814 A | 4/1992 | Maher |
| 5,178,151 A | 1/1993 | Sackner |
| 5,255,674 A | 10/1993 | Oftedal et al. |
| 5,329,939 A | 7/1994 | Howe |
| 5,336,156 A | 8/1994 | Miller et al. |
| 5,349,946 A | 9/1994 | McComb |
| 5,367,604 A | 11/1994 | Murray |
| 5,388,575 A | 2/1995 | Taube |
| 5,392,770 A | 2/1995 | Clawson et al. |
| 5,431,885 A | 7/1995 | Zlotnik et al. |
| 5,437,634 A * | 8/1995 | Amano ............... A61M 1/3626 604/65 |
| 5,445,143 A | 8/1995 | Sims |
| 5,454,368 A | 10/1995 | Tarulli |
| 5,474,062 A | 12/1995 | DeVires et al. |
| 5,529,060 A | 6/1996 | Salmon et al. |
| 5,558,084 A | 9/1996 | Daniell et al. |
| 5,572,992 A | 11/1996 | Kankkunen et al. |
| 5,577,494 A | 11/1996 | Kuypers et al. |
| 5,588,423 A | 12/1996 | Smith |
| 5,623,922 A | 4/1997 | Smith |
| 5,724,957 A | 3/1998 | Rubsamen et al. |
| 5,752,498 A | 5/1998 | Lake et al. |
| 5,769,071 A | 6/1998 | Turnbull |
| 5,823,184 A | 10/1998 | Gross |
| 5,901,705 A | 5/1999 | Leagre |
| 6,010,118 A | 1/2000 | Milewicz |
| 6,041,777 A | 3/2000 | Faithfull et al. |
| 6,050,260 A | 4/2000 | Daniell et al. |
| 6,095,505 A | 8/2000 | Miller |
| 6,102,037 A | 8/2000 | Koch |
| 6,125,847 A | 10/2000 | Lin |
| 6,129,082 A | 10/2000 | Leagre |
| 6,142,971 A | 11/2000 | Daoud et al. |
| 6,152,132 A | 11/2000 | Psaros |
| 6,167,883 B1 | 1/2001 | Beran et al. |
| 6,186,142 B1 | 2/2001 | Schmidt et al. |
| 6,244,576 B1 | 6/2001 | Tsai |
| 6,256,454 B1 | 7/2001 | Dykes |
| 6,349,724 B1 | 2/2002 | Burton et al. |
| 6,367,472 B1 | 4/2002 | Koch |
| 6,397,841 B1 | 6/2002 | Kenyon et al. |
| 6,410,465 B1 | 6/2002 | Lim et al. |
| 6,454,997 B1 | 9/2002 | Divino, Jr. et al. |
| 6,510,848 B1 | 1/2003 | Gibertoni |
| 6,536,428 B1 | 3/2003 | Smith et al. |
| 6,550,476 B1 | 4/2003 | Ryder |
| 6,554,260 B1 | 4/2003 | Lipscombe et al. |
| 6,560,408 B2 | 5/2003 | Glucksman et al. |
| 6,561,187 B2 | 5/2003 | Schmidt et al. |
| 6,613,280 B2 | 9/2003 | Myrick et al. |
| 6,718,974 B1 | 4/2004 | Moberg |
| 6,769,430 B1 | 8/2004 | Carlsen et al. |
| 6,824,127 B2 | 11/2004 | Park et al. |
| 6,827,046 B2 | 12/2004 | Welle |
| 6,827,084 B2 | 12/2004 | Grubb, Jr. |
| 6,904,911 B2 | 6/2005 | Gibertoni |
| 6,912,977 B2 | 7/2005 | Cumming |
| 6,918,389 B2 | 7/2005 | Seakins et al. |
| 6,938,619 B1 | 9/2005 | Hickle |
| 6,938,886 B2 | 9/2005 | Glucksman |
| 6,953,354 B2 | 10/2005 | Edirisuriya et al. |
| 6,988,497 B2 | 1/2006 | Levine |
| 6,997,183 B2 | 2/2006 | Koch et al. |
| 7,051,733 B2 | 5/2006 | Gradon et al. |
| 7,066,452 B2 | 6/2006 | Rotering et al. |
| 7,073,500 B2 | 7/2006 | Kates |
| 7,077,135 B2 | 7/2006 | Pagan |
| 7,080,645 B2 | 7/2006 | Genger et al. |
| 7,081,560 B1 | 7/2006 | Lim et al. |
| 7,086,399 B2 | 8/2006 | Makinson et al. |
| 7,096,864 B1 | 8/2006 | Mayer et al. |
| 7,106,955 B2 | 9/2006 | Thudor et al. |
| 7,111,624 B2 | 9/2006 | Thudor et al. |
| 7,137,388 B2 | 11/2006 | Virr et al. |
| 7,140,367 B2 | 11/2006 | White et al. |
| 7,146,979 B2 | 12/2006 | Seakins et al. |
| 7,228,859 B2 | 6/2007 | Loescher |
| 7,250,035 B1 | 7/2007 | Ott et al. |
| 7,306,205 B2 | 12/2007 | Huddart et al. |
| 7,314,046 B2 | 1/2008 | Schroeder et al. |
| 7,329,038 B2 | 2/2008 | Hashiba |
| 7,380,774 B2 | 6/2008 | Akita et al. |

(56) References Cited

U.S. PATENT DOCUMENTS

| | | |
|---|---|---|
| 7,428,902 B2 | 9/2008 | Du et al. |
| 7,493,902 B2 | 2/2009 | White et al. |
| 7,571,725 B2 | 8/2009 | Wickham et al. |
| 7,802,571 B2 | 9/2010 | Tehrani |
| 7,849,852 B2 | 12/2010 | Bremner et al. |
| 8,194,944 B2 | 6/2012 | Tvig et al. |
| 8,240,306 B2 | 8/2012 | Cortez, Jr. et al. |
| D671,206 S | 11/2012 | McGarrity et al. |
| 8,322,339 B2 | 12/2012 | Gottlib et al. |
| 8,333,195 B2 | 12/2012 | Cortez, Jr. et al. |
| 8,356,593 B2 | 1/2013 | Cortez, Jr. et al. |
| 8,434,481 B2 | 5/2013 | Ogilvie et al. |
| 8,434,483 B2 | 5/2013 | Patel et al. |
| 8,434,484 B2 | 5/2013 | Patel et al. |
| 8,434,523 B2 | 5/2013 | Suhamo |
| 8,801,619 B2 | 8/2014 | Baker, Jr. et al. |
| 9,199,053 B1* | 12/2015 | Allum .................... A61B 5/682 |
| 10,007,238 B1 | 6/2018 | Taube |
| 10,864,346 B2 | 12/2020 | Harrington et al. |
| 2001/0035185 A1 | 11/2001 | Christopher |
| 2001/0050080 A1 | 12/2001 | Seakins et al. |
| 2001/0054422 A1 | 12/2001 | Smith et al. |
| 2001/0056258 A1 | 12/2001 | Evans |
| 2002/0000225 A1 | 1/2002 | Schuler et al. |
| 2002/0017302 A1 | 2/2002 | Fukunaga et al. |
| 2002/0055685 A1* | 5/2002 | Levitsky ............ A61M 16/0666 |
| | | 600/543 |
| 2002/0100320 A1* | 8/2002 | Smith ................ A61M 16/1095 |
| | | 73/431 |
| 2002/0148471 A1 | 10/2002 | Hirabayashi |
| 2002/0195104 A1 | 12/2002 | Fini et al. |
| 2003/0013980 A1 | 1/2003 | Starr et al. |
| 2003/0098022 A1 | 5/2003 | Nakao et al. |
| 2003/0211244 A1 | 11/2003 | Li et al. |
| 2003/0216285 A1 | 11/2003 | Dumont et al. |
| 2003/0236015 A1 | 12/2003 | Edirisuriya et al. |
| 2004/0016432 A1 | 1/2004 | Genger et al. |
| 2004/0050386 A1 | 3/2004 | Levine |
| 2004/0054261 A1 | 3/2004 | Kamataki et al. |
| 2004/0230108 A1 | 11/2004 | Melkeret et al. |
| 2004/0234254 A1 | 11/2004 | Czupich et al. |
| 2005/0022828 A1 | 2/2005 | Fukunaga et al. |
| 2005/0051168 A1 | 3/2005 | DeVries et al. |
| 2005/0109340 A1 | 5/2005 | Tehrani |
| 2005/0166915 A1 | 8/2005 | Gibertoni |
| 2005/0169615 A1 | 8/2005 | Glucksman |
| 2005/0178383 A1 | 8/2005 | Mackie et al. |
| 2005/0222503 A1 | 10/2005 | Dunlop et al. |
| 2005/0247311 A1 | 11/2005 | Vacchiano et al. |
| 2006/0021615 A1 | 2/2006 | Kertzman |
| 2006/0037613 A1 | 2/2006 | Kwok et al. |
| 2006/0113690 A1 | 6/2006 | Huddart et al. |
| 2006/0118111 A1 | 6/2006 | Pelerossi et al. |
| 2006/0130836 A1 | 6/2006 | Wixey et al. |
| 2006/0191531 A1 | 8/2006 | Mayer et al. |
| 2006/0213515 A1 | 9/2006 | Bremner et al. |
| 2006/0219243 A1 | 10/2006 | Walstrom |
| 2006/0243804 A1 | 11/2006 | Christoffersen et al. |
| 2006/0272639 A1 | 12/2006 | Makinson et al. |
| 2007/0137107 A1 | 6/2007 | Barnicki |
| 2007/0137646 A1 | 6/2007 | Weinstein et al. |
| 2007/0175473 A1* | 8/2007 | Lewis ................ A61M 16/085 |
| | | 128/204.18 |
| 2007/0283958 A1 | 12/2007 | Naghavi |
| 2008/0072899 A1 | 3/2008 | Niland et al. |
| 2008/0078386 A1 | 4/2008 | Feldhahn et al. |
| 2008/0078393 A1* | 4/2008 | Acker ................ A61B 5/097 |
| | | 128/204.29 |
| 2008/0135044 A1* | 6/2008 | Freitag ................ A61M 16/16 |
| | | 128/200.26 |
| 2008/0156328 A1 | 7/2008 | Taube |
| 2008/0183057 A1 | 7/2008 | Taube |
| 2009/0056712 A1 | 3/2009 | Cortez |
| 2009/0090363 A1 | 4/2009 | Niland et al. |
| 2009/0165795 A1* | 7/2009 | Nadjafizadeh ...... A61M 16/024 |
| | | 128/204.18 |
| 2009/0305214 A1 | 12/2009 | Pybus et al. |
| 2010/0059053 A1 | 3/2010 | Niland |
| 2010/0133292 A1 | 6/2010 | Ware et al. |
| 2010/0175695 A1 | 7/2010 | Jamison |
| 2010/0192957 A1* | 8/2010 | Hobson ............ A61M 16/0069 |
| | | 128/207.18 |
| 2010/0224191 A1 | 9/2010 | Dixon et al. |
| 2011/0144586 A1 | 6/2011 | Michaud |
| 2011/0152648 A1 | 6/2011 | Rustick |
| 2011/0190611 A1 | 8/2011 | Rabi |
| 2011/0200392 A1 | 8/2011 | Moncrief et al. |
| 2011/0214676 A1* | 9/2011 | Allum ............... A61M 16/0672 |
| | | 128/207.18 |
| 2011/0319783 A1 | 12/2011 | Lindholt et al. |
| 2012/0016219 A1 | 1/2012 | Fujii et al. |
| 2012/0090611 A1 | 4/2012 | Graboi et al. |
| 2012/0167880 A1* | 7/2012 | Jacob ................. A61M 16/024 |
| | | 128/203.14 |
| 2012/0325207 A1 | 12/2012 | Fromage |
| 2013/0030267 A1 | 1/2013 | Lisogurski et al. |
| 2013/0174841 A1 | 7/2013 | McAuley et al. |
| 2013/0263855 A1 | 10/2013 | Tivig |
| 2013/0276780 A1 | 10/2013 | Tobia et al. |
| 2014/0166005 A1 | 6/2014 | Tatkov et al. |
| 2014/0174442 A1 | 6/2014 | Cortez et al. |
| 2014/0311489 A1 | 10/2014 | Heine |
| 2015/0027204 A1 | 1/2015 | Stoks et al. |
| 2015/0048530 A1 | 2/2015 | Cheung et al. |
| 2015/0059754 A1 | 3/2015 | Chbat et al. |
| 2015/0107588 A1 | 4/2015 | Cheung et al. |
| 2015/0165142 A1* | 6/2015 | Tham ................ A61M 16/0816 |
| | | 128/202.22 |
| 2015/0297877 A1 | 10/2015 | Pelkus |
| 2015/0306335 A1* | 10/2015 | Winski ................. A61M 16/16 |
| | | 128/203.14 |
| 2015/0320953 A1 | 11/2015 | Acker et al. |
| 2016/0121063 A1 | 5/2016 | Tatkov et al. |
| 2016/0193438 A1 | 7/2016 | White et al. |
| 2016/0287832 A1 | 10/2016 | Cortez et al. |
| 2016/0361508 A1 | 12/2016 | Cohen |
| 2017/0143538 A1 | 5/2017 | Lee et al. |
| 2018/0078719 A1* | 3/2018 | Spence ................. A61M 16/16 |
| 2020/0170513 A1 | 6/2020 | Walkter |
| 2022/0265953 A1* | 8/2022 | Leonard ............... A61M 16/162 |

FOREIGN PATENT DOCUMENTS

| | | |
|---|---|---|
| CA | 2691377 | 1/2009 |
| CA | 2827253 | 9/2012 |
| DE | 2843756 A1 | 4/1980 |
| DE | 10317268 A1 | 11/2004 |
| EP | 1138340 A2 | 10/2001 |
| EP | 1586345 A1 | 10/2005 |
| EP | 3362489 | 8/2018 |
| GB | 1448473 A | 9/1976 |
| GB | 2252515 A | 8/1992 |
| WO | WO-198602276 A1 | 4/1986 |
| WO | WO-9624402 | 8/1996 |
| WO | WO-1999047197 A1 | 9/1999 |
| WO | WO-2002056931 | 7/2002 |
| WO | WO-2003035157 A1 | 5/2003 |
| WO | WO-2004096315 A2 | 11/2004 |
| WO | WO-2005038690 | 4/2005 |
| WO | WO-2005051280 | 6/2005 |
| WO | WO-2005097307 A1 | 10/2005 |
| WO | WO-2006024292 A1 | 3/2006 |
| WO | WO-2006026387 A1 | 3/2006 |
| WO | WO-2007038152 A1 | 4/2007 |
| WO | WO-2007101298 A1 * | 9/2007 ............ A61M 16/00 |
| WO | WO-2008030592 | 3/2008 |
| WO | WO-2012077052 | 6/2012 |
| WO | WO-2012080941 | 6/2012 |
| WO | WO-2015033288 A1 | 3/2015 |

(56) References Cited

FOREIGN PATENT DOCUMENTS

WO  WO-2016161092     10/2016
WO  WO-2018071812 A1 *  4/2018  .......... A61M 16/101

OTHER PUBLICATIONS

International Search Report for International Application No. PCT/US2008/008792 mailed on Dec. 18, 2008.
International Search Report for International Application No. PCT/US2016/025233 mailed on Jun. 9, 2016.
Partial International Search Report for International Application No. PCT/US2007/021469 dated Jul. 10, 2008.
Supplementary Partial European Search Report dated Jan. 27, 2015 for European Application No. EP08780252.6.
Vapotherm, "The New Standard in High Flow Therapy Brochure," 6 pages (2007).
Doshi et al., "The ventilatory effect of high velocity nasal insufflation compared to non-invasive positive-pressure ventilation in the treatment of hypercapneic respiratory failure: A subgroup analysis, " Heart & Lung, vol. 49: 610-615 (2020).
Möller et al., "Nasal High Flow Reduces Dead Space," Manuscript, Articles in PresS. J Appl Physio, pp. 1-25 (Nov. 17, 2016).
Ram et al., "Non-invasive positive pressure ventilation for treatment of respiratory failure due to exacerbations of chronic obstructive pulmonary disease (Review)," Cochrane Library, The Cochrane Collaboration, Cochrane Database of Systematic Reviews, pp. 1-58 (2010).
Vital et al., "Non-invasive positive pressure ventilation (CPAP or bilevel NPPV) for cardiogenic pulmonary oedema (Review)," Cochrane Library, The Cochrane Collaboration, Cochrane Database of Systematic Reviews, pp. 1-139 (2013).
https://my.clevelandclinic.org/health/disease/15283-acute-respiratory-distress-syndrome-ards6/20/2020.
https://lunginstitute.com/lung-disease/copd/copd-and-acute-respiratory-distress-syndrome/#:~:text=ARDS%20can%20be%20brought%20on.at%20high%20risk%20of%20ARDS (2020).
Qin, et al., "Mesenchymal stem cell therapy for acute respiratory distress syndrome: from basic to clinics". Protein Cell 2020 11(10): 707 (707-722).
Rawal et al. "Acute respiratory distress syndrome: An update and review." Journal of Translational Internal Medicine. Apr.-Jun. 2018, vol. 6, Issue 2. p. 74 (pp. 74-77).
Shafiee et al. "Coronavirus disease 2019: A tissue engineering and regenerative medicine perspective." Stem Cells Transl. Med. 2020:1-12.
Doshi et al., "High-Velocity Nasal in the Treatment of Respiratory Failure: A Randomized Clinical Trial", Annals of Emergency Medicine, 62(1):16 pages (2017).
Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).
International Search Report for International Application No. PCT/US2022/031170 mailed on Sep. 28, 2022.
Adawy, et al., "Design of Fuzzy Controller for Supplying Oxygen in Sub-acute Respiratory Illnesses", IJCSI, vol. 9, Issue 3, No. 1, May 2012 (15 pgs).
Alkurawy, "Design of an Efficient Controller for Arterial Oxygen Saturation in Neonatal Infants", PHD Thesis, University of Missouri—Columbia, Dec. 2013 (114 pgs).
Anon., "Analog Dialogue: Pulse Oximeter", Analog Devices, Inc., 1995-2014 (5 pgs).
Anon., "Critical Care Therapy and Respiratory Care Section", National Institutes of Health, 1112000.
Anon., "Oxygen Saturation", date unknown, downloaded Aug. 20, 2014 (4 pgs).
Anon.,"MR850 Respiratory Humidifier", Fisher & Paykel, REF 185042343, Rev. J, Aug. 2012 (3 pgs).
Ardizzoni, "The incredible versatile op amp in medical apps", Analog devices, Nov. 2, 2009 (3 pgs).
Branson, et al., "Is Humidification Always Necessary During Non-invasive Ventilation in the Hospital?", Respiratory Care, vol. 55, No. 2, Feb. 2010 (8 pgs).
Carter, et al., "Evaluation of heliox in children hospitalized with acute sever asthma. A randomized crossover trial", Abstract, Chest, 109(5):1256-61, May 1996.
Davies, et al., "Inspired Gas Temperature in Ventilated Neonates", Pediatric Pulmonology 38:50-54, 2004.
Elleau, et al., "Helium-Oxygen mixture in respiratory distress syndrome: a double blind study", J Pediatr., 122 1): 132-6, Abstract, Jan. 1993.
Head et al., ES 2267141, "Treatment of a hemoglobinopatia" (translation), Mar. 1, 2007, 18 pgs.
International Preliminary Report on Patentability for PCT Patent Application No. PCT/US2020/057823, dated May 10, 2022, 9 pages.
International Preliminary Report on Patentability for PCT Patent Application No. PCT/US2020/062118, dated May 17, 2022, 6 pages.
International Search Report and Written Opinion in International application No. PCT/US2020/057823 dated Jan. 28, 2021, 12 pages.
International Search Report and Written Opinion in International application No. PCT/US2020/062118 dated Mar. 11/2021, 7 pages.
Kass, et al., "Heliox therapy in acute severe asthma", Abstract, Chest, 107(3):757-60, Mar. 1995.
Kudukis, et al., "Inhaled helium-oxygen revisited: effect of inhaled helium-oxygen during the treatment of status asthmaticus in children", Abstract, J Pediatr., 130(2):217-24, Feb. 1997.
Lu, et al., "Helium-Oxygen in Treatment of Upper Airway Obstruction", Anesthesiology, vol. 45, Dec. 1976 (3pgs).
Manthous, et al., "Heliox improves pulsus paradoxus and peak expiratory flow in nonintubated patients with severe asthma", Am J Respir Grit Care Med. Abstract, 151(2pt 1):310-4, Feb. 1995.
Martin-Barbaz, et al., "Use of helium oxygen mixtures in status asthmaticus", Abstract, Rev Pneumol Clin. 43 4):186-9, 1987.
Panchal, et al., "Feedback-Controlled System to Titrate Oxygen Delivery", Drexel University, Winter 014 (41 pgs.
Sano, et al., Adaptive control of arterial oxygen pressure of newborn infants under incubator oxygen treatments, IEE Proceeding, vol. 132, Pt. D., No. 5, Sep. 1985 (7pgs).
Sauder, et al., "Helium-oxygen and conventional mechanical ventilation in the treatment of large airway obstruction and respiratory failure in an infant", Abstract, South Med J_84(5):646-8, May 1991.
Shiue, et al., "The use of helium-oxygen mixtures in the support of patients with status asthmaticus and respiratory acidosis", J Asthma, Abstract, 26(3):177-80, 1989.
Soto, et al., "Automatic Ventilation Control", Freescale.com/beyondbits, undated, downloaded Sep. 17, 2014 (3pgs).
Swidwa, et al., "Helium-oxygen breathing in severe chronic obstructive pulmonary disease", Abstract, Chest, 9=87 6): 790-5, Jun. 1985.
Wolfson, et al., "Mechanics and energetics of breathing helium in infants with bronchopulmonary dysplasia", Abstract, J Pediatr., 104(5):752-7, May 1984.

* cited by examiner

RESPIRATORY THERAPY UNIT WITH NON-CONTACT SENSING AND CONTROL

CROSS-REFERENCE TO RELATED APPLICATIONS

This application claims priority to and the benefit of U.S. Provisional Patent Application No. 62/988,583, filed on Mar. 12, 2020, and entitled "SYSTEMS AND METHODS FOR HIGH-VELOCITY RESPIRATORY THERAPY", the entire contents of the which is incorporated herein by reference.

BACKGROUND

Patients with respiratory ailments are often treated with respiratory assist devices that deliver supplemental breathing gas to the patient. Such devices may deliver gas to the patient using high flow therapy (HFT). HFT devices deliver breathing gas at a high flow rate via an interface such as a nasal cannula to increase the patient's fraction of inspired oxygen ($FiO_2$), decrease the patient's work of breathing, or do both. Increasing $FiO_2$ or decreasing the work of breathing helps the patient recover from respiratory ailments, such as respiratory distress or bronchospasms. Some HFT devices heat and humidify the delivered breathing gas for medical reasons (e.g., to maintain the pliability of the tissues of surfactant-deficient patients, or to preserve mucosal integrity) or to reduce patient discomfort.

Some HFT systems use membrane humidification to humidify the breathing gasses. The use of a membrane humidifier increases the pressure requirements of the system because membrane humidifiers resist the flow of air more than non-membrane humidifiers. Furthermore, some conventional HFT systems use nasal cannulas with small bore nasal prongs to increase the velocity of the breathing gasses entering a patient's airway. However, such cannulas further increase the required pressure compared to a system using large bore nasal prongs or a face mask. These increased pressure requirements of conventional HFT systems necessitate the use of wall air or a large compressor which limits the potential field of use of HFT.

Some respiratory therapy devices use a blower and a non-membrane humidifier to create humidified high flow therapy. Such non-membrane humidifiers are essentially heated water vessels through which gasses are channeled. These blower-based systems use larger bore cannulas to reduce pressure requirements. However, large bore cannulas do not flush $CO_2$ as effectively from a patient's airway as do small bore cannulas. Additionally, HFT devices typically include a display which shows the current flow rate of breathing gas but does not make other system parameters available to the user. Accordingly, the user is able to adjust the flow rate of the breathing gas, but cannot control other system parameters.

These respiratory therapy devices require the gasses to be heated and humidified prior to delivery to the patient to avoid drying the airway. Conventional humidifiers for breathing gas suffer from several drawbacks. The water that is used to humidify the gas must be heated. Traditionally this has required a resistive heater in a capital unit that is in contact with a conductive plate on the outside surface of an auxiliary unit that is also in contact with the water within the auxiliary unit. Either the heater in the capital unit or the heater plate on the auxiliary unit can be hot enough to injure a caregiver if the auxiliary unit is removed without sufficient time to cool. This configuration requires the heat to be generated in the capital unit and conducted to the water. By definition, the heater must be hotter than the desired water temperature and the heater may not only be heating the water. Conduction into the capital unit and convection with the surrounding air are both sources of heat loss to the environment. Proper function of this type of system also requires a good conduction path for the heat from the resistive heater to the heater plate and into the water. A good conduction path requires both plates to be very flat to achieve intimate contact. Any surface anomalies or surfaces that are not flat and pressed together with sufficient force will increase the temperature that the heater must reach to achieve the desired heat transfer rate. This also increases the heat loss of the system and danger to users and caregivers.

Humidifier systems require a reservoir of water that can fill the device as the water is consumed. In most devices, the flow of water is controlled by a float that allows water to enter when the device has depleted the water. These are prone to failure, which can let in too much water. Additionally, when the device is idle for long periods, the floats tend to leak water into the system. This water can end up in the gas passages and then be delivered to the patient through the patient interface when the device is started up, which can be uncomfortable or dangerous. The water chamber in the device must be vented to allow air out as water enters. The vent is typically a membrane material that allows air to pass while not allowing water to pass. A failure of the float can cause the membrane material to be submerged in water which over time will deteriorate the membrane and prevent air from escaping. This will eventually prevent water from entering the system and failure to humidify the gas or overheating of the machine or the gas.

These devices need to monitor the presence of water in the system. Running out of water can be dangerous to the patient or damage the device. Typically, a sensor that detects the position of a float provides this detection. Unfortunately, this usually only signals when the water is depleted, at which point the operator must immediately replenish the water supply to continue therapy.

In some devices, water from the water reservoir could get into the capital unit, particularly if the device is on standby for long periods while connected to a water source. In some cases, the user must clamp off the water source manually to avoid this occurring. Failure to do so may allow water to flood the humidification chamber and push water into the air path. Requiring the user to monitor and control the water in the system leads to increased risk of damage or misuse.

Conventional systems detect the presence of an auxiliary unit in the capital unit using sensors. Position switches and optical sensors are often used. In some cases, these may be adequate, but they provide only limited information about the auxiliary unit installed. Some devices may have different versions of an auxiliary unit that require the capital unit to know what auxiliary unit is installed so that the correct settings or functions can be enabled. Conventional systems rely on user input to ensure that the correct settings are implemented, but users can make mistakes or become confused. In some devices, the auxiliary unit must be fully seated to ensure correct function, but conventional systems do not have a way to detect if the device is slightly out of position.

Most conventional humidifiers have no way to actually measure the humidity delivered to the patient. Humidity measurement at near-saturated conditions is known to be very difficult and requires special sensors. Capacitive humidity sensors operate on the principal of hygroscopic materials absorbing moisture from the air, and are sometimes used in conventional systems. However, these sensors fail if they contact liquid water, which is common in humidifier flow paths. Chilled mirror systems, used in other conventional humidifiers, are bulky and not cost effective. They are also prone to false readings in the presence of liquid water.

It is advantageous to use a blower as a gas source for High Flow and High Velocity systems to eliminate dependence on wall air for operation. However, blowers have very little ability to generate pressure, so the flow resistance of the system must be considered. In particular High Velocity Nasal Insufflation (HVNI) systems, which utilize restrictive small bore cannulas to create a high velocity flow of gasses have high pressure requirements. This can preclude blower use. Because of this, all components of the air path must have minimal pressure drop so that as much of the blower's pressure as possible is reserved to accelerate the flow through the cannula prongs. A delivery tube is used to conduct the gasses from the capital unit to the patient. Many systems use a large diameter delivery tube with heated wire to reduce rainout. These are typically 15 or 22 mm in diameter. The flow velocity in these systems is very low, so the pressure drop is minimal. The low velocity flow in the delivery tube can allow condensation to accumulate in the delivery tube. This could be sent to the patient if the delivery tube is moved to allow the water to run downhill. Typically, however, the caregiver will simply empty the accumulated water periodically.

SUMMARY

Systems and methods for high velocity respiratory therapy are provided herein. The system includes a blower, a conduit, and a nasal cannula. The blower outputs breathing gas to the conduit which transmits a flow of breathing gas to the nasal cannula. The nasal cannula has at least one nasal prong which provides the breathing gas to a nare of a patient. The system is configured such that breathing gas exits the at least one nasal prong at a velocity of at least about 40 m/s and less than about 75 m/s. High flow and high velocity respiratory therapy, using the systems and methods provided herein, offers many advantages. Firstly, heated and humidified gas can be provided to a patient allowing for secretion clearance and decreased development of bronchial hyper-response symptoms and minmizing the impact of dry air on lung tissue. Another advantage is that the high-flow respiratory therapy systems and methods can better meet elevated peak inspiratory flow demands compared to conventional systems. These high flow systems and methods can increase functional residual capacity of a patient's lungs via delivery of positive end-expiratory pressure. High flow therapy via nasal cannula provides more comfort and is more tolerable to a patient relative to conventional systems. Oxygen dilution of the patient's upper airway can be minimized and carbon dioxide can be removed by meeting flow demands and flushing out dead space in the respiratory tract. The systems and methods herein may be configured to treat specific respiratory diseases and conditions such as viral diseases like COVID-19. Another advantage provided herein is portability of these systems by altogether eliminating the need for external sources of power and materials, providing an at-home or on-the-go device for continuity of care.

The systems, devices, and methods presented herein have a system architecture which permits the system to be operated by a lower pressure source (e.g., <270 hPa, <200 hPa, <150 hPa, <100 hPa, <50 hPa, <30 hPa, <20 hPa, <10 hPa, or any other suitable gauge pressure). By using a blower or similar low pressure source, the system does not require an external source of high pressure gas. Instead, the system can accept gas at ambient pressure and then pressurize the gas (e.g., internally). This allows the system to function in environments in which pressurized gas sources are not available (e.g., at home, in an ambulance, and/or an outpatient care center). In some implementations, the blower is a centrifugal blower. In some implementations, the nasal cannula includes two nasal prongs. In some implementations, the breathing gas is humidified within the system.

In some implementations, the at least one nasal prong has an inner diameter, and the system has a flowrate of breathing gas controlled by a maximum flow setpoint. In some implementations, the exit velocity of breathing gas from the nasal prong is a function of the inner diameter of the at least one nasal prong and the maximum flow setpoint. In order to achieve the desired exit velocity, there may be certain combinations of nasal prong inner diameter and maximum flow setpoint that are desirable. For example, the inner diameter may be greater than or equal to about 1.4 mm and less than about 1.8 mm, and the maximum flow setpoint is greater than or equal to about 9 L/min and less than about 28 L/min. For example, the inner diameter may be greater than or equal to about 1.8 mm and less than about 1.9 mm, and the maximum flow setpoint is greater than or equal to about 13 L/min and less than about 31 L/min. For example, the inner diameter may be greater than or equal to about 1.9 mm and less than about 3 mm, and the maximum flow setpoint is greater than or equal to about 21 L/min and less than about 60 L/min. For example, the inner diameter may be greater than or equal to about 3 mm and less than about 4 mm, and the maximum flow setpoint is greater than or equal to about 34 L/min and less than about 80 L/min.

In some implementations, the exit velocity is at least about 40 m/s and less than about 70 m/s. In some implementations, the exit velocity is at least about 40 m/s and less than about 65 m/s. In some implementations, the exit velocity is at least about 40 m/s and less than about 60 m/s. In some implementations, the exit velocity is at least about 40 m/s and less than about 55 m/s. In some implementations, the exit velocity is at least about 40 m/s and less than about 50 m/s. In some implementations, the exit velocity is at least about 40 m/s and less than about 55 m/s. In some implementations, the exit velocity is at least about 40 m/s and less than about 50 m/s. In some implementations, the exit velocity is at least about 40 m/s and less than about 45 m/s. In some implementations, the exit velocity is about 40 m/s.

In some implementations, the pressure drop of the cannula must be less than a certain threshold in order for the system to operate at certain flow rates. For example, if using a cannula with a nasal prong having an inner diameter greater than or equal to about 1.1 mm and less than about 1.6 mm, the pressure drop of the cannula must be less than 80 hPa when operating at a flow setpoint of 8 L/min. For example, if using a cannula with a nasal prong having an inner diameter greater than or equal to about 1.5 mm and less than about 2 mm, the pressure drop of the cannula must be less than 100 hPa when operating at a flow setpoint of 20 L/min. For example, if using a cannula with a nasal prong having an inner diameter greater than or equal to about 1.9 mm and less than about 3.5 mm, the pressure drop of the cannula must be less than 80 hPa when operating at a flow setpoint of 40 L/min.

According to one aspect, the system comprises a blower, a conduit, a nasal cannula having at least one nasal prong, a controller, and a processor. The blower is configured to output breathing gas to the conduit which transmits breathing gas to the nasal cannula. From the nasal cannula, the at least one nasal prong provides breathing gas to a nare of a patient. The system is configured such that breathing gas exits the at least one nasal prong at a velocity of at least about 40 m/s and less than about 75 m/s. The processor is configured to receive first data indicative of one or more dimensions of the nasal cannula, receive second data indicative of a flowrate of the breathing gas, and calculate the exit velocity based on the first data and the second data.

In some implementations, the system further comprises a display, and the processor is further configured to generate for display at least one of: the flowrate of breathing gas, the exit velocity, a maximum flow setpoint, and a pressure drop of the system. In some instances, both the exit velocity and the flowrate are displayed for the user (e.g., a physician or at-home patient). The user may view the display and decide to change one or more of the parameters. For example, the user may want to change the exit velocity. In some implementations, the system receives a user input indicating a change to at least one of the flowrate of breathing gas and the exit velocity. For example, a user input may indicate a modified flowrate, at which the user may wish to operate the system. For example, a user input may indicate a modified velocity, at which the user may wish to operate the system. In some implementations, after receiving a user input, the controller is configured to change the flowrate to account for the user input indicating a change to the flowrate or exit velocity. This step may require calculating a modified flowrate if the user input is a desired velocity, such that the modified flowrate corresponds to the desired velocity. In some implementations, the processor calculates a modified velocity based on the user input and the first data. For example, the user input may be a desired flowrate, and the processor calculates the modified velocity based on the dimensions of the at least one nasal prong and the desired flowrate.

In some implementations, the blower, controller, and processor are housed in a base unit. The system may comprise an auxiliary unit configured to reversibly connect to the base unit. In some implementations, the conduit is configured to reversibly connect to the auxiliary unit, such that the conduit is in fluid communication with the auxiliary unit which is in fluid communication with the blower when the auxiliary unit is connected to the base unit. The blower may provide the flow of breathing gas to the auxiliary unit while connected to the base unit, and the conduit may receive breathing gas from the auxiliary unit. The nasal cannula may be reversibly connected to the conduit to receive the breathing gas.

According to another aspect, a method for providing high velocity respiratory therapy utilizes the system of the first aspect. The method includes outputting a flow of breathing gas from a blower through a conduit and into a nasal cannula, and providing the breathing gas to a nare of the patient from at least one nasal prong of the nasal cannula. The nasal cannula is in fluid communication with the conduit and configured to receive the breathing gas from the conduit. The at least one nasal prong is configured to provide breathing gas from a distal end of the at least one nasal prong at an exit velocity of at least about 40 m/s and less than about 75 m/s.

In some implementations, the method further comprises receiving first data indicative of one or more dimensions of the nasal cannula, receiving second data indicative of a flowrate of breathing gas, and calculating the exit velocity based on the first data and the second data. In some implementations, the method further comprises generating for display at least one selected from the group of: the flowrate, the exit velocity, a maximum flow setpoint, and a pressure drop. In some implementations, both the flowrate and the exit velocity are displayed. The method may further involve receiving a user input to increase or decrease the flowrate of the breathing gas, changing the flowrate to a modified flowrate of the breathing gas, calculating a modified velocity based on the modified flowrate and the first data, and generating for display at least one selected from the group of: the modified flowrate and the modified velocity.

In another aspect, provided is a system for providing respiratory therapy to a patient, the system comprising a base unit comprising: a blower configured to output breathing gas and a controller; an auxiliary unit configured to be reversibly coupled to the base unit, wherein the auxiliary unit comprises an auxiliary unit outlet; and a delivery tube configured to receive the breathing gas from the auxiliary unit outlet and transmit the breathing gas to the patient. The base unit may further comprise a measurement device comprising a first flow sensor, a second flow sensor, and a device conduit in fluid communication with the blower, wherein the first flow sensor and second flow sensor are positioned in series along the conduit. The controller may be configured to set a breathing gas flowrate of the blower based on at least one of the first measurement or the second measurement. The system may comprise a supplementary gas inlet configured to receive a supplementary gas from an external gas source and add the supplementary gas to the breathing gas, wherein the supplementary gas inlet is in fluid communication with the device conduit and disposed between the first flow sensor and the second flow sensor. At least one advantage is that the dual sensor setup allows for detection of very small changes in flowrate, such that the amount of supplementary gas added can be finely tuned.

The base unit may comprise a seat configured to receive the auxiliary unit when the auxiliary unit is coupled to the base unit. The base unit may comprise at least one alignment sensor (e.g., an radio-frequency identification (RFID) reader or a Hall effect sensor), and the auxiliary unit comprises at least one alignment marker (e.g., an RFID or other tag, or a magnet). The system may include an occluding valve operatively configured to simultaneously control the outputted breathing gas and liquid flow entering the auxiliary unit, for example, using three valve positions. The auxiliary unit may comprise a liquid container and a vapor transfer cartridge (VTC) configured to humidify the breathing gas. The base unit may comprise a level sensor configured to output at least one liquid level measurement indicating a liquid level in the liquid container. The auxiliary unit may include a pump configured to pump the liquid in the auxiliary unit, where the pump may be magnetically coupled to the base unit. The auxiliary unit may comprise a heating plate in a heating section, and the base unit may comprise a heat actuator configured to couple to the heating plate in a non-contact manner. One or more temperature sensors may be disposed in the base unit to monitor liquid temperature or heating plate temperature. These various sensors and components allow for non-contact coupling between the auxiliary unit and the base unit. These non-contact couplings may minimize fluid contamination of the base unit or cross-contamination between the base unit and the auxiliary unit.

In some implementations, the delivery tube includes a jacket for insulating or heating the breathing gas conveyed within the delivery tube. The jacket may also be constructed to prevent kinking of the delivery tube. In some implementations, the base unit may comprise a removable battery and a reserve battery and may be configured to run on a low-power or standby mode when the removable battery is removed. One or more external devices may be coupled to the base unit; for example, a pulse oximeter or transcutaneous carbon dioxide sensor may be coupled to provide real-time oxygen or carbon dioxide measurements from a patient. Methods for closed-loop control of patient oxygen or carbon dioxide may be implemented on the system.

In another aspect, provided herein is a method of measuring breathing gas flow in a respiratory therapy device, the method comprising generating a first measurement of the breathing gas flow using a first flow sensor, generating a second measurement of the breathing gas flow using a second flow sensor, and adjusting one or more parameters of the respiratory therapy device based on at least one of the flow measurement or the second measurement. The method may further involve mixing the breathing gas flow with supplementary gas flow to form a mixed flow after measuring the first measurement. The method may further comprise pausing the flow of the supplementary gas; and calibrating the first flow sensor and the second flow sensor to each other while the supplementary gas flow is paused, wherein calibrating reduces an error of the calculated flow difference to an error of the second flow sensor. The method may further involve receiving $SpO_2$ data from a pulse oximeter; from the $SpO_2$ data, determining $PaO_2$ data; calculating an appropriate oxygen concentration of the breathing gas; effecting adaptive feedback control of the breathing gas based on the $SpO_2$ level signals, wherein the adaptive feedback control is provided by a proportional integral derivative (PID) controller; receiving a signal indicating that the breathing gas delivered by the measurement device has been manually changed; and upon receipt of the signal, entering a manual override mode and halting adaptive feedback control.

In another aspect, provided is a method for controlling operation of a respiratory therapy unit, the method comprising receiving a first signal from an alignment sensor in a base unit of the respiratory therapy unit, the first signal being indicative of an alignment the alignment sensor with an alignment marker of an auxiliary unit of the respiratory therapy unit; initiating operation of the respiratory therapy unit; receiving a second signal from the alignment sensor, the second signal being indicative of a misalignment of the alignment sensor with the alignment marker; and halting operation of the respiratory therapy unit.

In another aspect, provided is a method for controlling operation of a respiratory therapy unit, the method comprising receiving a temperature measurement from a temperature sensor in a heating section of the respiratory therapy unit; comparing the temperature measurement to a reference temperature; and if the temperature measurement is greater than the reference temperature, halting operation of the respiratory therapy unit.

In another aspect, provided is a method for controlling power in a respiratory therapy unit, the method comprising receiving a first signal indicating that a removable battery has been removed from the respiratory therapy unit; switching operation of the respiratory therapy unit from a regular power mode to a low power mode; and operating the respiratory therapy unit using a reserve battery in the respiratory therapy unit.

In another aspect, provided is a method for operating a respiratory therapy unit, the method comprising receiving at least one liquid level measurement from a level sensor, the at least one liquid level measurement indicating at least one liquid level in a liquid container of the respiratory therapy unit; receiving at least one flow measurement from a flow sensor, the at least one flow measurement indicating a flow rate of breathing gas in the respiratory therapy unit; and calculating a humidity of the breathing gas based on at least the at least one liquid level measurement and the at least one flow measurement.

In another aspect, provided is a measurement device for a respiratory therapy unit, the measurement device comprising a first flow sensor, a second flow sensor, and a conduit in fluid communication with the respiratory therapy unit, wherein the first flow sensor and second flow sensor are positioned in series along the conduit. The measurement device may further comprise a supplementary gas inlet configured to receive a supplementary gas from an external gas source and add the supplementary gas to the breathing gas, wherein the supplementary gas inlet is disposed between the first flow sensor and the second flow sensor.

In another aspect, provided is a respiratory therapy system comprising a base unit configured to output breathing gas; and an auxiliary unit configured to receive the outputted breathing gas, the auxiliary unit comprising a liquid container; and a vapor transfer cartridge (VTC) configured to humidify the breathing gas; wherein the liquid container comprises an outlet conduit in fluid communication with a cartridge inlet of the VTC. The base unit may comprise a level sensor configured to output at least one liquid level measurement indicating a liquid level in the liquid container. In some implementations, the system comprises a port configured to connect to a nebulizer from which aerosolized medicament is introduced into and becomes entrained in the breathing gas. For example, the port is located along a delivery tube of the system, on a nasal cannula or patient connector at the end of the delivery tube, or at the inlet or outlet of the VTC.

In some aspects, provided herein is a method of treatment of a respiratory disease or a viral disease. For example, the systems and methods described herein are used to treat coronavirus disease 2019 (COVID-19), caused by severe acute respiratory syndrome coronavirus 2 (SARS-CoV-2). These systems configured with a high flow nasal cannula may be used for mechanical ventilation of patients with respiratory failure (e.g., related to COVID-19). Treatment of COVID-19 may involve introducing supplementary oxygen into the breathing gas via a supplementary gas inlet. A pulse oximeter may be attached to the patient during treatment, such that $SpO_2$ is monitored and the flowrate of supplementary oxygen can be adjusted to provide enough oxygen to achieve a therapeutic level of oxygen in the patient.

In some aspects, provided herein is a mobile system for respiratory therapy. For example, a respiratory therapy system is disposed on a rolling cart, in a vehicle, or in a patient's home. The system may be configured to intake ambient air and pressurize by the blower, in addition to or in lieu of an external source of pressurized gas. The system may also be configured to operate on power from an internal battery, without an external power source.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
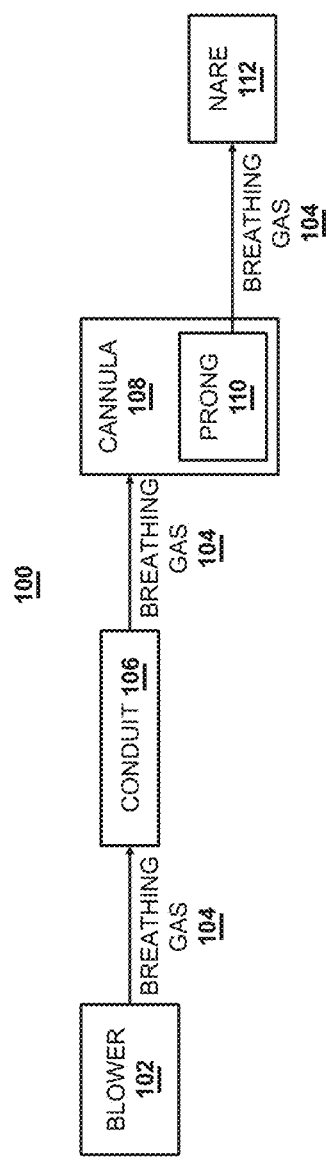
FIG. 1 shows a block diagram of a high-velocity respiratory therapy system, according to an illustrative implementation.

To provide an overall understanding of the assemblies and methods described herein, certain illustrative implementations will be described. Although the implementations and features described herein are specifically described for high velocity respiratory therapy, it will be understood that all the components and other features outlined below may be combined with one another in any suitable manner and may be adapted and applied to other respiratory therapy systems and devices, including low flow oxygen therapy, continuous positive airway pressure therapy (CPAP), mechanical ventilation, oxygen masks, Venturi masks, and Tracheostomy masks. The term "about," as used herein, should be understood to mean plus or minus 20%. For example, "about 40 m/s" should be understood to mean 40 m/s+8 m/s.

The systems, devices, and methods described herein may be used for High Flow Therapy (HFT). HFT systems/devices deliver breathing gas at a high flow rate via an interface such as a nasal cannula to increase the patient's fraction of inspired oxygen ($FiO_2$), decrease the patient's work of breathing, or do both. For example, HFT can create a reservoir with high $FiO_2$ in the nasal cavity, the nasopharynx, or the oropharynx. Increasing $FiO_2$ or decreasing the work of breathing helps the patient recover from respiratory ailments, such as respiratory distress or bronchospasms. Some HFT devices heat and humidify the delivered breathing gas for medical reasons (e.g., to maintain the pliability of the tissues of surfactant-deficient patients, or to preserve mucosal integrity) or to reduce patient discomfort (e.g., warmed and humidified nasal oxygen can be better tolerated). HFT may be used to eliminate anatomic dead space, for example, in a patient's upper airway. The high flow rate of gas maintains a constant flow of fresh gas into the patient's airway, the constant flow effectively washing out upper airway dead space. Patients experience assisted exhalation due to the flushing out of exhaled air by the constant flow of fresh gas, allowing a reservoir of fresh air to be readily inhaled. This flushing of the upper airway creates a reservoir that reduces room-air entrainment to such an amount that it becomes a true $FiO_2$ as set by the system/device, providing more effective oxygenation. Furthermore, humidification of the flow prevents negative effects of dry air on lung tissue from overcoming the ventilation effects of HFT.

As used herein, the term "processor" or "computing device" refers to one or more computers, microprocessors, logic devices, servers, or other devices configured with hardware, firmware, and software to carry out one or more of the computerized techniques described herein. Processors and processing devices may also include one or more memory devices for storing inputs, outputs, and data that is currently being processed. As used herein, "user interface" includes, without limitation, any suitable combination of one or more input devices (e.g., keypads, touch screens, trackballs, voice recognition systems, etc.) and/or one or more output devices (e.g., visual displays, speakers, tactile displays, printing devices, etc.). Examples of user devices that may implement an interface include, without limitation, personal computers, laptops, and mobile devices (such as smartphones, blackberries, PDAs, tablet computers, etc.). For example, an interface may be implemented over a web browser or a mobile application installed on the user device.

As used herein, the term "liquid" generally refers to water; however, "liquid" may also be inclusive of liquid drugs and mixtures of water and liquid drugs. As used herein, the term "breathing gas" generally refers to air; however, "breathing gas" may be used to refer to a gas having oxygen and/or carbon dioxide in proportions different from ambient air. "Breathing gas" may be used to refer to air, oxygen, carbon dioxide, helium, nitric oxide, gases containing vaporized water, gases containing an aerosol, and anesthetic gases. "Breathing gas" may be used to refer to gas mixtures such as mixtures of any of oxygen, carbon dioxide, nitrogen, helium, nitric oxide, gases containing vaporized water, gases containing an aerosol, and anesthetic gases.

System Parameters for High Velocity Respiratory Therapy

Several combinations of suitable system parameters for providing high-velocity respiratory therapy are discussed herein. As discussed above, the at least one nasal prong may have an inner diameter, and the system may have a flowrate of breathing gas controlled by a maximum flow setpoint. In some implementations, the exit velocity of breathing gas from the nasal prong is a function of the inner diameter of the at least one nasal prong and the maximum flow setpoint. In order to achieve the desired exit velocity, there may be certain combinations of nasal prong inner diameter and maximum flow setpoint that are desirable and/or allowable. Table 1 shows exemplary combinations of nasal prong inner diameter and maximum flow setpoint that achieve high velocity respiratory therapy.

TABLE 1

Exemplary combinations of nasal prong inner diameter and maximum flow setpoint configured to provide high velocity respiratory therapy on systems of the present disclosure.

| Nasal Prong Inner Diameter d (mm) | Maximum Flow Setpoint Q (L/min) |
| --- | --- |
| $1.4 \leq d < 1.8$ | $9 \leq Q < 20$ |
| $1.8 \leq d < 1.9$ | $13 \leq Q < 31$ |
| $1.9 \leq d < 3$ | $21 \leq Q < 60$ |
| $3 \leq d < 4$ | $34 \leq Q < 80$ |

In some implementations, there are certain cannula sizes that can be used on the high velocity respiratory therapy systems discussed herein due to certain system conditions or properties of the cannula. For example, there may be allowable cannula pressure drops for a given nasal prong inner diameter and flow setpoint. Table 2 shows exemplary ranges of cannula pressure drops for certain pressure drops and flow setpoints.

TABLE 2

Exemplary nasal cannula pressure drops that can allow high velocity respiratory therapy with the described system based on nasal prong inner diameter and flow setpoints.

| Nasal Prong Inner Diameter d (mm) | Cannula Pressure Drop (hPa) | Flow Setpoint (L/min) |
| --- | --- | --- |
| $1.1 \leq d < 1.6$ | 80 | 8 |
| $1.5 \leq d < 2$ | 100 | 20 |
| $1.9 \leq d < 3.5$ | 80 | 40 |

The parameters discussed above may be implemented on a respiratory therapy system, such as that shown in FIG. 1. FIG. 1 is a block diagram describing a system 100 for providing high-velocity respiratory therapy, according to an illustrative implementation. System 100 includes blower 102, conduit (also referred to as delivery tube herein) 106, and nasal cannula 108 having at least one nasal prong 110. Blower 102, delivery tube 106, cannula 108, and prong 110 are sequentially in fluid communication. Accordingly, breathing gas 104 is output from the blower 102, flows through delivery tube 106 to cannula 108, and exits cannula 108 through prong 110 into nare 112 of a patient.

Figure 2:
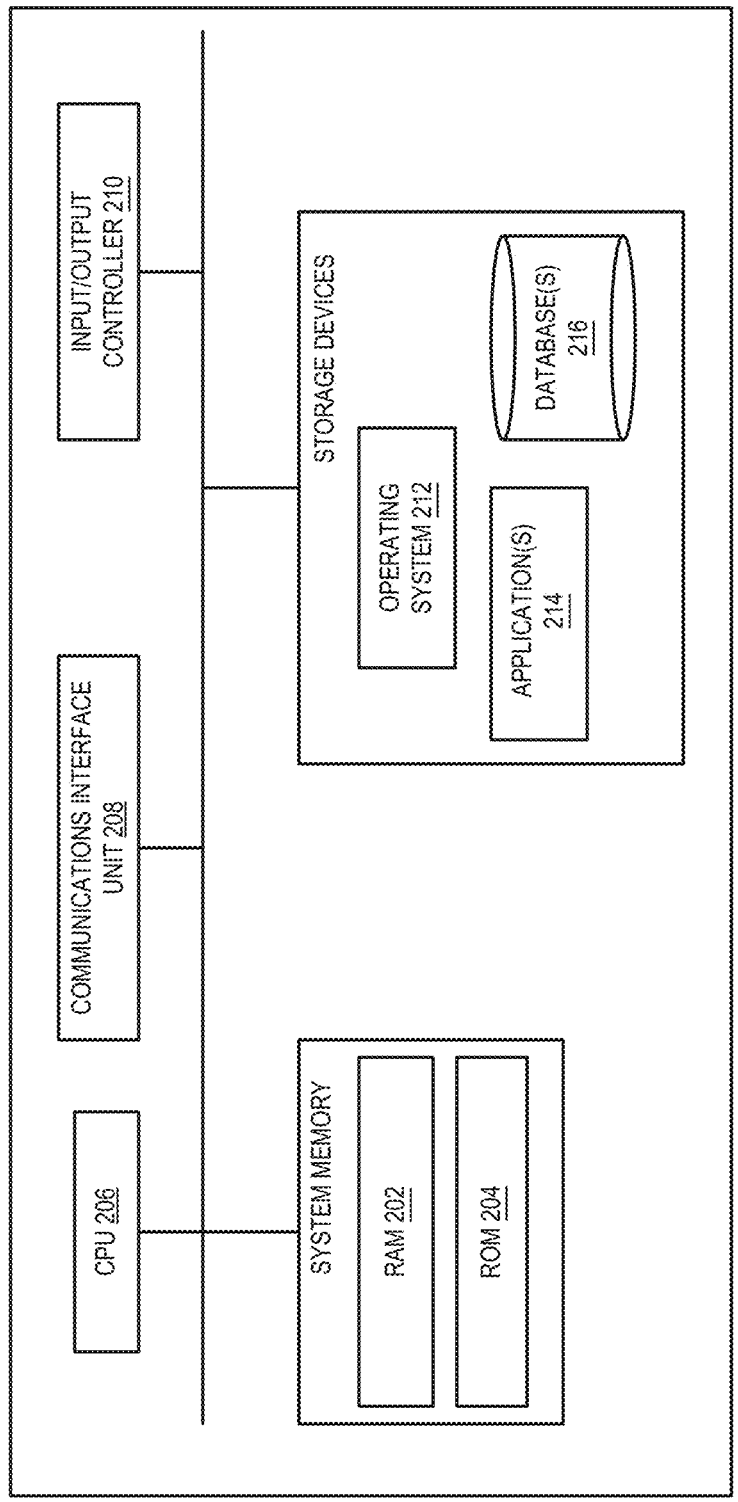
FIG. 2 shows a block diagram of a control system for a respiratory therapy system, according to an illustrative implementation.

In certain implementations, blower 102 is housed within a base unit, which may additionally include a computing device, such as computing device 200 of FIG. 2. This computing device may include a processor and/or a controller, for example, CPU 206 and input/output controller 210 of FIG. 2. In some implementations, delivery tube 106 does not directly attach to blower 102; rather, system 100 further comprises an auxiliary unit configured to reversibly connect delivery tube 106 to blower 102 or the base unit. Delivery tube 106 may reversibly connect at on end to the auxiliary unit, and cannula 108 may reversibly connect to an opposite end of delivery tube 106. Delivery tube 106 may be any suitable conduit for fluid transmission of air or breathing gas.

In some implementations, information or data about cannula 108 is received by system 100. The information or data may be received when cannula 108 is affixed to delivery tube 106 or when the auxiliary unit is connected to blower 102 or the base unit. For example, system 100 receives data indicative of dimensions of prong 110 of cannula 108. The cannula data may be stored in a chip located in the cannula 108 or in the auxiliary unit. In some implementations, system 100 comprises a transmitter configured to send the data to a receiver or the controller. The transmitter may be an RFID tag or other tag within the auxiliary unit or attached to the cannula 108. The tag may include information relating to the auxiliary unit, the nasal cannula, the at least one nasal prong, or any other relevant information. The base unit may include a receiver configured to receive the information from the tag.

In some implementations, the user provides the data. For example, the user may directly enter the data, upload the data from a separate device, or select an installed cannula from a list (e.g., a drop-down menu on a display), where the selected cannula is associated with certain data in the system. In some implementations, the cannula data may include additional information and may be used to identify the nasal cannula as originating from a specific manufacturer, having certain features, and/or having a use history. Knowing the cannula dimensions, such as an inner diameter of prong 110, may be useful for calculating the exit velocity of the breathing gas 104 from prong 110 into nare 112. Nasal cannula designs compatible with the present disclosure are described in U.S. Pat. No. 10,300,236, the contents of which are hereby incorporated by reference in their entirety.

For example, exit velocity may be calculated by the processor based on prong inner diameter and a measured flowrate of breathing gas 104. Breathing gas flowrate may be measured by one or more sensors in the system. The one or more sensors may be located within blower 102, at an outlet of blower 102, at an inlet or outlet of delivery tube 106, within delivery tube 106, within cannula 108, or at any other suitable location. The one or more sensors may send one or more measurements to the controller or processor. Data or measurements may be stored in a memory, such as memories 202 and 204 in FIG. 2, or in a database, such as database 216 in FIG. 2.

In some implementations, system 100 includes a display, which may be operated by the processor to, for example, display various system parameters or allow for user input. For example, the display may show any of the flowrate of breathing gas, exit velocity (e.g., the velocity calculated by the processor), humidity of the breathing gas, oxygen concentration, maximum flow setpoint, pressure drop, temperature, therapy duration, $FiO_2$, and/or battery level. This information can have utility to the user, such as a physician, who may evaluate the system parameters and make a decision to change one or more of the parameters. In some implementations, a user may input a change to any of the system parameters, for example, through the display as a touch-screen or an interface (e.g., interface 208 of FIG. 2). The processor may receive the user input, calculate changes to the one or more parameters, and direct the controller to change the system operating conditions accordingly. For example, the input may include a change from a first flowrate to a second flowrate, and the processor directs the controller to operate blower 102 at the second flowrate. The processor may then calculate a modified exit velocity based on cannula dimensions and the second flowrate. In some implementations, the user may choose an installed cannula from a drop-down list on the display as discussed above. Enabling the user to control the flow rate, the system can achieve effective flushing of the dead space in the patient's upper airway to provide better delivery of oxygen to the patient's lungs and provide an easier breathing experience. This effect is shown and described in relation to FIGS. 13A and 13B.

In some implementations, breathing gas 104 is humidified in system 100 before reaching nare 112. For example, the base unit or the auxiliary unit may comprise a vapor transfer cartridge configured to humidify or aerosolize water or medicament or a mixture thereof. Breathing gas 104 may be heated to reach a temperature optimal for humidification. A system which allows for controlling of a gas admixture with dew point and/or humidification management can be used to treat a wider range of patients. Furthermore, the system can be adapted with various gas mixtures and aerosolized medicaments to provide comfortable treatment of a patient. Alternative to a vapor transfer cartridge, in some implementations, a hot pot humidification chamber or evaporator is used to humidify the breathing gas, wherein the breathing gas is flowed over a reservoir of heated water that may be continuously or intermittently refilled. The water may be heated using an induction heating plate disposed in the reservoir, the plate generating heat due to a resistance against an current in the plate induced by a magnetic coil in the base unit.

FIG. 2 is a block diagram of a computing device, such as those described above in relation to FIG. 1, for performing any of the processes described herein, according to an illustrative implementation. Each of the components of these systems may be implemented on one or more computing devices 200. In certain aspects, a plurality of the components of these systems may be included within one computing device 200. In certain implementations, a component and a storage device may be implemented across several computing devices 200. Computing device 200 may be included in a base unit of a respiratory therapy unit, such as base units 402, 502, 602, 802, and 1002 (the computing device sometimes being referred to as a controller herein).

The computing device 200 includes at least one communications interface unit, an input/output controller 210, system memory, and one or more data storage devices. The system memory includes at least one random access memory (RAM 202) and at least one read-only memory (ROM 204). All of these elements are in communication with a central processing unit (CPU 206) to facilitate the operation of the computing device 200. The computing device 200 may be configured in many different ways. For example, the computing device 200 may be a conventional standalone computer or alternatively, the functions of computing device 200 may be distributed across multiple computer systems and architectures. In FIG. 200, the computing device 200 is linked, via network or local network, to other servers or systems.

The computing device 200 may be configured in a distributed architecture, wherein databases and processors are housed in separate units or locations. Some units perform primary processing functions and contain at a minimum a general controller or a processor and a system memory. In distributed architecture implementations, each of these units may be attached via the communications interface unit 208 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 206 includes a processor, such as one or more conventional microprocessors and one or more supplementary co-processors such as math co-processors for offloading workload from the CPU 206. The CPU 206 is in communication with the communications interface unit 208 and the input/output controller 210, through which the CPU 206 communicates with other devices such as other servers, user terminals, displays, or devices, such as the components of system 100 of FIG. 1. The communications interface unit 208 and the input/output controller 210 may include multiple communication channels for simultaneous communication with, for example, other processors, servers or client terminals.

The CPU 206 is also in communication with the data storage device. The data storage device may include an appropriate combination of magnetic, optical or semiconductor memory, and may include, for example, RAM 202, ROM 204, flash drive, an optical disc such as a compact disc or a hard disk or drive. The CPU 206 and the data storage device each may be, for example, located entirely within a single computer or other computing device; or connected to each other by a communication medium, such as a USB port, serial port cable, a coaxial cable, an Ethernet cable, a telephone line, a radio frequency transceiver or other similar wireless or wired medium or combination of the foregoing. For example, the CPU 206 may be connected to the data storage device via the communications interface unit 208. The CPU 206 may be configured to perform one or more particular processing functions.

The data storage device may store, for example, (i) an operating system 212 for the computing device 200; (11) one or more applications 214 (e.g., computer program code or a computer program product) adapted to direct the CPU 206 in accordance with the systems and methods described here, and particularly in accordance with the processes described in detail with regard to the CPU 206; or (iii) database(s) 216 adapted to store information that may be utilized to store information required by the program.

The operating system 212 and applications 214 may be stored, for example, in a compressed, an uncompiled and an encrypted format, and may include computer program code. The instructions of the program may be read into a main memory of the processor from a computer-readable medium other than the data storage device, such as from the ROM 204 or from the RAM 202. While execution of sequences of instructions in the program causes the CPU 206 to perform the process steps described herein, hard-wired circuitry may be used in place of, or in combination with, software instructions for implementation of the processes described herein. Thus, the systems and methods described are not limited to any specific combination of hardware and software.

Suitable computer program code may be provided for performing one or more functions described herein. The program also may include program elements such as an operating system 212, a database management system and "device drivers" that allow the processor to interface with computer peripheral devices (e.g., a video display, a keyboard, a computer mouse, etc.) via the input/output controller 210.

The term "computer-readable medium" as used herein refers to any non-transitory medium that provides or participates in providing instructions to the processor of the computing device 200 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 206 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 200 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

Figure 3:
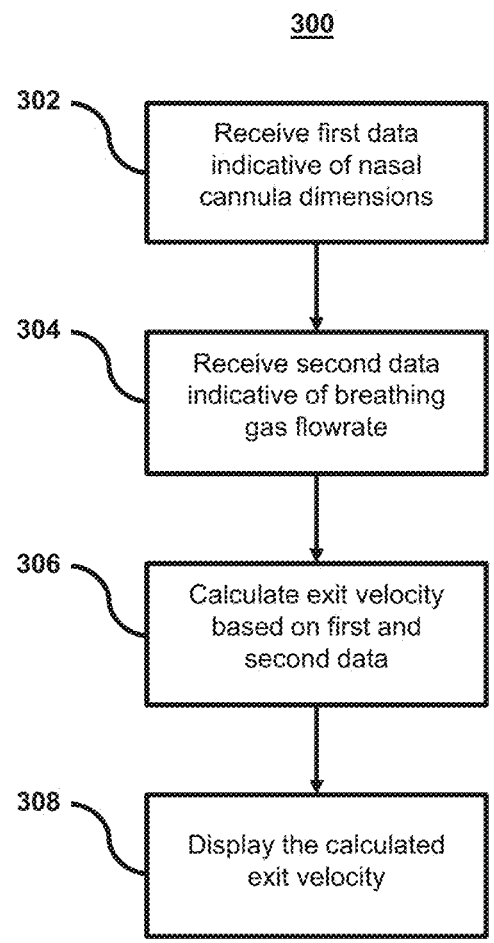
FIG. 3 shows a flowchart describing a method for calculating and displaying exit velocity of a respiratory therapy system, according to an illustrative implementation.

FIG. 3 is a flowchart of a process 300 for processing data relating to high velocity respiratory therapy, according to an illustrative implementation. Process 300 may be implemented on system 100 of FIG. 1, computing device 200 of FIG. 2, or any other suitable system or device. Step 302 involves receiving first data indicative of one or more nasal cannula dimensions. Step 304 involves receiving second data indicative of a breathing gas flowrate. For example, the first data and second data may be received by a processor, such as CPU 206. Step 306 involves calculating exit velocity of the breathing gas based on the first data and second data. Step 308 involves displaying the calculated exit velocity for a user.

The first data may include an inner diameter or cross-sectional area of one or more nasal prongs of a nasal cannula, such as nasal cannula 108 with prong 110. In some implementations, the first data is transmitted to a processor by a transmitter or by an RFID tag or other tag associated with the nasal cannula. In some implementations, the second data is indicative of one or more flowrate measurements taken by one or more sensors.

Process 300 may include additional steps. For example, a physician or other user may view the displayed velocity, other displayed parameters, or a patient's medical records/status and decide to change conditions of the therapy. In some implementations, process 300 further includes a step of receiving one or more user inputs. In some implementations, a user input is received indicating a desired change to at least one of the flowrate of breathing gas and the exit velocity. For example, a user input may indicate a modified flowrate, at which to operate the system or device. Alternatively or in addition, a user input may indicate a modified velocity. In some implementations, after receiving a user input, process 300 includes a step involving changing the flowrate to account for the user input indicating a change to the flowrate or exit velocity. The flowrate may be changed by a controller, such as input/output controller 210. This step may be followed by a step of calculating a modified flowrate if the user input is a desired velocity, such that the modified flowrate corresponds to the desired velocity. In some implementations, an additional step involves calculating a modified velocity based on the user input and the first data. For example, the user input may be a desired flowrate, and the processor calculates the modified velocity based on the dimensions of the at least one nasal prong and the desired flowrate.

In some implementations, steps 304 and 306 are altered such that the second data is indicative of the exit velocity, and the flowrate of breathing gas is calculated based on the first data and second data. In some implementations, step 306 calculates additional system parameters based on additional data. For example, the additional system parameters or additional data may include humidity of the breathing gas, oxygen concentration, maximum flow setpoint, pressure drop, temperature, therapy duration, FiO2, and/or battery level. Any of these system parameters/data may be displayed in step 308.

System Design and Architecture

A respiratory therapy unit configured for providing high velocity breathing gas to a patient can include features to improve water management, heating, humidification sensing and automation, among others, resulting in increased patient comfort and safety as well as improved treatment capability. FIGS. 4-10 depict examples of such respiratory therapy units and components thereof. While these units and components are depicted separately, it is to be understood that the units and/or components may be implemented in any combination and subcombination. It may be desirable to combine certain units and/or components in order to establish interoperability between the certain units and/or components which may lead to additional advantages or technical effects beyond those provided by each individual unit or component.

Figure 4:
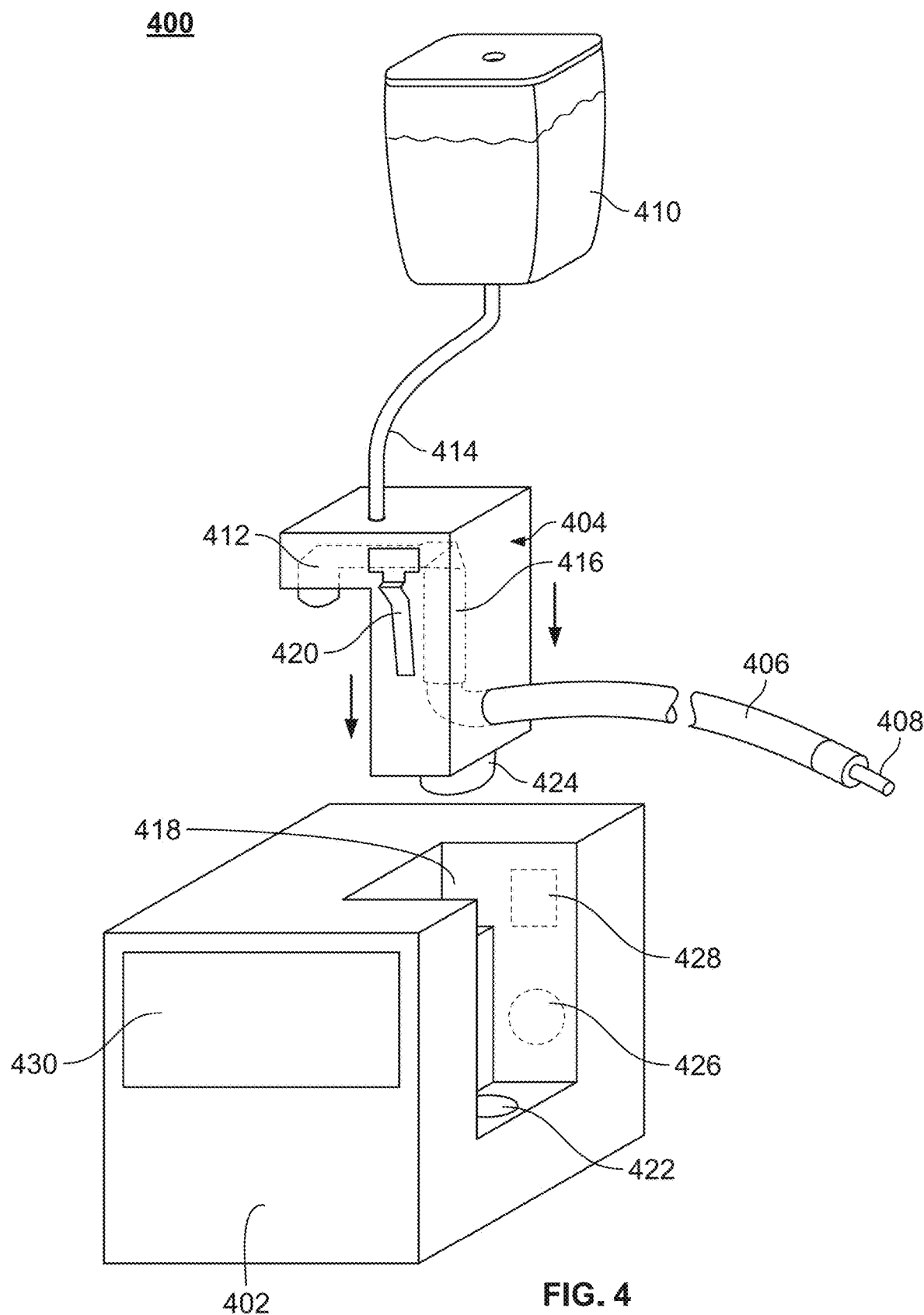
FIG. 4 shows a respiratory therapy system including a base unit and an auxiliary unit, according to an illustrative implementation.

FIG. 4 depicts a respiratory therapy system 400 for providing breathing gas to a patient, according to an illustrative implementation. System 400 comprises a base unit 402, an auxiliary unit 404, and a delivery tube 406. Base unit 402 contains a controller (not shown), and base unit 402 is configured to direct a flow of breathing gas into auxiliary unit 404 when auxiliary unit 404 is operatively coupled to base unit 402. Auxiliary unit 404 directs the breathing gas through gas path 412 to vapor transfer cartridge (VTC) 416 disposed within auxiliary unit 404. Auxiliary unit 404 is configured to receive a liquid (e.g., water) from external reservoir 410 through external liquid tube 414. Breathing gas flows from an outlet of VTC 416 into delivery tube 406 for delivery of the breathing gas to the patient. Delivery tube 406 includes a patient connector 408. For the operative coupling of auxiliary unit 404 to base unit 402, base unit 402 includes a recess 418 sized to receive auxiliary unit 404, and auxiliary unit 404 includes a latch 420 for locking auxiliary unit 404 in recess 418. Auxiliary unit 404 includes a pump 424 configured to pump the liquid. Base unit 402 includes various couplings 422, 426, and 428 that are configured to interact with auxiliary unit 404 or components thereof. A display 430 is included on base unit 402.

Base unit 402 may contain a blower configured to produce a flow of breathing gas. In the following, system 400 is described using a blower as an example; however, it is to be understood that base unit 402 (and the other base units described herein) may alternatively be connected to an external gas source such as a wall air outlet, an air tank, or an external blower. Furthermore, a VTC 416 is implemented in system 400; however, it is to be understood that alternatives may be implemented in system 400 (and the other systems described herein), such as a heated wire or hot pot humidifier. The alternatives may operate by disposing water over a heating plate in a chamber and flowing breathing gas into the chamber (either over the water or through the water) to be humidified. A heated wire can be disposed in a conduit to further heat the humidified breathing gas before delivering the breathing gas to a patient.

System 400 may further include a nasal cannula (not shown) coupled to patient connector 408. Alternatively, patient connector 408 may be a nasal cannula or other gas delivery device. In either case, system 400 may be operated with the previously discussed system parameters for high velocity respiratory therapy (i.e., the parameters in Tables 1 and 2). The nasal cannula or patient connector may be sized accordingly, and/or the blower may be operated at certain breathing gas flowrates. By using a blower, system 400 may absolve a need for an external source of pressurized air or breathing gas such as a pressurized tank or a wall air outlet. The controller of base unit 402 may be the computing device 200 of FIG. 2.

In some implementations, external reservoir 410 is a large container (>1 L, >2 L, >5 L, etc.) such as a bag or bottle, and the connecting tube 414 can be removably connected to auxiliary unit 404. Auxiliary unit 404 may be configured such that the liquid is fully enclosed in auxiliary unit 404 flowing from external reservoir 410. In this case, liquid is kept separate from base unit 402. This may prevent leaks and damage of components within base unit 402. In some implementations, gas path 412 is connected to the blower of base unit 402, but there is no other fluid communication between base unit 402 and auxiliary unit 404. Gas path 412 may be connected to base unit 402 by a valve, such as the occluder valves 652, 752, and 852 of FIGS. 6, 7D, 8A, and 8B. Such valve may be used to control the flow rate of breathing gas entering gas path 412 of auxiliary unit 404. The valve may also interact with liquid flow to simultaneously control breathing gas flowrate and liquid flowrate. The valve may comprise components that are separately attached to base unit 402 and auxiliary unit 404, such that the valve is operable when auxiliary unit 404 is fully seated in recess 418 of base unit 402, and the controller of base unit 402 actuates the valve. A gas seal, such as gas seals 660, 760, and 860 of FIGS. 6, 7A, 7B, 7D, 8A, and 8B, may be attached to auxiliary unit 404, in order to prevent gas leaks out of system 400 and to prevent liquid ingress into base unit 402 during operation. The gas seal may be a flexible portion that surrounds the valve, and the flexible portion is compressed to form a seal when auxiliary unit 404 is fully seated in recess 418 of base unit 402. The flexible portion of the gas seal, throughout this disclosure, may be a film, a gasket, a ring, or a collar, or other suitable mechanism.

While base unit 402 and auxiliary unit 404 are fluidically connected to at least allow breathing gas flow, it can be advantageous to otherwise minimize fluidic connections or contact between base unit 402 and auxiliary unit 404. For example, minimizing fluidic contact with base unit 402 may prevent damage to electronic components. As another example, previous systems have relied on conductive heating of liquid, which requires precise contact between two plates; thus, conductive heating is inefficient if precise contact cannot be established due to misalignment or deformation. Accordingly, couplings 422, 426, and 428 are configured to be contactless or non-contact couplings. Generally, this allows a sealed auxiliary unit without any openings and minimal requirements for tight tolerances. In some implementations, coupling 422 is a stator configured to magnetically couple to pump 424 which includes a rotor. Pump 424 may be shaped like a cup with a convex side protruding from auxiliary unit 404, and the stator may surround a cavity in recess 418, such that pump 424 sits within the cavity when auxiliary unit 404 is seated in recess 418. Pump 424 and coupling 422 may each be hermetically sealed, for example, to prevent fluid ingress into base unit 402. When auxiliary unit 404 is fully seated in base unit 402, the controller can operate the stator to magnetically generate rotation of the rotor of pump 424 to pump liquid through the auxiliary unit or through a jacket of delivery tube 406. As a result, the auxiliary unit 404 pumps liquid without an internalized power source or other electronic components to control the pump 424, and there is no need for liquid to flow through the base unit 402 which separately houses the controller and other components that may be susceptible to, e.g., water damage. Pump designs compatible with the present disclosure are described in U.S. patent application Ser. No. 15/783,566, the contents of which are hereby incorporated by reference in their entirety.

Figure 5:
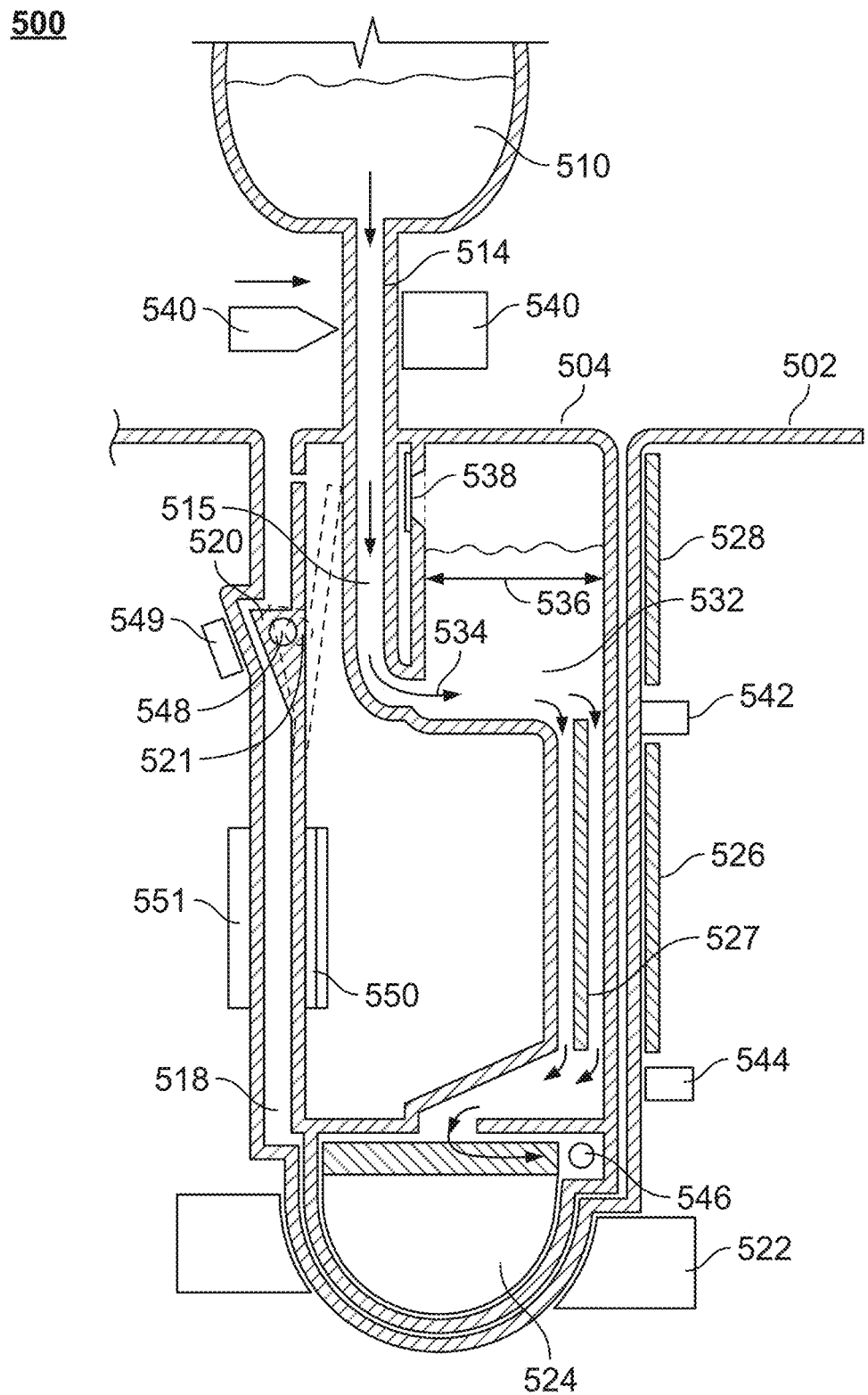
FIG. 5 shows a cross-section of a respiratory therapy system including an auxiliary unit seated in a base unit, according to an illustrative implementation.

Similarly, coupling 426 may be a contactless or non-contact heating actuator, for example, heat actuator 526 of FIG. 5, used to convey energy to auxiliary unit 404 to heat the liquid. In some implementations, coupling 426 is a coil configured to heat a plate disposed in auxiliary unit 404. The plate may be, for example, the heating plates 527, 727, or 927 of FIGS. 5, 7C, 7F, and 9. The coil may heat the plate via induction. This may involve the coil inducing a current in the plate that is circular in shape and immersed in liquid in auxiliary unit 404. The induced current generates heat in the plate due to a resistance of the plate. Because the heat is generated in the plate that is surrounded by liquid, external surfaces of auxiliary unit 404 and base unit 402 that can be touched by a user/operator never exceed the liquid temperature. This configuration eliminates the need for precisely manufactured flat plates to get intimate contact between a heat source in base unit 402 and a conductive plate in auxiliary unit 404. Inductive heating improves efficiency of heating, because the generated heat is isolated to auxiliary unit 404 and does not heat the base unit 402. If base unit 402 were heated by excess heat, additional cooling would be required to remove the heat; however, additional cooling is unnecessary with the present inductive heating configuration. Improved efficiency also allows longer operation of system 400 if power is supplied by a battery (not shown) in situations where wall power is not available, e.g., during mobile use or power outages.

Heated liquid may be used to heat, in turn, breathing gas. For example, delivery tube 406 may include a jacket configured to receive heated liquid and convey the heated liquid around an inner lumen that conveys the breathing gas. Heated liquid may travel along a full length of delivery tube 406 in a first direction towards patient connector 408, and then return in an opposite direction back to auxiliary unit 404. Heated liquid may also be conveyed into VTC 416 and vaporized into the breathing gas. For example, the liquid may be water used to humidify the breathing gas. Accordingly, the liquid may be heated to a target temperature, where the target temperature is a temperature at which the gas is to be delivered to the patient. The liquid may be circulated through auxiliary unit 404 and delivery tube 406 and back to the internal reservoir. In some implementations, the liquid travels a liquid path from the external reservoir to the internal reservoir (internal to auxiliary unit 404), then to a heating section (e.g., where the heating plate may be disposed), then through pump 424, then into the heating jacket of delivery tube 406, then into VTC 416, and then any remaining, un-vaporized liquid is returned to the internal reservoir. A similar configuration is described in further detail in relation to FIG. 5.

Similar to coupling 426, coupling 428 may be a contact-less or non-contact level sensor, for example, level sensor 528 of FIG. 5, configured to detect a liquid level in auxiliary unit 404. For example, auxiliary unit 404 may contain an internal reservoir, such as the one described above and internal reservoirs 532, 732, and 932 of FIGS. 5, 7C, 7D, 7F, and 9. Liquid is stored in the internal reservoir for use, e.g., in VTC 416 and/or heating jacket of delivery tube 406. When the liquid is water that is vaporized into the breathing gas within VTC 416, it may desirable for the system or user to know the humidity of breathing gas provided to the patient. In some implementations, the internal reservoir has a constant diameter or cross-section (for example, cross-section 536 of internal reservoir 532 of FIG. 5), so that the volume of liquid is linearly proportional to the liquid level in the reservoir. In this implementation, level sensor 428 is configured to measure the liquid level when auxiliary unit 404 is fully seated in base unit 402. Level sensor 428 may be a capacitive sensing circuit positioned alongside the internal reservoir. In this implementation, the liquid level may be measured, because the capacitance of the liquid changes as the liquid level changes. Capacitive sensing provides a non-contact means for detecting the liquid level.

Level sensor 428 may output one or more signals indicating the measured liquid level to the controller in base unit 402. The occluder valve or a pinch valve disposed along tube 414 can be used to isolate the volume of liquid in auxiliary unit 404. In implementations where liquid only leaves system 400 when vaporized into the breathing gas in VTC 416, the controller can determine the amount of liquid vaporized (i.e., the vaporization rate) or otherwise consumed (i.e., consumption rate) over time. In some implementations, this information is used to determine the flowrate of liquid needed from external reservoir 410 in order to keep the liquid level at a steady state, where the liquid flowrate from external reservoir 410 equals the vaporization rate, in order to, for example, prevent auxiliary unit 404 and VTC 416 from drying up or ensure the breathing gas is kept at a constant vapor concentration (e.g., humidity). In other implementations, the liquid level is not at a steady state, but the controller determines, based on the vaporization flowrate, an appropriate time interval at which to allow a fixed volume of the liquid to enter the internal reservoir from external reservoir 410 that is approximately equal to the amount of liquid vaporized during that time interval.

From the calculated vaporization rate, the controller may also compute the humidity of the breathing gas exiting VTC 416 in implementations where the liquid is water. Another device, such as measurement device 1086 of FIG. 10, may be used to determine the flowrate (mass flowrate and/or volumetric flowrate) of breathing gas in system 400. Such a device may be disposed in base unit 402 to measure breathing gas entering or exiting the blower, or the device may be disposed in auxiliary unit 404 to measure breathing gas flowrate entering or exiting auxiliary unit 404 or VTC 416. The device may alternatively be disposed along or within delivery tube 406 or patient connector 408 for a patient-proximate measurement of the breathing gas flowrate. In any of these cases, the device outputs one or more signals indicating the breathing gas flowrate to the controller. Also knowing the consumption rate or vaporization rate, the controller can calculate the humidity of breathing gas based on the liquid consumption/vaporization rate and the breathing gas flowrate, because liquid in the closed auxiliary unit 404 may only exit system 400 as vapor in the breathing gas when liquid flow from external reservoir 410 is stopped.

Knowing the humidity can serve several purposes. For example, an inappropriately low or high humidity may indicate that auxiliary unit 404, VTC 416, or another component of system 400 has become defective and requires replacement, allowing the controller to halt operation of system 400 and notify the operator before the patient is harmed. As another example, the performance of system 400 may be monitored over time, using humidity as a monitored variable, in order to detect deterioration and extend the usable lifetime of system 400. In this case, there is no need to limit all devices to the performance of outliers during lifetime testing. Also, knowing humidity, adjustment of a temperature within VTC 416 relative to a temperature within delivery tube 406 can allow for adjustment of the humidity if the humidity output is monitored for safety. In some implementations, system 400 stores (e.g., on a memory) a range of safe humidity levels for patient breathing gas, and the controller is configured to determine if the calculated humidity is within the safe range. If the calculated humidity falls outside of the safe range, the controller may adjust the power of pump 424 to adjust liquid flowrate and/or adjust the power of the blower to adjust breathing gas flowrate.

Latch 420 is configured to lock auxiliary unit 404 in recess 418 of base unit 402 when auxiliary unit 404 is correctly positioned/seated in recess 418 for proper operation of system 400 and interoperability between auxiliary unit 404 and base unit 402. A user may press against latch 420 to unlock auxiliary unit 404 and remove it from base unit 402. In order to ensure that auxiliary unit 404 is fully seated in recess 418 for proper operation, there may be one or more elements disposed in base unit 402 and auxiliary unit 404 configured to detect the presence, or the precise alignment of auxiliary unit 404 in recess 418. In some implementations, auxiliary unit 404 includes a RFID tag (e.g., RFID tag 550 of FIG. 5) or other tag, and base unit 402 includes an antenna or reader (e.g., RFID reader 551 of FIG. 5). The tag can be detected by the antenna or reader in a non-contact manner when the tag is positioned near the antenna or reader, essentially when auxiliary unit 404 is seated in recess 418.

Accordingly, the tag may also include information that can be read by the antenna or reader and transmitted to the controller or a memory of base unit 402. For example, the tag may include information describing the type of or feature in auxiliary unit 404, such as low flow, high flow, aerosolization, humidification, oxygenation, nitric oxide, helium, and/or closed loop oxygen control. The tag may also include information relating to the state of the specific auxiliary unit 404 and/or its various components. For example, the information may include use history (including the in-use date), a shelf-life or remaining lifetime, embedded licensing, and/or recommended operating parameters (limit flowrates or humidity). The controller may use any of the information described above to determine and execute appropriate adjustments to system 400 and any of its various components. For example, depending on the type or features of auxiliary unit 404, certain operations or features may be enabled or disabled by the controller in accordance with the in-use auxiliary unit 404.

RFID tags or other tags can provide additional information about an auxiliary unit such as the auxiliary unit type, when it was first used, the expiration date, etc. This can overcome the drawbacks of the above-mentioned systems. In some systems the device needs to be aware of a change in auxiliary unit even if the capital unit is in standby. To detect an auxiliary unit change in these systems RFID may require the device to use too much power while in standby. As an example, an active valve can close the air path when the auxiliary unit is removed and close the water fill path when an auxiliary unit is installed. Such features may not function correctly if the auxiliary unit is added or removed when the device is off or in a standby mode. This can occur if the auxiliary unit is set up in advance to be ready for a patient. The device is off when the auxiliary unit is installed and water may flow uncontrolled into the device. It would be beneficial for the device to power on and close the valve.

In some implementations, auxiliary unit 404 incudes one or more magnets (e.g., alignment marker 548 of FIG. 5), and base unit 402 includes a Hall effect sensor (e.g., alignment sensor 549 of FIG. 5) configured to sense the presence of the magnet in order to determine in a non-contact manner if auxiliary unit 404 is fully seated in recess 418. A Hall effect sensor measures a magnitude of a magnetic field and outputs a voltage proportional to the magnetic field magnitude. Accordingly, the Hall effect sensor may detect the magnetic field of the magnet when in close proximity. By using a magnet and Hall effect sensor, the precise position of auxiliary unit 404 may be detected, and a change in state may be detected even when system 400 is in a stand-by or low-power mode, because the Hall effect sensor may operate on a very low power when system 400 is in stand-by, and a change in this Hall effect sensor can be used to wake system 400 to, for example, read the RFID tag or start operation of certain components such as the blower or pump 424. As another example, the controller may be configured to close the occluder valve to block breathing gas flow from base unit 402 to auxiliary unit 404 when auxiliary unit 404 is removed, even if system 400 is in stand-by, to ensure that the gas path is not left open when the disposable is removed. The magnet may be configured to have a narrow range in which it can trigger the Hall effect sensor. The range may be less than about 5 mm, less than about 4 mm, less than about 3 mm, less than about 2 mm, or less than about 1 mm. In some implementations, the magnet is disposed within latch 420, so that the Hall effect sensor is triggered by the magnet when latch 420 is in the locked position. A barcode may be used in auxiliary unit 404 in addition to or in place of an RFID tag or other tag, such that a reader in base unit 402 reads the barcode when auxiliary unit 404 is docked in recess 418. The barcode may include the information about one or more components, as is described in relation to the RFID tag in this disclosure. As another option, base unit 402 includes an infrared (IR) proximity sensor having an IR beam positioned such that latch 420 breaks the beam, triggering the sensor, when auxiliary unit 404 is fully seated in recess 418. Other options for auxiliary unit presence sensing and data storage/transfer include quick response (QR) codes, global positioning system (GPS) chips, Bluetooth®, Bluetooth® low-energy, near-field communication (NFC), and pattern recognition matching.

System 400 may be configured to automatically switch to a stand-by or low-power mode under certain conditions. For example, system 400 may switch to stand-by mode when auxiliary unit 404 is not detected, when the blower is off and a user has not interacted with system 400 for a certain period of time, or when a user inputs a command to switch system 400 to the stand-by mode. When switching to stand-by or low-power mode, the controller may generate an alert to notify the user of the switch. System 400 may be configured to be powered by a standard wall outlet or a main battery. In either case, system 400 may include a reserve battery. The reserve battery may be a rechargeable battery, such as lithium-ion, lead-acid, nickel-cadmium, nickel-metal hydride, lithium-ion polymer, alkaline, or another equivalent. The reserve battery may be configured to provide power to system 400 when the wall outlet becomes unusable (e.g., during a power outage) or when the main battery requires replacement. In some implementations, system 400 can operate on solely the reserve battery for at least about 30 minutes, at least about 1 hour, at least about 2 hours, or at least about 5 hours. The stand-by or low-power mode may limit power usage of system 400 to a percentage of the maximum power usage of system 400 during normal operation (e.g., about 80%, about 70%, about 60%, about 50%, about 40%, about 30%, about 20%). In some implementations, the controller switches system 400 to the stand-by or low-power mode when the reserve battery is in use. When in stand-by or low-power mode, the controller may disable certain features, for example, to reduce power consumption. For example, the controller may disable heating elements or supplementary gas input, allowing operation of the blower and one or more alarms (e.g., auditory alarms, notifications on display 430).

Figure 9:
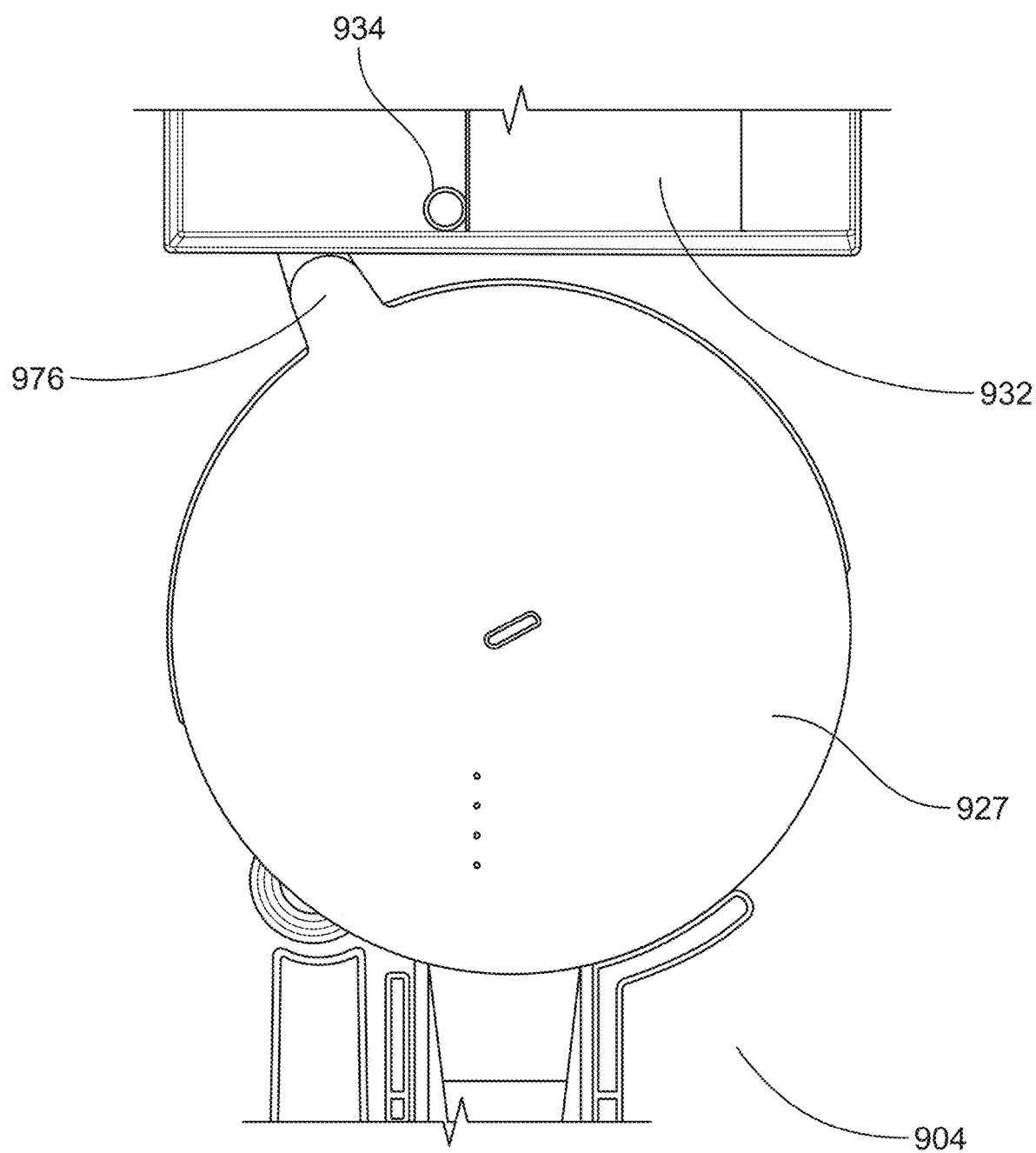
FIG. 9 shows a heating section of an auxiliary unit of a respiratory therapy system, according to an illustrative implementation.

System 400 may also include one or more temperature sensors, such as temperature sensors 542 and 544 of FIG. 5. In some implementations, base unit 402 includes one or more infrared (IR) temperature sensors configured to measure liquid temperatures in auxiliary unit 404 by non-contact means. One or more signals indicating the liquid temperature may be transmitted from the sensor(s) to the controller. The controller may be configured to determine if the measured temperature is within a stored safe temperature range. If the temperature is within the safe range, then the controller may alert the user by one or more alarms (e.g., auditory alarms, notifications on display 430) and/or change one or more controllable operational parameters to effect a change in the temperature. This may involve changing the blower flowrate, In some implementations, base unit 402 includes one or more IR temperature sensors configured to measure a temperature of the heater plate that is immersed in liquid in auxiliary unit 404, for example, to detect overheating of the heater plate. In some implementations, the heater plate includes a tab that protrudes from the top of the heating plate as depicted in FIG. 9. The tab may be disposed such that it is the first part of the heating plate to be exposed (not immersed in liquid) when the liquid is at a low level. When the tab is not immersed, it will heat up quickly if the heating plate and heating element are in operation. A temperature sensor may be disposed to align with the tab when the auxiliary unit is seated, so that the temperature of the tab may be monitored by sending one or more signals indicating the tab temperature to the controller. When the tab heats up quickly during a low liquid level state of auxiliary unit 404, the temperature sensor can detect the rapid rise in temperature and alert the controller. In response to detecting a rapid rise in the tab temperature indicative of a low liquid level, the controller may be configured to turn off the heating element (e.g., the induction coil). In response to detecting a rapid rise in the tab temperature indicative of a low liquid level, the controller may be configured to increase or open the liquid flow from external reservoir 410 by, for example, actuating the occluder valve or pump 424. In response to detecting a rapid rise in the tab temperature indicative of a low liquid level, the controller may be configured to completely shut off system 400 and/or generate an alarm. An alarm may be auditory or visual via display 430.

Delivery tube 406 conducts the breathing gas to the patient. Jacketed delivery tubes are typically smaller in inside diameter than heated wire delivery tubes and have fewer related issues. For example, the weight of liquid needed to properly heat a larger tube can provide a poor user experience if the tube diameter is increased too much, because the user may have difficulty moving a tube substantially weighed down by the liquid. Smaller jacketed delivery tubes can work when the pressure of the pressure source is high enough. In system 400, breathing gas is pressurized and supplied from the blower in base unit 402, without external pressurization in some implementations, so limited pressure may be available. With a blower, the tube diameter needs to be increased to account for a the lower pressure source. It may be advantageous to size a cross-sectional diameter of delivery tube 406 to be as large as possible, in order to accommodate the lower back pressure while maintaining functionality. Generally, an increased diameter increases the weight of the delivery tube due to the larger volume of liquid required to heat the gas. Increasing the diameter can also lead to water accumulation in the delivery tube. Unlike the larger heated wire tubes, which must be tilted to drain liquid to the patient, the smaller jacketed tube may deliver water to the patient by simply increasing the flow above a certain threshold where the water may be conducted along the delivery tube by the flow of breathing gas. Accordingly, an upper limit of the diameter may be set based on, when operating at a minimum breathing gas flowrate, the velocity of breathing gas is sufficient to convey any liquid that has built-up in delivery tube 406 as rain-out to patient connector 408 where it may be collected and removed. In some implementations, the breathing gas flowrate is 5 L/min, and the delivery tube inner diameter is less than or equal to about 0.26 in. Delivery tube 406 may be constructed of a flexible material as to allow a user or operator to manipulate delivery tube 406 without obstructing breathing gas flow.

The increased diameter can also make the delivery tube more prone to kinking. Accordingly, delivery tube 406 may be constructed to be kink resistant. In some implementations, delivery tube 406 includes a jacket. As discussed above, heated liquid may be used to heat, in turn, breathing gas. For example, delivery tube 406 may include a jacket configured to receive heated liquid and convey the heated liquid around an inner lumen that conveys the breathing gas. Heated liquid may travel along a full length of delivery tube 406 in a first direction towards patient connector 408, and then return in an opposite direction back to auxiliary unit 404. In some implementations, the jacket includes a plurality of ribs extending in a radial direction through the jacket from a first conduit defining a breathing gas lumen to a second conduit, wherein the jacket is defined as the annular space between the first conduit and the second conduit. The radial ribs define two or more channels of the jacket through which liquid may flow. The radial ribs allow bending of delivery tube 406 in any direction without kinking by preventing collapse of the inner breathing gas conduit when delivery tube 406 is bent. In some implementations, under flexure of delivery tube 406, one or more of the channels may collapse, but at least some of the channels and the breathing gas lumen remain open to allow for liquid and breathing gas flow, respectively. The jacket having radial ribs may mimic a thick-walled tube to prevent collapse of the breathing gas lumen. In some implementations, the breathing gas lumen wall has a thickness proportional to the breathing gas lumen inside diameter. In some implementations, the outer wall, defining the jacket, has a thickness proportional to the outer diameter of delivery tube 406 minus the inner diameter of the breathing gas lumen. In some implementations, each radial rib has a width proportional to the wall thickness of the breathing gas lumen.

Display 430 may be configured to show one or more parameters of system 400. For example, display 430 shows any of: breathing gas flowrate, liquid vaporization/consumption rate, humidity, liquid level, breathing gas velocity, heating plate temperature, and liquid temperature. In some implementations, display 430 acts as an interface for both alerting the user of system parameters and for accepting user inputs. User inputs, such as those previously described, may include target values for any of these parameters. The user inputs may be transmitted to the controller which is configured to adjust the parameters, for example, by actuating one or more of the components of system 400.

Breathing Gas and Liquid Flow Paths

As described above in relation to FIG. 4, the liquid in systems described herein follows a flow path during operation of said systems. As there are several components that may utilize or act on the liquid, there may be an ordered flow path through which liquid flows and undergoes various state changes or manipulations.

FIG. 5 is a cross-section of a respiratory therapy system 500 configured to output breathing gas to a patient, according to an illustrative implementation. System 500 includes a base unit 502 having a recess 518 in which auxiliary unit 504 is seated. Latch 520 locks auxiliary unit 504 in its current position. Liquid is stored in internal reservoir 532 of auxiliary unit 504. External reservoir 510 supplies liquid through external tube 514 to internal tube 515 of auxiliary unit 504. A valve 540 is disposed along external tube 514. Liquid flowing through internal tube 515 is conveyed into internal reservoir 532 through internal reservoir inlet 534. A vent 538 is disposed on internal reservoir 532. Liquid flows out of internal reservoir 532 and then alongside heating plate 527 immersed in the liquid. After heating, liquid flows into pump 524 and then out of pump outlet 546. Auxiliary unit 504 also includes an RFID tag 550 and an alignment marker 548. Base unit 502 includes a stator 522, a level sensor 528, a heat actuator 526, an RFID reader 551, an alignment sensor 549, and temperature sensors 542 and 544. System 500 and its components may combined with or modified by the systems and devices described in FIGS. 4, 6, 7A-7F, 8A, 8B, 9, and 10.

The various components in base unit 502 may be configured to couple to corresponding components of auxiliary unit 504 in a non-contact manner. These components may be operatively coupled to a controller in base unit 502 for actuation and/or electronic communication. In some implementations, stator 522 is configured to magnetically couple to a rotor of pump 524. By magnetically coupling to the rotor, stator 522 may induce rotational motion in the rotor for non-contact control of pump 524. Heat actuator 526 may convey by non-contact means heat to or generate heat in heating plate 527 immersed in liquid. Heat actuator 526 may be operatively coupled to the controller to allow for indirect actuation of the rate at which heat is transferred to liquid surrounding heating plate 527. In some implementations, heat actuator 526 is a coil configured to generate a current in heating plate 527 via induction, the current generating heat due to a resistance in heating plate 527. The generated heat may transfer from immersed heating plate 527 to liquid on either side. In some implementations, level sensor 528 is a capacitive sensor configured to measure capacitance in internal reservoir 532. Internal reservoir 532 may have a constant cross-section 536, so the measured capacitance is indicative of a liquid level in internal reservoir 532. By utilizing capacitive sensing, the system may provide an early warning of low liquid levels and active control of the water level in the system. Measurements of flow rate and humidification may also be more accurate with the use of capacitive sensing to accurately measure remaining liquid water.

In some implementations, RFID reader 551 detects the presence of RFID tag 550 when auxiliary unit 504 is within recess 518. RFID reader 551 may read information stored on RFID tag 550. In some implementations, alignment marker 548 is disposed in latch 520, and alignment sensor 549 is configured to detect the presence of alignment marker 548 when latch 520 is in a locked position. Latch 520 in an unlocked position 521 is depicted in FIG. 5 by a dashed outline. In some implementations, alignment marker 548 is a magnet, and alignment sensor 549 is a Hall effect sensor configured to detect the magnetic field of the magnet. Alignment sensor 549 may transmit to the controller a signal indicating auxiliary unit 504 is fully seated in recess 418 when alignment marker 548 is detected. A barcode may be used in auxiliary unit 504 in addition to or in place of RFID tag 550, such that reader 551 in the base unit reads the barcode when auxiliary unit 504 is fully docked in recess 518 of base unit 502. The barcode may include the information about one or more components, as is described in relation to the RFID tag in this disclosure. As an alternative to alignment marker 548, the base unit may include an infrared (IR) proximity sensor having an IR beam positioned such that latch 520 breaks the beam, triggering the sensor, when auxiliary unit 504 is fully seated. In some implementations, temperature sensors 542 and 544 are IR temperature sensors configured to measure temperatures in auxiliary unit 504. For example, temperature sensor 542 may be positioned to measure a temperature of heating plate 527, and temperature sensor 544 may be positioned to measure a temperature of the liquid flowing away from heating plate 527.

Liquid may flow out of internal reservoir 532 to heating plate 527 and pump 524 due to hydrostatic pressure resulting from the height of internal reservoir 532 positioned above heating plate 527 and pump 524. In some implementations, pump 524 generates a suction pressure that draws liquid from internal reservoir 532, past heating plate 527, and into pump 524. Rotational motion of a rotor (not shown) in pump 524 may be used to convey the liquid along a flow path. The flow path may be partially enclosed in auxiliary unit 504. In some implementations, system 500 further includes a jacketed delivery tube (such as delivery tubes 406 and 706 of FIGS. 4, 7A, 7B, and 7D-7F), and the flow path may extend through the jacket of the delivery tube. In some implementations, pump outlet 546 is in fluid communication with the jacket, such that heated liquid is pumped into the jacket for heating of the breathing gas in an inner lumen of the delivery tube, wherein the inner lumen is concentrically surrounded by the jacket. Pump 524 may generate sufficient pressure such that liquid is conveyed through a first lumen of the jacket away from auxiliary unit 504 and through a second lumen of the jacket in an opposite direction back to auxiliary unit 504. In some implementations, auxiliary unit 504 houses a vapor transfer cartridge (VTC), such as VTC's 416, 716, and 816 of FIG. 4, and liquid is conveyed from the delivery tube jacket into VTC for humidification of the breathing gas.

In some implementations, pump 524 conveys the liquid in a cyclic manner, in which liquid outputted from pump outlet 546 is pumped first through the delivery tube jacket, then through the VTC, into internal reservoir 532 (e.g., through a recycled liquid reservoir inlet not shown), and finally past heating plate 527 before returning into pump 524. In this case, pump 524 generates enough pressure to convey the liquid through an entire cycle of this flow path for the liquid to return to pump 524. This ordered flow path may define a cycle or loop of fluid flow. This loop may be a closed loop, for example, if valve 540 is closed to prevent fluid flow through external tube 514. The loop may be sealed such that, when the loop is closed, liquid only leaves the loop as vapor in the VTC. In some implementations, the volume of liquid in the loop is at a steady state such that the rate of liquid leaving the loop as vapor in the VTC is equal to the rate of liquid entering the loop through tubes 514 and 515 from external reservoir 510. In other implementations, discrete volumes of the liquid are conveyed from external reservoir 510 through tubes 514 and 515 to the internal reservoir 532 at time intervals, such that the discrete volume for a given time interval is equal to the amount of liquid vaporized during that time interval.

Valve 540 may be used to isolate the volume of liquid in the loop, for example, by closing valve 540 to stop all liquid flow through tubes 514 and 515 from external reservoir 510. In some implementations, level sensor 528 outputs one or more signals to the controller in base unit 502 indicative of the liquid level in internal reservoir 532. Internal reservoir 532 may have constant cross-section 536, such that liquid level may be directly proportional to the volume of liquid in internal reservoir 532. When liquid flow is occluded by valve 540, liquid may only exit the loop by vaporization in the VTC. The controller can determine the vaporization rate (or consumption rate of liquid by the VTC) based on a change in liquid level in internal reservoir 532 over a period of time. If the controller also knows the breathing gas flowrate, for example, by receiving one or more signals indicating the flowrate (e.g., from the measurement device 1086 of FIG. 10), then the controller can be configured to determine the vapor content or humidity of the breathing gas using the breathing gas flowrate measurement(s) and the liquid level measurements. The absolute humidity can also be determined by the controller by also taking into account temperature measurements, for example, indicated by one or more signals transmitted to the controller by temperature sensors configured to measure the temperature of the breathing gas in the VTC, at the VTC exit, or in the delivery tube While external valves such as valve 540 can be used to control liquid flow from an external reservoir, it can be advantageous have a valve built into an auxiliary unit to, for example, allow for optimized control of the liquid flow by a controller. Furthermore, as the use of breathing gas and liquid is intertwined, a built-in valve that provides simultaneous control over breathing gas and liquid flows may enable further optimization and ease of control.

Figure 6:
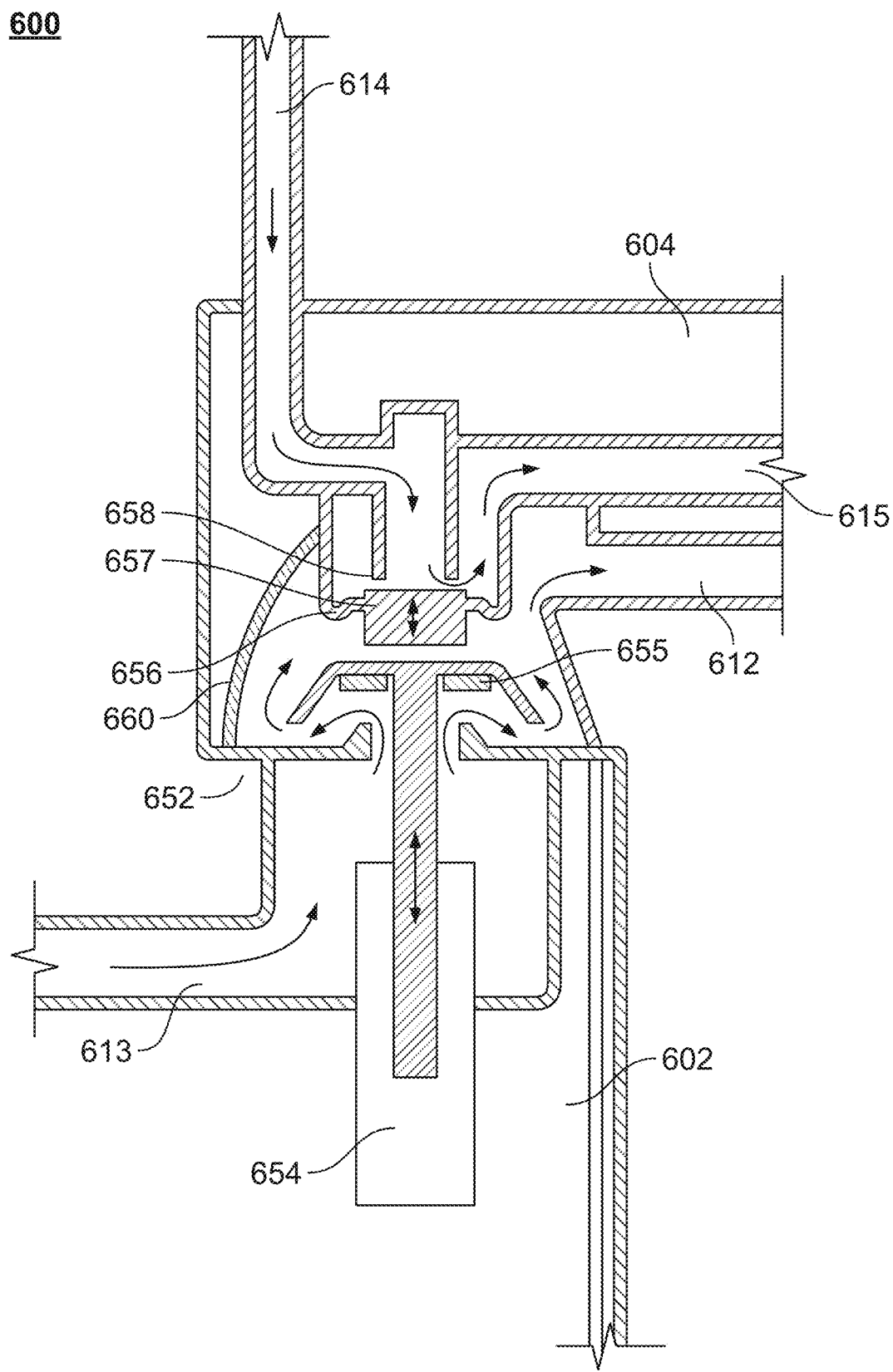
FIG. 6 shows a cross-section of an occluder valve for linking a base unit and an auxiliary unit, according to an illustrative implementation.

FIG. 6 depicts a portion of a respiratory therapy system 600 having a base unit 602 and auxiliary unit 604 joined by an occluder valve 652, according to an illustrative implementation. Occluder valve 652 is actuated by an actuator 654 which controls the positioning of gas path valve seal 655. Breathing gas enters valve 652 through base unit gas path 613 and exits valve 652 through auxiliary unit gas path 612. Liquid travels through external tube 614 and into valve 652 through liquid inlet 658, and exits valve 652 through internal tube 615. Valve 652 includes a gas seal 660 that is configured to form a closed annular space around gas path valve seal 655 between paths 613 and 612. Valve 652 includes a flexible portion 656 having a liquid path valve seal 657. System 600 and its components may combined with or modified by the systems and devices described in FIGS. 4, 5, 7A-7F, 8A, 8B, 9, and 10.

Actuator 654 is coupled to a controller (not shown) in base unit 602. Actuator 654 may be configured to move in a linear direction, as shown with the up and down arrows on actuator 654. The controller may send one or more signals to actuator 654 in order to adjust the position of actuator 654. Gas path valve seal 655 is coupled to linear actuator 654, such that linear movement of actuator 654 would also move gas path valve seal 655 in a linear direction, allowing gas path valve seal 655 to be positioned in a plurality of positions along the linear direction. Gas path valve seal 655 as shown in FIG. 5 is in a middle position which allows breathing gas flow from gas path 613 into the annular space defined by gas seal 660 in valve 652. As the position of gas path valve seal 655 may be varied, the flowrate of breathing gas from gas path 613 may be varied as a result of actuating gas path valve seal 655 by actuator 654. From the middle position of gas path valve seal 655 as shown in FIG. 5, actuator 654 may be configured to raise gas path valve seal 655 to enlarge the gap and increase the breathing gas flowrate through valve 652. Actuator 654 may be configured to lower gas path valve seal 655 to narrow the gap defined by gas path valve seal 655 and decrease the breathing gas flowrate through valve 652. Actuator 654 may lower gas path valve seal 655 by a certain distance such that gas path valve seal 655 fully occludes breathing gas flow from gas path 613, reducing the breathing gas flowrate to zero.

Flexible portion 656 may similarly have a variable position by virtue of its flexibility. Flexible portion 656 and liquid path valve seal 657 may be moved in a linear direction indicated by the up and down arrows on liquid path valve seal 657. Liquid path valve seal 657 may be formed integrally in flexible portion 656 or disposed in flexible portion 656. Liquid path valve seal 657 may be rigid relative to flexible portion 656, for example, by having a greater thickness than portion 656 or having a reinforced structure. Gas path valve seal 655 may be raised by actuator 654 from its position indicated in FIG. 6 such that gas path valve seal 655 abuts liquid path valve seal 657. Accordingly, controlling actuator 654 may allow system 600 to adjust the position of liquid path valve seal 657 by pushing up against it with gas path valve seal 655. Adjusting the position of liquid path valve seal 657 either narrows or enlarges a gap between liquid inlet 658 and liquid path valve seal 657, wherein liquid from external tube 614 flows through the gap when entering valve 652 on its path into auxiliary unit 604. Narrowing and enlarging the gap may decrease and increase, respectively, the flowrate of liquid out of liquid inlet 658.

Accordingly, valve 652 may provide simultaneous control of both breathing gas and liquid flowrates into auxiliary unit 604. In some implementations, linear actuation of actuator 654 allows for a non-discrete positioning of valve seals 655 and 657. In some implementations, the controller is configured to control actuator 654 between a discrete set of positions. In some implementations, the set includes number of positions >1, >2, >5, >10, or >20. In some implementations, three distinct positions of valve 652 are enumerated: (1) a retracted position, wherein the gas path valve seal 655 is fully lowered, and liquid path valve seal 657 is not abutted, such that gas path 613 is fully occluded, and liquid inlet 658 is fully open to allow liquid flow from exterior tube 614 to tube 615; (2) a middle position (shown in FIG. 5), wherein gas path valve seal 655 is partially raised to allow breathing gas flow from gas path 613, and liquid path valve seal 657 is not abutted to allow for liquid flow from external tube 614 out of liquid inlet 658 to internal tube 615; and (3) an extended position, wherein gas path valve seal 655 is fully extended to allow breathing gas flow from gas path 613 and to abut liquid path valve 657 such that it occludes liquid inlet 658, blocking liquid flow from external tube 614. These three positions are summarized in Table 3.

TABLE 3

Exemplary positions of an occluder valve for controlling gas and liquid flows into an auxiliary unit described herein.

| Valve Position | Gas Path | Liquid Path |
| --- | --- | --- |
| Retracted | Closed | Open |
| Middle | Open | Open |
| Extended | Open | Closed |

The three positions described above may be used for certain purposes. For example, the middle position is used for refilling an internal reservoir of auxiliary unit 604 while breathing gas is delivered. The reservoir may be internal reservoir 532 of FIG. 5. The extended position may be used for isolating the internal reservoir to prevent overfilling or when system 600 is in a standby or low-power mode, as described herein. For example, standby mode may involve only providing breathing gas without vaporizing liquid into the breathing gas through a VTC. Standby mode may be initiated by the controller when a main battery of base unit 602 is removed and system 600 operates on power from a reserve battery in base unit 602. The retracted position may be used when auxiliary unit 604 is removed or detached from base unit 602. In this circumstance, the retracted position may be advantageous in order to protect the gas path 613 of base unit 602 from ingress (e.g., of liquid, dust, particles, contaminants, cleaning solvents).

The controller may be configured to operate actuator 654 to alternate between the valve positions based on received signals. In some implementations, auxiliary unit 604 further comprises an internal reservoir (such as internal reservoir 532 of FIG. 5) for holding the liquid and a level sensor (such as level sensor 538 of FIG. 5) configured to measure the liquid level in the internal reservoir. The level sensor may transmit a signal to the controller indicating that the liquid level is substantially low, and the controller may respond to the signal by actuating valve 652 from the extended position to the middle position, allowing liquid flow into internal tube 615. A low liquid level may also be indicated to the controller by a temperature sensor (such as temperature sensor 542 of FIG. 5) that measures temperature of a heating plate immersed in liquid in auxiliary unit 604, such that a low liquid level is indicated by a rapid increase in the heating temperature when at least a portion of the heating plate is no longer immersed in liquid. In response to one or more signals from the temperature sensor, the controller may actuate valve 652 from the extended position to the middle position to allow liquid flow into internal tube 615 to replenish the internal reservoir and re-immerse the heating plate. In some implementations, auxiliary unit 604 comprises an alignment marker (such as alignment marker 548 of FIG. 5), and base unit 602 includes an alignment sensor (such as alignment sensor 549 of FIG. 5) configured to detect the presence of the alignment marker when auxiliary unit 604 is fully seated in base unit 602. The alignment sensor may transmit a first signal to the controller indicating that it has detected the presence of the alignment marker, indicating auxiliary unit 604 is fully seated, and the controller may respond to the first signal by actuating valve 652 from the retracted position to the middle position, allowing breathing gas and liquid flow into gas path 612 and internal tube 615, respectively, of auxiliary unit 604. The controller may alternatively respond to the first signal by actuating valve 652 from the retracted position to the extended position, for example, if the internal reservoir is full of liquid. The alignment sensor may transmit a second signal to the controller indicating that it no longer detects the presence of the alignment marker, indicating auxiliary unit 604 has been unseated or dislodged, and the controller may respond to the second signal by actuating valve 652 from the extended or middle positions to the retracted position. In some cases, valve 652 remains in the extended position for a fixed period of time or until an internal reservoir of auxiliary unit 604 is depleted of liquid, in order to measure the vaporization rate. Valve 652 may then be moved to the middle position to refill the reservoir via liquid flow path 615.

Flexible portion 656 separates the liquid flow path from the breathing gas flow path, and its flexibility allows for control of the liquid flowrate from the breathing gas side of flexible portion 656. Flexible portion 656 may be constructed from a material that is substantially flexible as to allow upward force from gas path valve seal 655 to vary the position of flexible portion 656 and liquid path valve seal 657. Suitable materials may include ethylene vinyl acetate, polyethylene, polyethylene based polyolefin elastomers, polypropylene, polyurethane, styrene butadiene copolymer, thermoplastic polyester elastomer, polypropylene based elastomers, thermoplastic polyurethane elastomer, polyvinylidene fluoride, fluorinated ethylene propylene, nylon, nylon blends, polystyrene, polyvinyl chloride, polytetrafluorethylene, and thermoplastic vulcanizate. In some implementations, gas seal 660 is formed of a flexible material, such that it may be compressed when auxiliary unit 604 is seated in base unit 602 to form a sealed annular space between gas paths 613 and 612, as shown in FIG. 6 where gas seal 660 forms an annular space around gas path valve seal 655. Gas seal 660 may be formed of the same material as flexible portion 656 or any of the materials listed above.

Auxiliary Unit Design

In accordance with the implementations described above and in the following, an auxiliary unit for a respiratory therapy system is provided herein. FIGS. 7A-7F show multiple view angle and cross-sections of an auxiliary unit 704, according to an illustrative implementation. Auxiliary unit 704 may be implemented, for example, in the respiratory therapy systems 400, 500, 600, and 800 of FIGS. 4, 5, 6, 8A, and 8B.

Figure 7A:
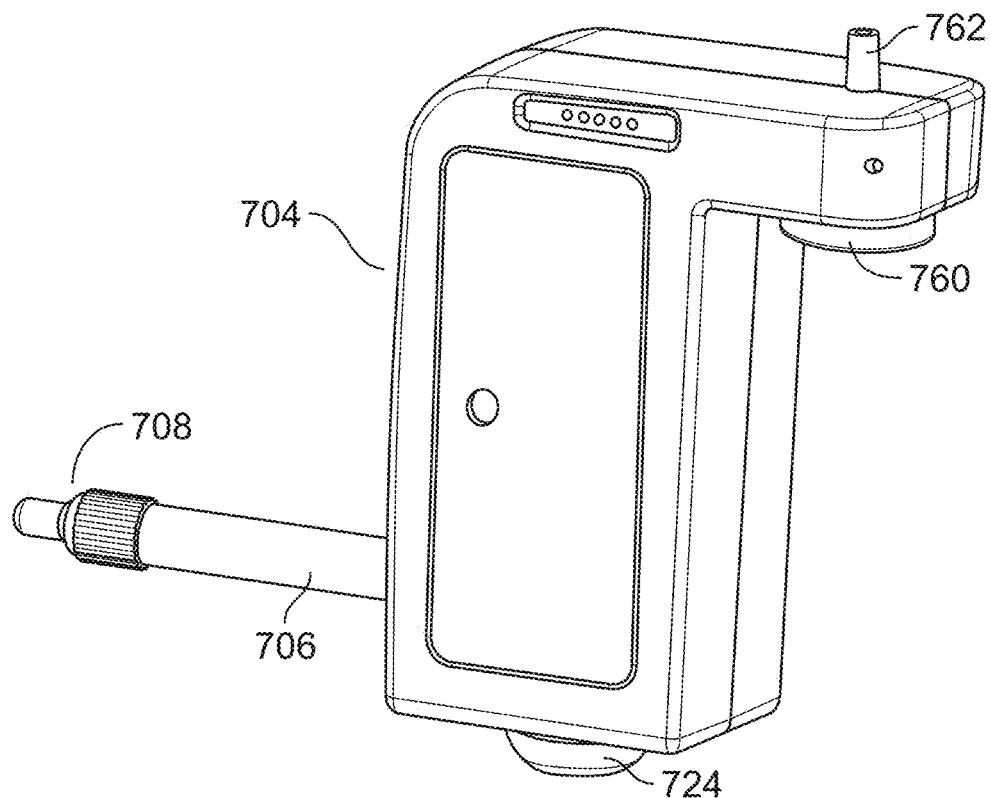
FIGS. 7A-7F show various views and cross-sections of an auxiliary unit, according to an illustrative implementation.

FIG. 7A shows auxiliary unit 704 having a pump 724, a gas seal 760, and an external tube connector 762, according to an illustrative implementation. A delivery tube 706 is connected to auxiliary unit 704, and a patient connector 708 is disposed at a distal end of delivery tube 706. Auxiliary unit 704 is configured to be seated in a base unit (not shown) of a respiratory therapy system which is configured to provide pressurized breathing gas from a blower in the base unit to auxiliary unit 704 during operation. Base unit 402 of FIG. 4 is an example of a base unit that may receive auxiliary unit 704. Gas seal 660, which is part of an occluder valve, forms a sealed flow path for the breathing gas to enter auxiliary unit 704 from the base unit when auxiliary unit 704 is seated in the base unit. External tube connector 762 is configured to connect an external tube (not shown) that provides liquid to auxiliary unit 704 from an external reservoir (not shown). For example, external tube 414 and external reservoir 410 of FIG. 4 may be used in this implementation. Pump 724 is configured to convey the liquid from within auxiliary unit 704.

Delivery tube 706 is configured to receive a flow of breathing gas from auxiliary unit 704 and convey the breathing gas to a patient, through patient connector 708 at the distal end of delivery tube 706. In some implementations, a nasal cannula is connected to patient connector 708 to provide the breathing gas into at least one nare of the patient. The breathing gas may be humidified with the liquid by a VTC in auxiliary unit 704. Pump 724 may convey the liquid along a flow path, including through the VTC in which at least a portion the liquid may be vaporized into the breathing gas which is simultaneously passed through the VTC. When auxiliary unit 704 is seated in the base unit, pump 724 may couple to a pump actuator in the base unit, and the pump actuator may be operatively coupled to a controller which may control the power supplied to pump 724. For example, pump 724 may include a rotor which is configured to magnetically couple to a stator in the base unit. Through the magnetic coupling, rotational motion of the rotor is generated and used to convey fluid along the flow path. In some implementations, the flow path includes a jacket of delivery tube 706.

Figure 7B:
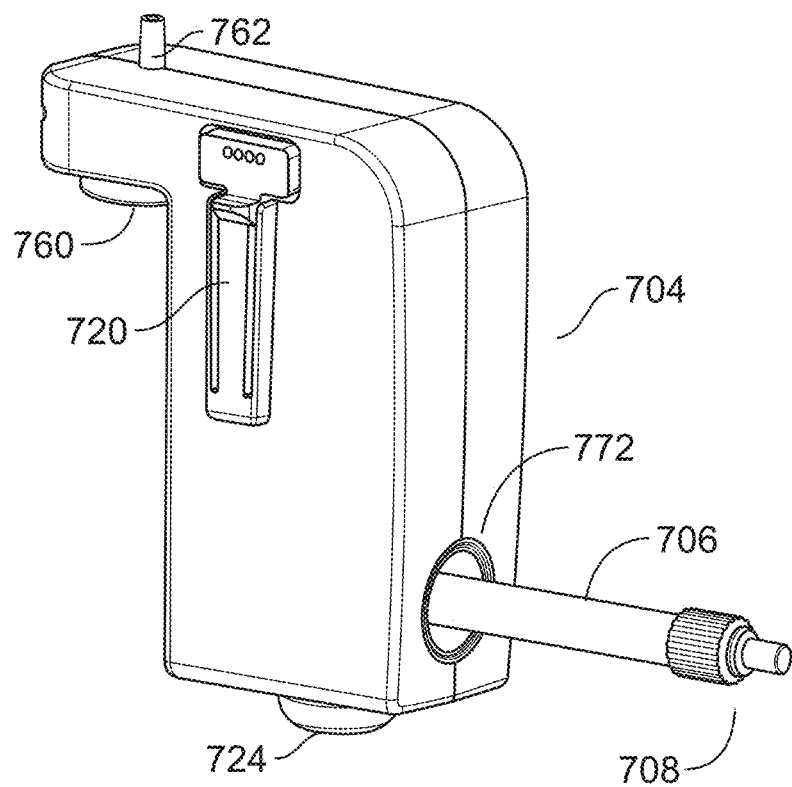

FIG. 7B shows an alternate view angle of auxiliary unit 704. From this angle, a latch 720 is shown on the side of auxiliary unit 704, according to an illustrative implementation. Latch 720 locks auxiliary unit 704 into the base unit when auxiliary unit 704 is fully seated. Delivery tube 706 is connected to auxiliary unit outlet 772.

Latch 720 allows auxiliary unit 704 to be locked and unlocked from its fully seated position in the base unit. Latch 720 may enable locking of auxiliary unit 704 by having a ridge that resides in a notch in the base unit. A user or operator may press against latch 720 to release latch 720 from the notch and unlock auxiliary unit 704 when removing it from the base unit. Latch 720 may have one or more components embedded in it. For example, a marker, such as alignment marker 548 of FIG. 5, may be embedded in latch 720, and the base unit may include a sensor, such as alignment sensor 549 of FIG. 5, configured to detect the presence of the marker when auxiliary unit 704 is fully seated in the base unit and latch 720 is locked. In some implementations, the marker is a magnet, and the sensor is a Hall effect sensor configured to detect the magnetic field of the magnet. In some implementations, latch 720 includes an RFID tag, such as RFID tag 550 of FIG. 5, and the base unit includes an RFID reader, such as RFID reader 551 of FIG. 5, configured to detect the presence of the RFID tag and read information stored on the RFID tag. The information on the RFID tag may identify auxiliary unit 704 as having certain functionalities, may provide use history of auxiliary unit 704, or may provide recommended system parameters such as flowrates, humidity level, and temperature. A barcode may be used in auxiliary unit 704 in addition to or in place of an RFID tag or other tag, or magnet, such that a reader in the base unit reads the barcode when auxiliary unit 704 is fully docked in the recess of the base unit. The barcode may include the information about one or more components, as is described in relation to the tags in this disclosure. As another option, the base unit includes an infrared (IR) proximity sensor having an IR beam positioned such that latch 720 breaks the beam, triggering the sensor, when auxiliary unit 704 is fully seated. Other options for auxiliary unit presence sensing include quick response (QR) codes, global positioning system (GPS) chips, Bluetooth®, Bluetooth® low-energy, near-field communication (NFC), and pattern recognition matching.

Auxiliary unit outlet 772 functions as a port for connection of delivery tube 706 to auxiliary unit 704 for transmission of the breathing gas. Outlet 772 may have a shape such that delivery tube 706 can bend and rotate at outlet 772 without being kinked by the edges of outlet 772. The shape of outlet 772 may also prevent dislodging of delivery tube 706 from auxiliary unit 704. In some implementations, outlet 772 is cone shaped. In some implementations, outlet 772 is chamfered. In some implementations, outlet 772 is filleted. Outlet 772 may be configured to have no hard edges that may kink or damage delivery tube 706; for example, outlet 772 may be rounded.

Figure 7C:
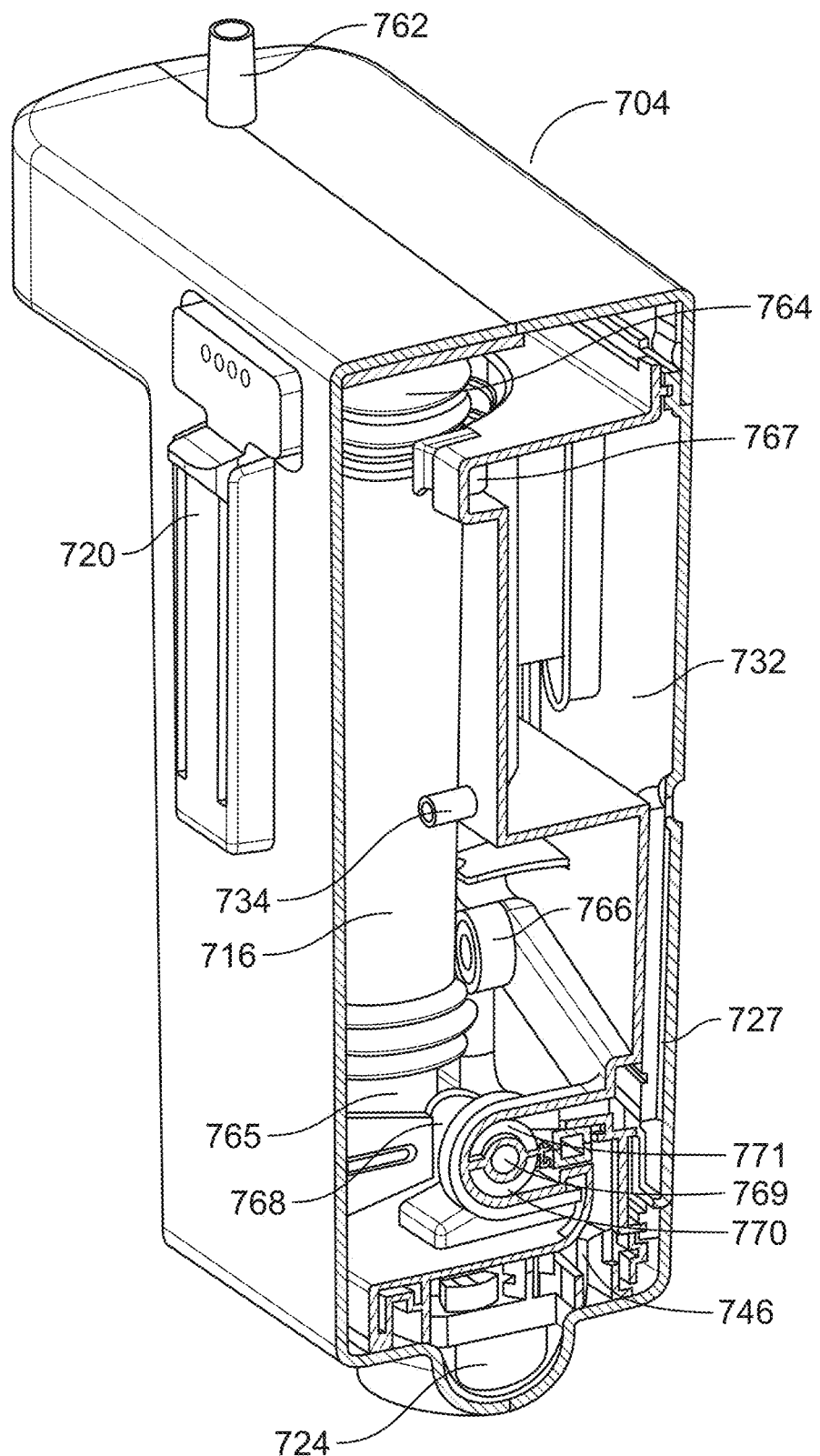

FIG. 7C shows a cross-section of auxiliary unit 704 which includes, in addition to the components previously described, a VTC 716, a heating plate 727, an internal reservoir 732, and a delivery connector 768, according to an illustrative implementation. Liquid is provided to internal reservoir 732 at reservoir inlet 734 which receives liquid from an internal tube (not shown), for example, internal tubes 515 and 615 of FIGS. 5 and 6. Liquid flows out from internal reservoir 732 past heating plate 727 which is immersed in the liquid during operation. Liquid is drawn into pump 724 which expels liquid through pump outlet 746. VTC 716 has a first cap 764 configured to receive breathing gas and a second cap 765 configured to output breathing gas to delivery connector 768. VTC 716 also includes VTC liquid inlet 766 and VTC liquid outlet 767. Delivery connector 768 is configured to convey breathing gas from second cap 765 of VTC 716 to delivery tube 706 through connector gas outlet 769. Delivery connector 768 further includes connector liquid outlet 770 and connector liquid inlet 771.

Liquid entering auxiliary unit 704 through liquid tube connector 762 is directed to reservoir inlet 734 by an internal tube (not shown), such as internal tube 515 of FIG. 5. Liquid stored in internal reservoir 732 may flow out of internal reservoir 732 to a heating section where heating plate 727 is immersed in liquid. In some implementations, liquid flows into the heating section due to hydrostatic pressure and/or gravitational flow, a result of internal reservoir 732 being positioned above the heating section. In some implementations, pump 724 generates a suction pressure that draws liquid out of internal reservoir 732 and into the heating section before being drawn into pump 724. When auxiliary unit 704 is seated in the base unit, heating plate 727 may be coupled to a heat actuator in the base unit. In some implementations, the heat actuator is a coil configured to generate a current in the heating plate via induction, and the current produces heat due to a resistance in the heating plate.

Liquid flows or is drawn into pump 724 from the heating section. The pump expels liquid out of pump outlet 746 which is in fluid communication with connector liquid outlet 770 of delivery connector 768. Delivery connector 768 may be an overmolded rubber piece having one or more lumens. Connector liquid inlet 770 conveys pumped, heated liquid from pump outlet 746 into a jacket of delivery tube 706. The jacket concentrically surrounds an inner gas conduit through which breathing gas is conveyed, such that the heated liquid flowing through the jacket insulates the breathing gas in the inner gas conduit. This feature may be advantageous as to maintain a sufficiently high breathing gas temperature in order to prevent rain-out of vapor in the breathing gas. Rain-out occurs when vapor in the breathing gas condenses into its liquid form during gas delivery. This condensation can cause obstruction of delivery tube 706, patient connector 708, or a nasal cannula connected to patient connector 708. The heated liquid travels in two directions in the jacket, and the jacket accordingly includes at least two lumens or channels, where each lumen or channel connects to either connector liquid outlet 770 or connector liquid inlet 771. For example, liquid is pumped through connector liquid outlet 770 into a first jacket channel which conveys the liquid along delivery tube 706 in a first direction towards patient connector 708. At the distal end of delivery tube 706, where patient connector 708 is disposed, the liquid may change directions and enter a second channel which conveys the liquid along delivery tube 706 in a second direction which is substantially opposite of the first direction. The second channel conveys the liquid into connector liquid inlet 771 of delivery connector 768.

Connector liquid inlet 771 is in fluid communication with VTC liquid inlet 766 in order to convey the fluid from the jacket to VTC 716. Within VTC 716, liquid may be vaporized into the breathing gas conveyed into VTC 716 through first cap 764. For example, the liquid may be water, and VTC 716 may output from second cap 765 a flow of humidified breathing gas containing water vapor. For vaporization to occur, the temperature in VTC 716 may be at or near the gas therapy temperature. Heating plate 727 may heat the liquid to a sufficiently high temperature, e.g., about 100° F. VTC 716 may contain a plurality of fibers, such as the permeable fibers or semi-permeable fibers 884 of FIG. 8B, which allow vapor to pass from the liquid flow into the breathing gas flow. Liquid that is not vaporized in VTC 716 may flow out of VTC liquid outlet 767 which returns the liquid to internal reservoir 732.

Breathing gas exiting second cap 765 of VTC 716 is directed through connector gas outlet 769 of delivery connector 768 into delivery tube 706. The breathing gas, which may be humidified or contain vapor, flows through the inner gas conduit of delivery tube 706 and is insulated or heated by liquid flowing through the jacket. At patient connector 708, the breathing gas may be directed directly to the patient or into one or more additional devices, such as a face mask or a nasal cannula. Suitable nasal cannulas are described above and specifically in relation to FIG. 1.

Figure 7D:
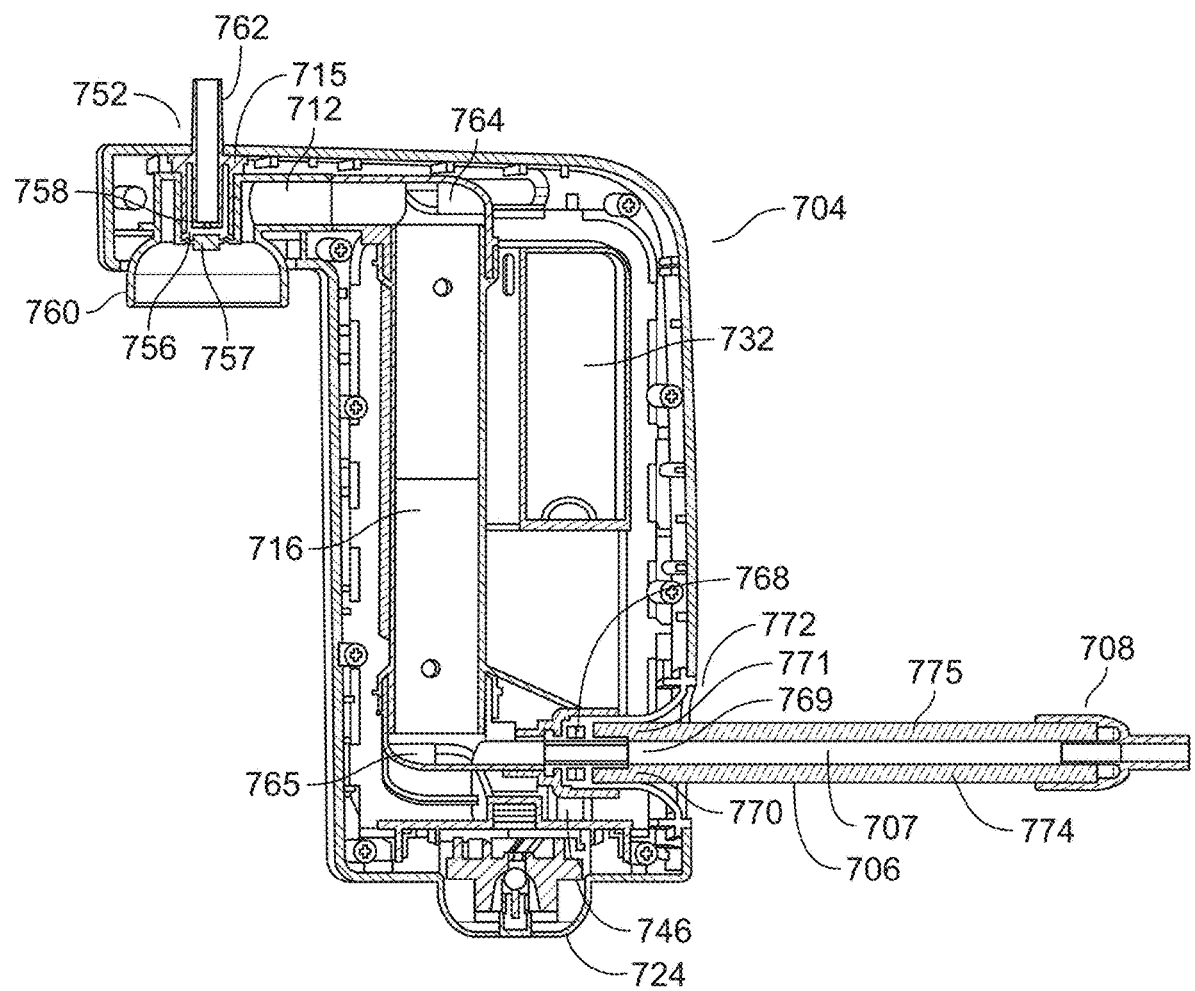

FIG. 7D is cross-sectional view of auxiliary unit 704, according to an illustrative implementation. In this view, an occluder valve 752 is shown in auxiliary unit 704. Delivery tube 706 is connected to delivery connector 768 at auxiliary unit outlet 772. Occluder valve 752 receives liquid flow through external tube connector 762. A flexible portion 756 includes a liquid path valve seal 757 disposed below valve liquid inlet 658. Internal tube 715 is in fluid communication with valve 752 and internal reservoir 732. Gas path 712 is in fluid communication with an annular space formed by gas seal 660 and with first cap 764 of VTC 716.

Occluder valve 752 may be occluder valve 652 of FIG. 6. Occluder valve 752 is configured to mate with the base unit when auxiliary unit 704 is fully seated. As described in relation to FIG. 6, the base unit may include a controller, an actuator, and a gas path valve seal. The controller operates the actuator to adjust a position of the gas path valve seal in order to control breathing gas flow from the base unit into auxiliary unit 704. The gas path valve seal may be raised against the liquid path valve seal 757 in order to simultaneously control liquid flowrate through occluder valve 752, because liquid path valve seal 757 is a rigid piece joined to flexible portion which may be flexed to raise liquid path valve seal 757 to narrow a gap between liquid path valve seal 757 and valve liquid inlet 758. The actuator, gas path valve seal, and liquid path valve seal may have, but are not limited to, three positions which are summarized in Table 3. The controller may operate the actuator to switch between each of these positions based on system inputs or received signals, as described in relation to FIG. 6. Breathing gas may be directed by valve 752 into gas path 712 which conveys breathing gas into first cap 764 of VTC 716. Liquid may be directed by valve 752 into internal tube 715 which conveys liquid into internal reservoir 732.

Delivery tube 706 is connected to delivery connector 768 at auxiliary unit outlet 772 for receiving breathing gas and liquid flows. Delivery tube 706 includes an inner gas conduit 707 configured to receive breathing gas from second cap 765 of VTC 716 through connector gas outlet 769 of delivery connector 768. Delivery tube 706 includes a first jacket channel 774 configured to receive liquid from pump outlet 764 through connector liquid outlet 770 of delivery connector 768. Liquid flows through first jacket channel 774 and a second jacket channel 775, for example, to heat or insulate the breathing gas in inner gas conduit 707. In some implementations, first jacket channel 774 conveys liquid in a first direction away from auxiliary unit outlet 772 and towards patient connector 708. First and second jacket channels 774 and 775 each have distal ends disposed within patient connector 708 which may allow for fluid communication between first and second jacket channels 774 and 775. For example, the liquid flows in the first direction through first jacket channel 774, and, upon reaching patient connector 708, flows out of the distal end of first jacket channel 774 and into the distal end of second jacket channel 775. Liquid may then flow through second jacket channel 775 in a second direction which may be substantially opposite of the first direction. Second jacket channel 775 conveys the liquid back into delivery connector 768 through connector liquid inlet 771. In some implementations, first jacket channel 774 covers a first portion of inner gas conduit 707, the first portion having an approximately semi-circular cross-sectional shape. Second jacket channel 775 may cover a second portion on the opposite side of inner gas conduit 707, the second portion having an approximately semi-circular cross-sectional shape. Auxiliary outlet 772 in this implementation has a rounded (filleted) shape which may prevent kinking of delivery tube 706 and occlusion of inner gas conduit 707, first jacket channel 774, and second jacket channel 775 when delivery tube 706 is bended or flexed.

Figure 7E:
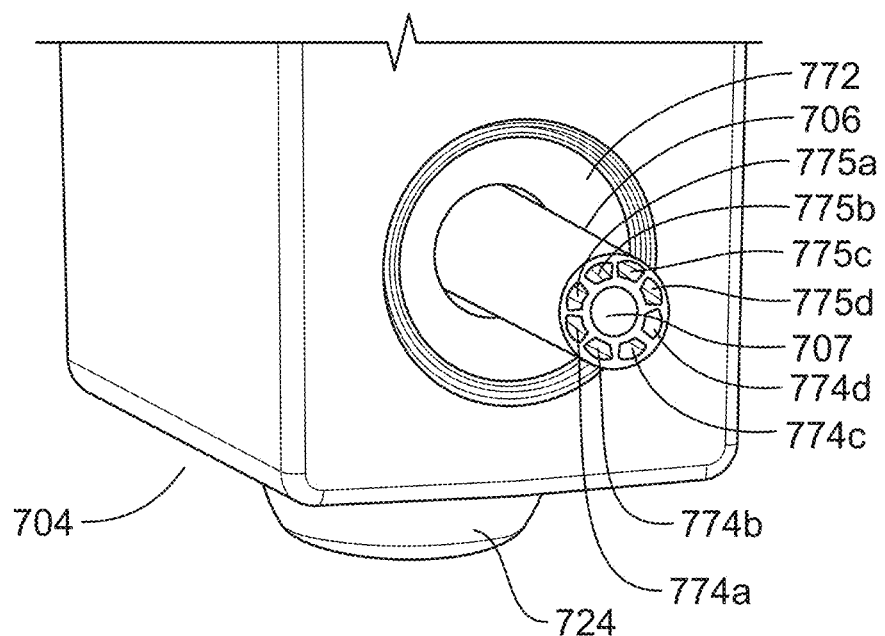
Figure 7F:
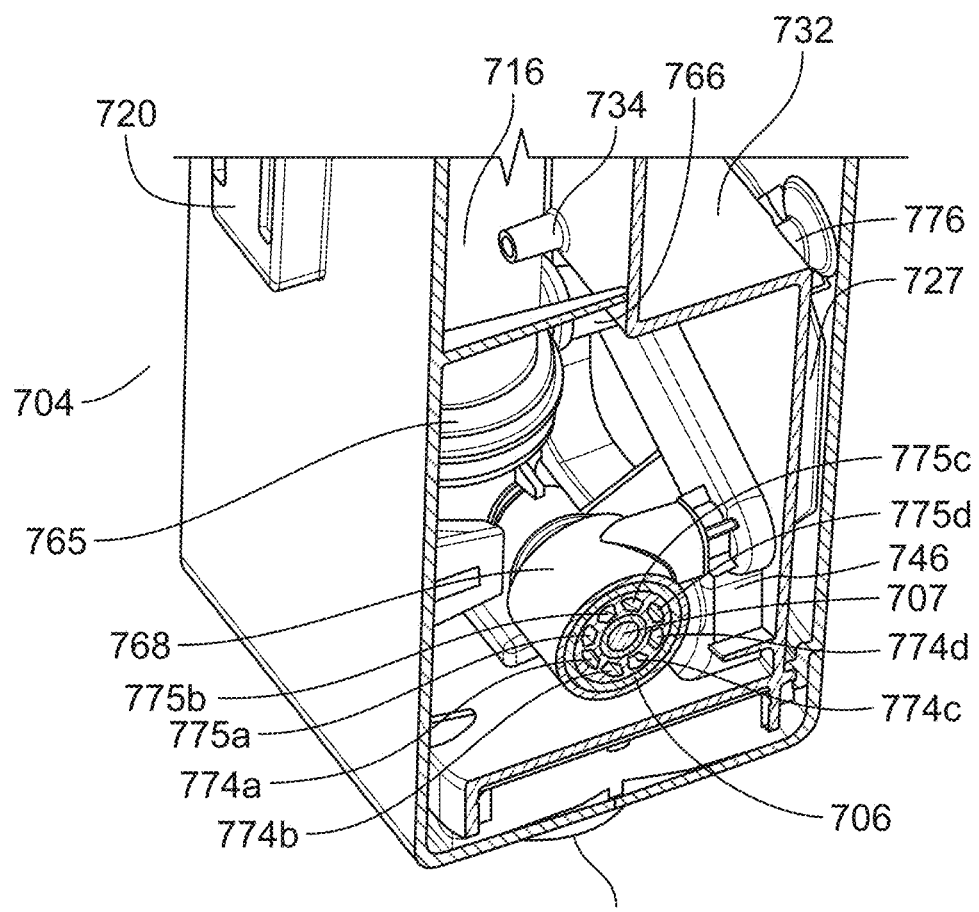

FIGS. 7E and 7F show different cross-sections of a lower portion of auxiliary unit 704, according to an illustrative implementation. In FIG. 7E, delivery tube 706 is connected to auxiliary unit 704 at auxiliary outlet 772, and a cross-section of delivery tube 706 is shown. First jacket channel 774 includes four sub-channels 774a, 774b, 774c, and 774d. Second jacket channel 775 includes four sub-channels 775a, 775b, 775c, and 775d. The plurality of sub-channels surround inner gas conduit 707.

First jacket channel 774 and second jacket channel 775 are divided into sub-channels 774a-d and 775a-d by a plurality of radial ribs. Each radial rib extends from an inner wall defining inner gas conduit 707 to an outer wall of delivery tube 706, wherein the annular space between the inner wall and outer wall defines the jacket. Each pair of radial ribs defines one sub-channel of the jacket through which liquid flows. The radial ribs allow bending of delivery tube 706 in any direction without kinking by preventing collapse of inner gas conduit 707 when delivery tube 706 is bent. In some implementations, under flexure of delivery tube 706, one or more of the sub-channels 774a-d and 775a-d may collapse or become occluded, but at least some of the sub-channels 774a-d and 775a-d and inner gas conduit 707 remain open to allow for liquid and breathing gas flow, respectively. The jacket having radial ribs may mimic a thick-walled tube to prevent collapse of inner gas conduit 707. In some implementations, the inner wall defining inner gas conduit 707 has a thickness proportional to an internal diameter of inner gas conduit 707. In some implementations, the outer wall, defining the jacket, has a thickness proportional to the overall diameter of delivery tube 706 minus the internal diameter of inner gas conduit 707. In some implementations, each radial rib has a width proportional to the inner wall thickness.

In FIG. 7F, a cross-section of auxiliary unit 704 shows delivery tube 706 disposed in delivery connector 768. Sub-channels 774a, 774b, 774c, and 774d of first jacket channel 774 of delivery tube 706 are in fluid communication with connector liquid outlet 770 of delivery connector 768. Sub-channels 775a, 775b, 775c, and 775d of second jacket channel 775 of delivery tube 706 are in fluid communication with connector liquid inlet 771 of delivery connector 768. A tab 776 disposed at the top of heating plate 727.

As described above, first jacket channel 774 is in fluid communication with connector liquid outlet 770 in order to receive liquid from pump outlet 746. Liquid is flowed or pumped through the sub-channels 774a-d and then through sub-channels 775a-d of second jacket channel 775. Inner gas conduit 707 is in fluid communication with connector gas outlet 769 to receive breathing gas from VTC second cap 765.

Tab 776 is disposed at the top of heating plate 727, near internal reservoir 732. In some implementations, tab 776 is disposed at the top of heating plate 727 such that, when liquid in internal reservoir 732 reaches a low enough level, tab 776 is exposed while the rest of heating plate 727 remains immersed in liquid. When auxiliary unit 704 is fully seated in the base unit, a temperature sensor (such as temperature sensor 542 of FIG. 5) may be positioned such that it aligns with tab 776 and can measure the temperature of tab 776. When tab 776 is not immersed in liquid, it will heat up quickly if the heating plate and heating element are in operation. The temperature of the tab may be monitored by sending one or more signals indicating the tab temperature to the controller. When the tab heats up quickly during a low liquid level state of auxiliary unit 704, the temperature sensor can detect the rapid rise in temperature and alert the controller. In response to detecting a rapid rise in the tab temperature indicative of a low liquid level, the controller may be configured to turn off the heat actuator (e.g., an induction coil). In response to detecting a rapid rise in the tab temperature indicative of a low liquid level, the controller may be configured to increase or open the liquid flow from the external reservoir by, for example, actuating occluder valve 752 from the extended position to the middle position to allow liquid flow to refill internal reservoir 732. In response to detecting a rapid rise in the tab temperature indicative of a low liquid level, the controller may be configured to completely shut off the respiratory therapy system. In some implementations, the base unit includes a spring element that may be actuated by the controller to auto-eject auxiliary unit 704 under certain conditions, for example, when a rapid temperature rise is indicated.

In FIG. 7D, valve 752 is shown separate from the corresponding components in the base unit. Actuation of valve 752 is performed by the controller of the base unit. Accordingly, FIGS. 8A and 8B depict system 800 in which valve 852, which may be analogous to valve 752 of FIG. 7D, is in a coupled state when auxiliary unit 804 is seated in recess 818 of base unit 802.

Figure 8A:
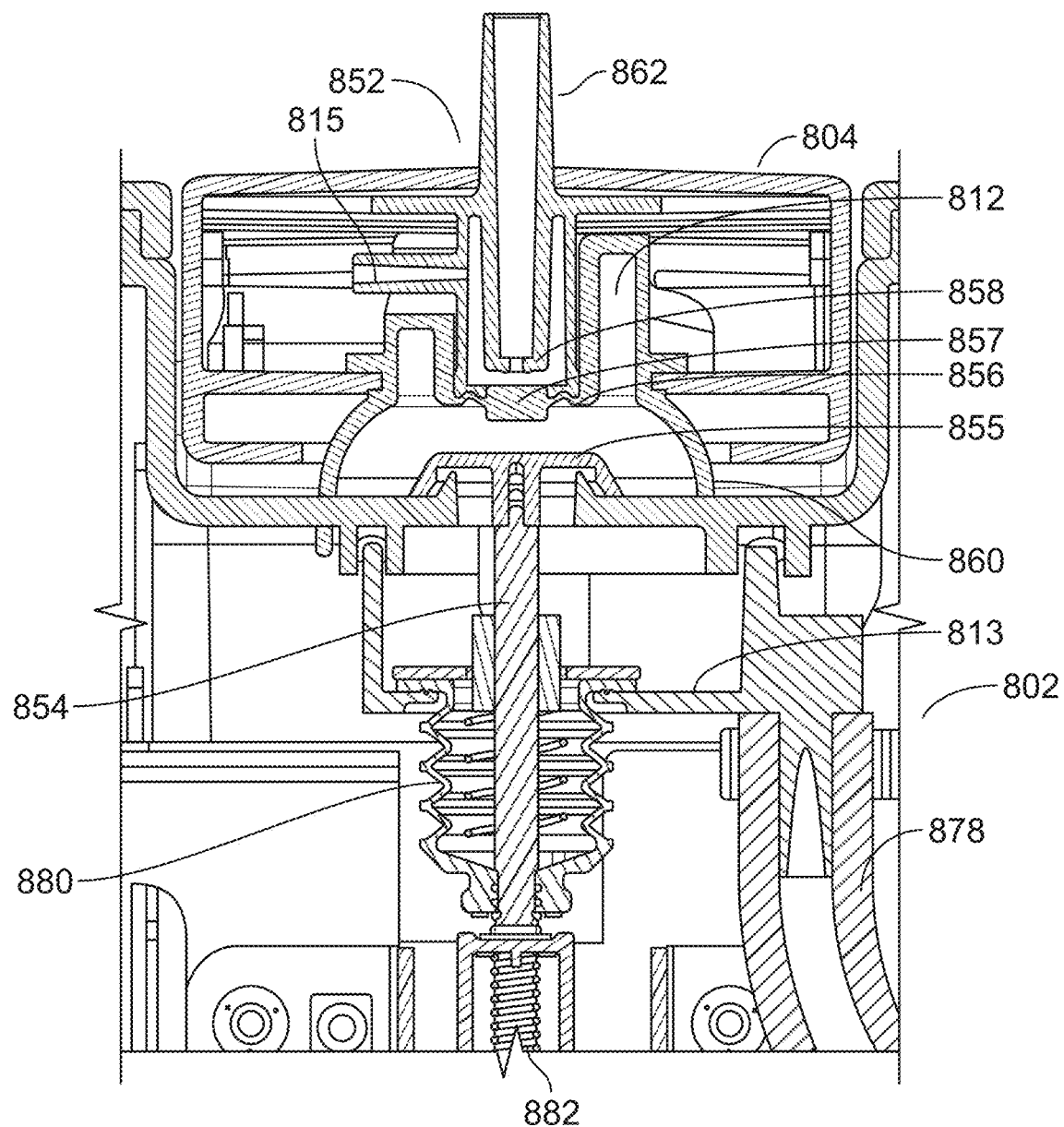
FIGS. 8A and 8B show cross-sections of an occluder valve for linking a base unit and an auxiliary unit, according to an illustrative implementation.
Figure 8B:
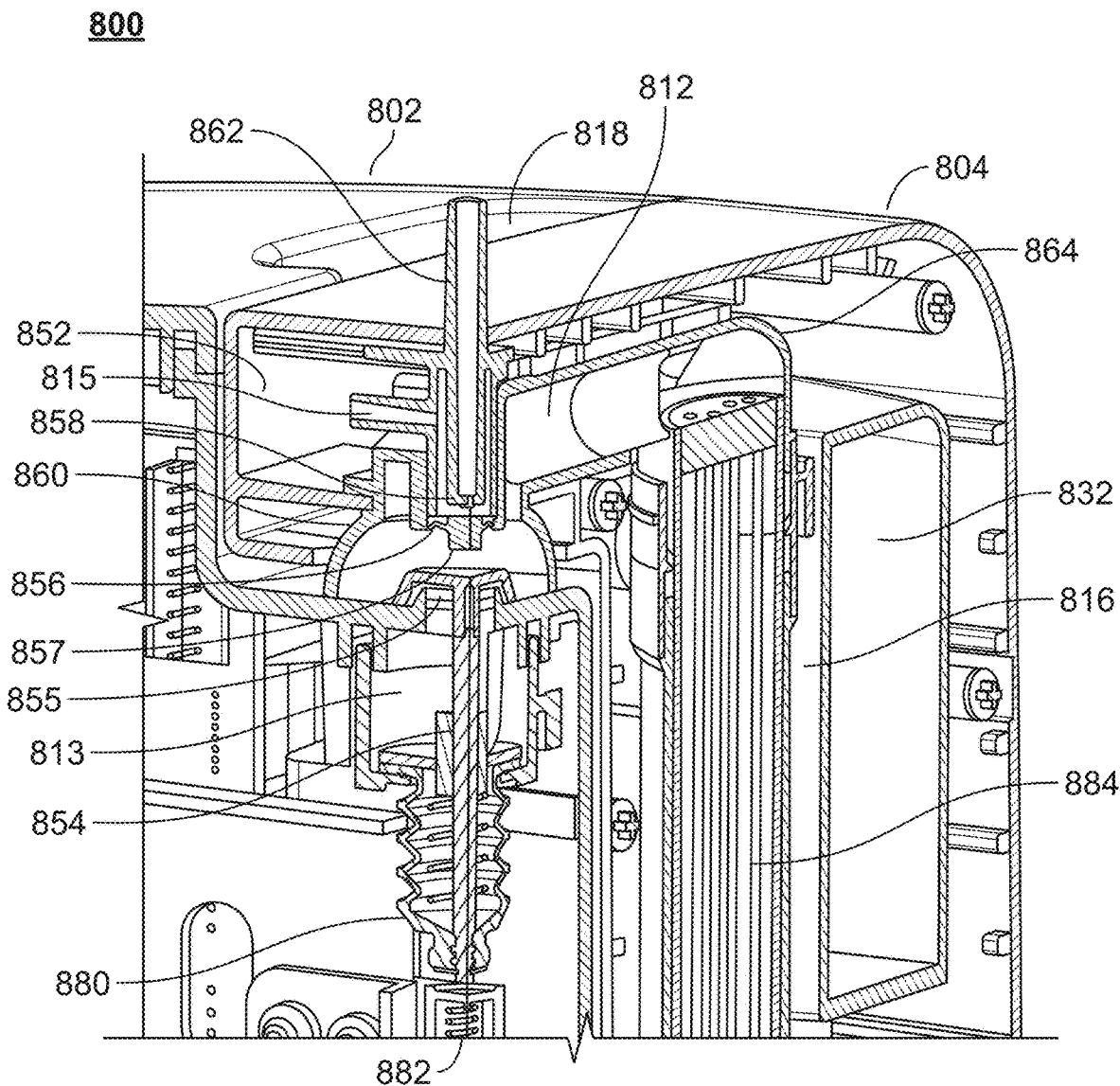

FIG. 8A depicts a cross-section of system 800 which includes an auxiliary unit 804 seated in base unit 802, according to an illustrative implementation. Valve 852 allows simultaneous control of breathing gas from gas path 813 of base unit 802 to gas path 812 of auxiliary unit 804 and of liquid from tube connector 862 to internal tube 815. Breathing gas is provided to gas path 813 from a blower (not shown) via blower tube 878. Valve 852 includes a rod 854 having a variable position controlled by actuator 882. Valve 852 also includes a gas path valve seal 855 and a liquid path valve seal 857 affixed to flexible portion 856. A gas seal 860 defines an annular space around gas path valve seal 855. A rod 854 extends through a bellows 880. Liquid flowing from tube connector 862 flows into valve 852 from valve liquid inlet 858.

Actuator 882 is coupled to a controller (not shown) in base unit 802. Actuator 882 may be configured to move rod 854 in a linear direction, for example, by pushing up against a lower end of rod 854. In some implementations, rod 854 is not affixed to actuator 882. For example, rod 854 may be affixed to an inner surface of bellows 880, and actuator 854 is configured to push against an outer surface of bellows 880, which is flexible, to move rod 854. The controller may send one or more signals to actuator 882 in order to adjust the position of rod 854. Gas path valve seal 855 is coupled to an end of rod 854, such that linear movement of rod 854 would also move gas path valve seal 855 in a linear direction, allowing gas path valve seal 855 to be positioned in a plurality of positions along the linear direction. Gas path valve seal 855 as shown in FIG. 8 is in a retracted position which blocks breathing gas from flowing from gas path 813 into the annular space defined by gas seal 860 in valve 852. Rod 854 is affixed to bellows 880, such that bellows 880 is expanded and contracted as rod 854 is lowered and raised, respectively, by virtue of flexibility of bellows 880.

As both the position of gas path valve seal 855 and the volume of bellows 880 may be varied, the flowrate of breathing gas from gas path 813 may be controlled by adjusting the position gas path valve seal 855 and volume of bellows 880 by actuator 854. From the retracted position of gas path valve seal 855 as shown in FIG. 8A, actuator 854 may be configured to raise gas path valve seal 855 to a middle position to open a gap underneath gas path valve seal 855 and allow breathing gas flow into valve 852. Actuator 854 may be configured to further raise gas path valve seal 855 to an extended position to enlarge the gap underneath gas path valve seal 855 and increase the breathing gas flowrate into valve 852.

Flexible portion 856 may similarly have a variable position by virtue of its flexibility. Flexible portion 856 and liquid path valve seal 857 may be moved in a linear direction. Liquid path valve seal 857 may be formed integrally in flexible portion 856 or disposed in flexible portion 856. Liquid path valve seal 857 may be rigid relative to flexible portion 856, for example, by having a greater thickness than portion 856 or having a reinforced structure. Gas path valve seal 855 may be raised by actuator 854 from its position shown in FIG. 8A such that gas path valve seal 855 abuts liquid path valve seal 857. Accordingly, controlling actuator 854 may allow for adjustment of the position of liquid path valve seal 857 by pushing up against it with gas path valve seal 855. Adjusting the position of liquid path valve seal 857 either narrows or enlarges a gap between liquid inlet 858 and liquid path valve seal 857, wherein liquid from an external tube connected to tube connector 862 flows through the gap when entering valve 852 on its path into auxiliary unit 804. Narrowing and enlarging the gap may decrease and increase, respectively, the flowrate of liquid out of liquid inlet 858.

Accordingly, valve 852 may provide simultaneous control of both breathing gas and liquid flowrates into auxiliary unit 804, similar to valve 652 of FIG. 6. In some implementations, linear actuation of actuator 854 allows for a non-discrete positioning of valve seals 855 and 857. In some implementations, the controller is configured to control actuator 854 between a discrete set of positions. In some implementations, the set includes a number of positions >1, >2, >5, >10, or >20. In some implementations, three distinct positions of valve 852 are enumerated: (1) a retracted position (shown in FIG. 8A), wherein the gas path valve seal 855 is fully lowered, and liquid path valve seal 857 is not abutted, such that gas path 813 is fully occluded, and liquid inlet 858 is fully open to allow liquid flow to internal tube 815; (2) a middle position, wherein gas path valve seal 855 is partially raised to allow breathing gas flow from gas path 813, and liquid path valve 857 is not abutted to allow for liquid flow out of liquid inlet 858 to internal tube 815; and (3) an extended position, wherein gas path valve seal 855 is fully extended to allow breathing gas flow from gas path 813 and to abut liquid path valve seal 857 such that it occludes liquid inlet 858, blocking liquid flow. These three positions are summarized in Table 3 above.

The three positions described above may be used for certain purposes. For example, the middle position is used for refilling an internal reservoir of auxiliary unit 804 while breathing gas is delivered. The reservoir may be internal reservoirs 532 and 732 of FIGS. 5, 7C, 7D, and 7F. The extended position may be used for isolating the internal reservoir to prevent overfilling or when system 800 is in a standby or low-power mode, as described herein. For example, standby mode may involve only providing breathing gas without vaporizing liquid into the breathing gas through a VTC. Standby mode may be initiated by the controller when a main battery of base unit 802 is removed and system 800 operates on power from a reserve battery in base unit 802. The retracted position may be used when auxiliary unit 804 is removed or detached from base unit 802. In this circumstance, the retracted position may be advantageous in order to protect the gas path 813 of base unit 802 from ingress (e.g., of liquid, dust, particles, contaminants), such that the blower and blower tube 878 are not contaminated.

The controller may be configured to operate actuator 854 to alternate between the valve positions based on received signals. In some implementations, auxiliary unit 804 further comprises an internal reservoir (such as internal reservoirs 532 and 732 of FIGS. 5, 7C, 7D, and 7F) for holding the liquid and a level sensor (such as level sensor 538 of FIG. 5) configured to measure the liquid level in the internal reservoir. The level sensor may transmit a signal to the controller indicating that the liquid level is substantially low, and the controller may respond to the signal by actuating valve 852 from the extended position to the middle position, allowing liquid flow into internal tube 815. A low liquid level may also be indicated to the controller by a temperature sensor (such as temperature sensor 542 of FIG. 5) that measures temperature of a heating plate immersed in liquid in auxiliary unit 804, such that a low liquid level is indicated by a rapid increase in the heating temperature when at least a portion of the heating plate is no longer immersed in liquid, for example, when tab 776 of heating plate 727 of FIG. 7 is exposed. In response to one or more signals from the temperature sensor, the controller may actuate valve 852 from the extended position to the middle position to allow liquid flow into internal tube 815 to replenish the internal reservoir and re-immerse the heating plate. In some implementations, auxiliary unit 804 comprises an alignment marker (such as alignment marker 548 of FIG. 5), and base unit 802 includes an alignment sensor (such as alignment sensor 549 of FIG. 5) configured to detect the presence of the alignment marker when auxiliary unit 604 is fully seated in base unit 802. The alignment sensor may transmit a first signal to the controller indicating that it has detected the presence of the alignment marker, indicating auxiliary unit 804 is fully seated, and the controller may respond to the first signal by actuating valve 852 from the retracted position to the middle position, allowing breathing gas and liquid flow into gas path 812 and internal tube 815, respectively, of auxiliary unit 804. The controller may alternatively respond to the first signal by actuating valve 852 from the retracted position to the extended position, for example, if the internal reservoir is full of liquid. The alignment sensor may transmit a second signal to the controller indicating that it no longer detects the presence of the alignment marker, indicating auxiliary unit 804 has been unseated or dislodged, and the controller may respond to the second signal by actuating valve 852 from the extended or middle positions to the retracted position.

Flexible portion 856 separates the liquid flow path from the breathing gas flow path, and its flexibility allows for control of the liquid flowrate from the breathing gas side of flexible portion 856. Flexible portion 856 may be constructed from a material that is substantially flexible as to allow upward force from gas path valve seal 855 to vary the position of flexible portion 856 and liquid path valve seal 857. Suitable materials may include ethylene vinyl acetate, polyethylene, polyethylene based polyolefin elastomers, polypropylene, polyurethane, styrene butadiene copolymer, thermoplastic polyester elastomer, polypropylene based elastomers, thermoplastic polyurethane elastomer, polyvinylidene fluoride, fluorinated ethylene propylene, nylon, nylon blends, polystyrene, polyvinyl chloride, polytetrafluorethylene, and thermoplastic vulcanizate. In some implementations, gas seal 860 is formed of a flexible material, such that it may be compressed when auxiliary unit 804 is seated in base unit 802 to form a sealed annular space between gas paths 813 and 812, as shown in FIG. 8A where gas seal 860 forms an annular space around gas path valve seal 855. Gas seal 860 may be formed of the same material as flexible portion 856 or any of the materials listed above.

FIG. 8B shows another angle of system 800, depicting a cross-section of auxiliary unit 704 which includes a VTC 816 and an internal reservoir 832, according to an illustrative implementation. Auxiliary unit 804 is fully seated in recess 818 of base unit 802. VTC 816 includes a cap 864 which directs breathing gas from gas path 812 to a plurality of fibers 884.

Internal reservoir 832 stores liquid in auxiliary unit 804. Internal tube 815 directs liquid from valve 852 to internal reservoir 832. Liquid is conveyed into VTC 816 in which the liquid may be vaporized into the breathing gas directed through cap 864. For example, the liquid may be water which is vaporized to create a humidified breathing gas. VTC 816 contains the plurality of fibers 884 which allow vapor to pass from the liquid flow into the breathing gas flow. The fibers may be permeable or semi-permeable as to only allow vapor to pass through and to keep liquid separate from the breathing gas. Liquid that is not vaporized in VTC 816 may flow out of a VTC liquid outlet which returns the liquid to internal reservoir 832.

The liquid in auxiliary unit 804 conveyed into VTC 816 must be heated to at or near a boiling point temperature of the liquid in order for at least a portion of the liquid to be vaporized. FIG. 9 shows a heating section of an auxiliary unit 904, the heating section including a heating plate 927 configured to be immersed in liquid and heat the surrounding liquid, according to an illustrative implementation. Liquid is stored in internal reservoir 932, to which liquid is supplied from an external reservoir via reservoir inlet 934. Heating plate 927 includes a protruding tab 976.

In accordance with the implementations previously described, auxiliary unit 904 may be seated in a base unit to form a respiratory therapy system. Heating plate 927 may be configured to couple to a heating element in the base unit when auxiliary unit 904 is seated. In some implementations, the heating element produces a current in heating plate 927 via induction. Induction heating allows the targeted heating of heating plate 927 without contact between the heating element and heating plate 927. The heating element may be a coil. Alternating electrical current, supplied from a power supply of the base unit, may be passed through the coil, creating a variable magnetic field. The coil is formed of a conductive material, such as copper or silver. In this implementation, heating plate 927 is formed of a conductive material. When auxiliary 904 is seated, heating plate 927 is positioned in the magnetic field which induces eddy currents in heating plate 927. The induced eddy currents flow against an electrical resistivity of heating plate 927, generating localized heat in heating plate 927 without any contact between heating plate 927 and the coil. Additional heat may be produced in heating plate 927 in implementations where heating plate 927 is formed of a magnetic material. The additional heat is produced via hysteresis which involves internal friction created when magnetic heating plate 927 is within the magnetic field of the coil, the internal friction producing the additional heat. Suitable materials for heating plate 927 include, but are not limited to, steel, iron, copper, aluminum, lead, silver, tin, and alloys of the preceding.

Tab 976 is disposed at the top of heating plate 927, near internal reservoir 932. In some implementations, tab 976 is disposed at the top of heating plate 927 such that, when liquid in internal reservoir 932 reaches a low enough level, tab 976 is exposed while the rest of heating plate 927 remains immersed in liquid. When auxiliary unit 904 is fully seated in the base unit, a temperature sensor (such as temperature sensor 542 of FIG. 5) may be positioned such that it aligns with tab 976 and can measure the temperature of tab 976. When tab 976 is not immersed in liquid, it will heat up quickly if the heating plate and heating element are in operation. The temperature of the tab may be monitored by sending one or more signals indicating the tab temperature to the controller. When the tab heats up quickly during a low liquid level state of auxiliary unit 904, the temperature sensor can detect the rapid rise in temperature and alert the controller. In response to detecting a rapid rise in the tab temperature indicative of a low liquid level, the controller may be configured to turn off the heat actuator (e.g., an induction coil). In response to detecting a rapid rise in the tab temperature indicative of a low liquid level, the controller may be configured to increase or open the liquid flow from the external reservoir by, for example, actuating occluder valve 952 from the extended position to the middle position to allow liquid flow to refill internal reservoir 932. In response to detecting a rapid rise in the tab temperature indicative of a low liquid level, the controller may be configured to completely shut off the respiratory therapy system. In some implementations, the base unit includes a spring element that may be actuated by the controller to auto-eject auxiliary unit 904 under certain conditions, for example, when a rapid temperature rise is indicated.

Breathing Gas Measurement and Supplementation

Figure 10:
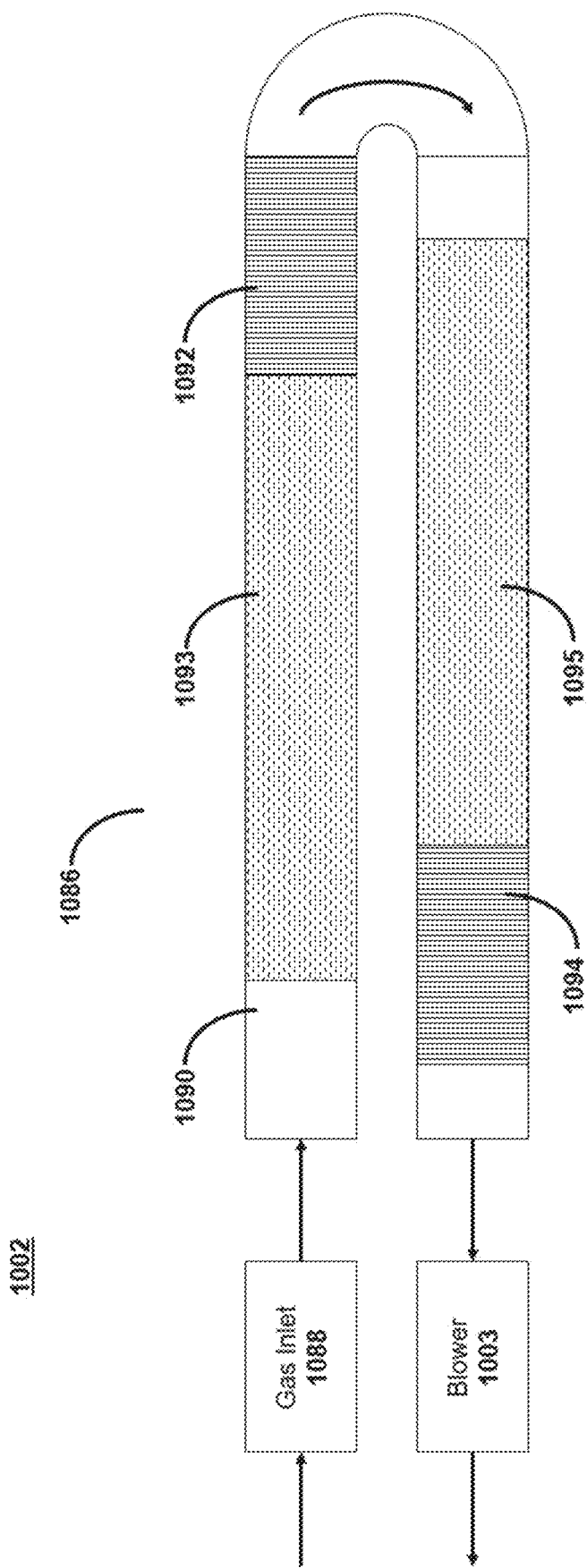
FIG. 10 shows a measurement device, according to an illustrative implementation.

It can be advantageous to measure, monitor, and manipulate breathing gas flow in a base unit described herein. FIG. 10 shows a measurement device 1086 of a base unit 1002, according to an illustrative implementation. Measurement device 1086 is in fluid communication with a gas inlet 1088 and with a blower 1003 of base unit 1002. Measurement device 1086 includes a conduit 1090, a first flow sensor 1092, and first segment 1093, a second flow sensor 1094, and a second flow segment 1095.

Measurement device 1086 may be implemented in any of the base units described herein, including base units 402, 502, 602, and 802 of FIGS. 4, 5, 6, 8A, and 8B. Gas inlet 1088 allows breathing gas to enter base unit 1002 from an external source. In some implementations, gas inlet 1088 draws ambient air from the surroundings. In some implementations, gas inlet 1088 is configured to be coupled to a wall air outlet. Gas inlet 1088 is in fluid communication with blower 1003 via conduit 1090. In some implementations, blower 1003 generates a suction pressure that draws gas into gas inlet 1088 and through conduit 1090.

Gas inlet 1088 directs breathing gas into conduit 1090. First flow sensor 1092 and second flow sensor 1094 are disposed along conduit 1090 and are configured to measure a flowrate of the breathing gas travelling through conduit 1090. First flow sensor 1092 and second flow sensor 1094 may be configured to output one or more signals to a controller in base unit 1002, the signals being indicative of the measured flowrates. The controller is operatively coupled to blower 1003 and may be configured to adjust one or more parameters of blower 1003 based on the received signals indicative of measured flowrates. Appropriate parameters to be adjusted include suction pressure, output pressure, and output flowrate. Blower 1003 may output breathing gas at a high temperature, so a heat exchanger may be disposed at the output of blower 1003. The heat exchanger may be fitted around a tube such that heat disperses from the breathing gas radially outwards into the heat exchanger from the breathing gas. The heat exchanger may be configured to lower the breathing gas temperature to a target temperature, for example, a maximum temperature that prevents malfunction of certain components that come into contact with the breathing gas. For example, a VTC may contain fibers that would be damaged by excessively hot breathing gas.

In some implementations, first flow sensor 1092 and second flow sensor 1094 are mass flow sensors configured to output one or more signals indicative of measured mass flowrates of the breathing gas. Conduit 1090 further includes first segment 1093 and second segment 1095. First segment 1093 is disposed adjacent to first flow sensor 1092, and second segment 1095 is disposed adjacent to second flow sensor 1094. These components are positioned such that breathing gas flowing through conduit 1090 flows through, in order from first to last, first segment 1093, first flow sensor 1092, second segment 1095, and second flow sensor 1094. In some implementations, first segment 1093 and second segment 1095 may be configured to be approximately straight. By straightening first and second segments 1093 and 1095, the breathing gas flows entering first flow sensor 1092 and second flow sensor 1094 are minimized of disturbances in the flow, such that the flow profiles are approximately uniform. For example, first and second flow sensors 1092 and 1094 may provide the most accurate or precise measurements of breathing gas flowrate when the flow profiles of breathing gas entering each sensor are approximately uniform. In some implementations, conduit 1090 also includes straight segments directly after first and second flow sensors 1092 and 1094 to minimize downstream effects of the flow on the measurements.

In some implementations, first flow sensor 1092 and second flow sensor 1094 are configured to each be calibrated relative to the other. When no supplementary gas is being introduced into the gas flow, the flow rate through the first and second flow sensors is identical. The first and second sensors may indicate different flow rates, however due to manufacturing variability, drift over time, or other factors that introduce error to flow sensors. By using first sensor as a reference point and offsetting the indicated flow of the second sensor, the difference between sensors may be reduced to zero. When a supplemental gas is introduced, the flow rate of supplemental gas is calculated as the difference between the flow indicated on the first and second flow sensors. The error in the calculation is thereby reduced to the error of the second sensor.

Figure 11:
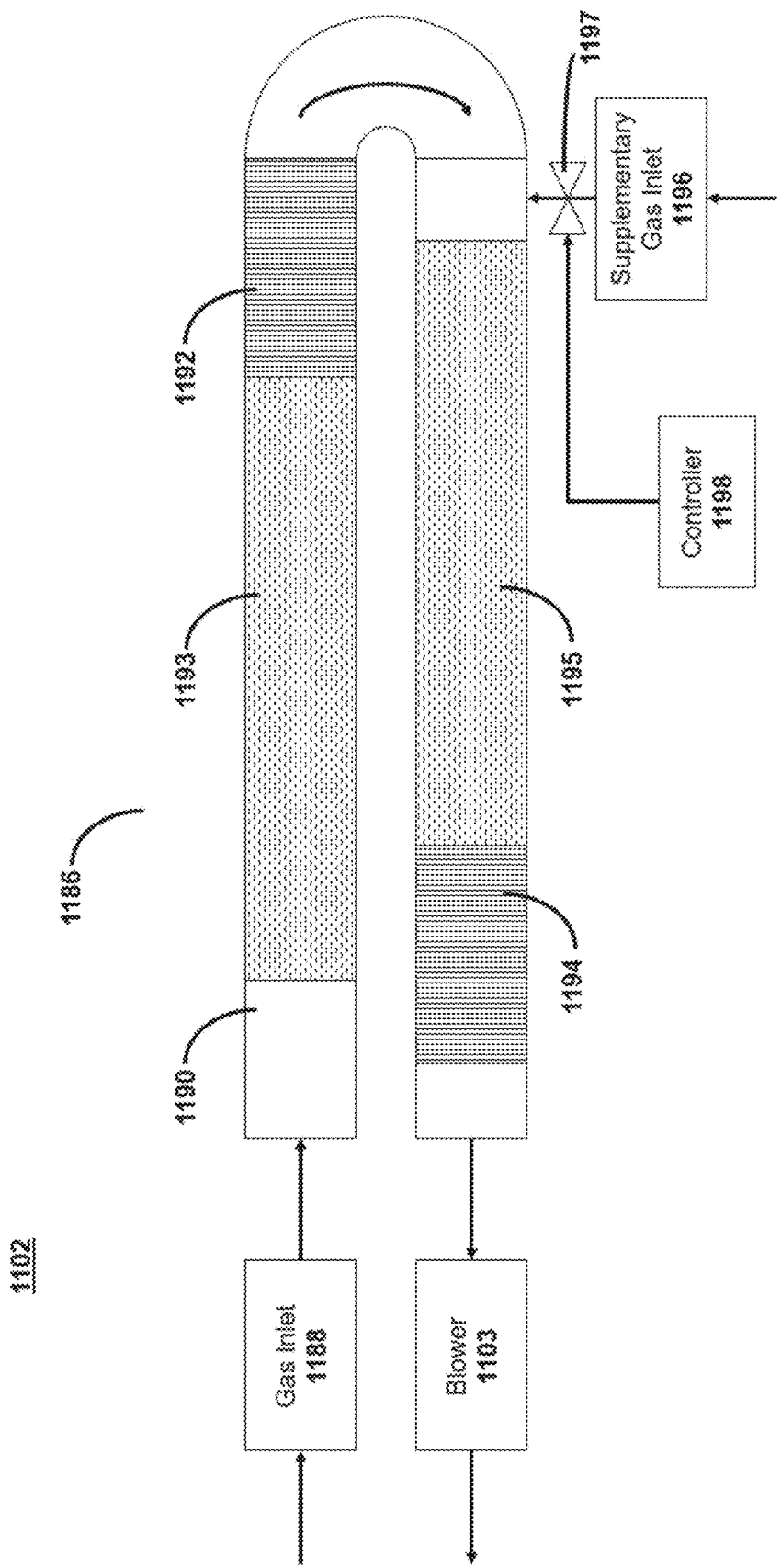
FIG. 11 shows a measurement device configured to receive a supplementary gas, according to an illustrative implementation.

FIG. 11 shows a measurement device 1186 of a base unit 1102, according to an illustrative implementation. Measurement device 1186 includes a conduit 1190 coupled to a gas inlet 1188 and a blower 1103. A first flow sensor 1192 and a second flow sensor 1194 are disposed along conduit 1190. Conduit 1190 includes first segment 1193 and second segment 1195. A supplementary gas inlet 1196 is in fluid communication with conduit 1190 via a supplementary valve 1197. Base unit 1102 includes a controller 1198 operatively coupled to valve 1197.

Base unit 1102 may use the same components of base unit 1002 of FIG. 10 but further includes functionality for introducing a supplementary gas into conduit 1190. Appropriate supplementary gases include, but are not limited to, oxygen, oxygen-concentrated breathing gas, helium, nitric oxide, heliox, anesthetic gas, and gas including aerosolized medicament. Supplementary gas inlet 1196 provides the supplementary gas from an external source, such as, a wall gas outlet, a gas concentrator, or a gas tank. Controller 1198 is configured to actuate supplementary valve 1197 to control the flowrate of supplementary gas entering conduit 1190. Supplementary valve 1197 may be, for example, a solenoid valve, a globe valve, or a diaphragm valve.

Upon entering conduit 1190, the supplementary gas may mix with the breathing gas in conduit 1190 originating from gas inlet 1188. In some implementations, measurement device 1086 is configured such that the breathing gas and supplementary gas are fully or uniformly mixed prior to flowing into second flow sensor 1194. Second segment 1195 may be a sufficient length to allow uniform mixing of the breathing and supplementary gases.

Supplementary gas inlet 1196 and supplementary valve 1197 are positioned to introduce supplementary gas into conduit 1190 at a point between first flow sensor 1192 and second segment 1195. In some implementations, first flow sensor 1192 measures the flowrate of breathing gas, and second flow sensor 1194 measures the flowrate of a mixed flow of breathing gas and supplementary gas. Both first flow sensor 1192 and second flow sensor 1194 are configured to output to controller 1198 signals including a first measurement and a second measurement indicative of the measurements of the breathing gas and the mixed flow, respectively. Upon receipt of the signals, controller 1198 may be configured to calculate a difference between the first measurement and the second measurement. The calculated difference is indicative of the flowrate of supplementary gas introduced via supplementary valve 1197. Controller 1198 may be configured to calculate one or more concentrations of one or more components gas in the mixed flow based on the second measurement and the calculated difference. For example, the supplementary gas may be pure oxygen, and the controller may calculate the concentration of oxygen in the mixed flow based on the second measurement and the calculated difference, the calculated difference indicating the amount of oxygen added to the breathing gas over time.

As mentioned earlier, controller 1198 is configured to actuate supplementary valve 1197 to control the flowrate of supplementary gas entering conduit 1190. Controller 1198 may be configured to adjust the flowrate of supplementary gas by actuating supplementary valve 1197 based on the calculated flow difference and/or the calculated one or more concentrations. For example, controller 1198 may compare a calculated concentration to a target concentration, the target concentration being stored in a memory (not shown) and/or received as an input. The target concentration may be inputted by a user via an interface, such as, a computer link or a display like display 430 of FIG. 4. In this example, controller 1198 may, upon determining the calculated concentration is greater than or less than the target concentration, actuate supplementary valve 1197 to decrease or increase, respectively, the flowrate of supplementary gas, or vice versa.

First flow sensor 1192 and second flow sensor 1194 may be calibrated relative to each other, allowing for the controller to detect small differences in flowrate between first flow sensor 1192 and second flow sensor 1194. For example, the calculated flow difference may be less than about 5% of the measurement from first flow sensor 1192. The calculated flow difference may be less than about 1% of the measurement from first flow sensor 1192. Calibrating first flow sensor 1192 and second flow sensor 1194 relative to each other may reduce an error associated with the flow difference calculation to an error associated with the measurement by second flow sensor 1184. Controller 1198 may be configured to pause or cease flow of supplementary gas through supplementary valve 1197, for example, to calibrate first flow sensor 1192 and second flow sensor 1194 relative to each other while there is no supplementary gas flow.

In some implementations, conduit 1190 is coupled to one or more additional supplementary gas inlets (not shown) configured to introduce one or more additional supplementary gases. There may be one additional flow sensor (not shown) for each additional supplementary gas inlet. These additional flow sensors and additional supplementary gas inlets may alternate in order along conduit 1190, such that controller 1198 may calculate the flowrate of each additional supplementary gas added to the breathing gas stream through conduit 1190, based on the previous methods.

Controller 1190 may include software, hardware, and/or logic to enable closed-loop control of one or more of the breathing gas flowrate, the mixed flow flowrate, a concentration of a component of the mixed flow, temperature, and/or humidity based on data received by controller 1190 from one or more sensors coupled to controller 1190. In addition or alternatively, the closed-loop control may be based on data received from one or more external devices, for example, a pulse oximeter or a transcutaneous carbon dioxide sensor.

External Monitoring

In another aspect of the present disclosure, one or more external monitoring devices may be coupled to a base unit via corresponding one or more interfaces or ports. For example, a pulse oximeter and/or a transcutaneous carbon dioxide sensor may be coupled to a base unit to provide real-time feedback of patient oxygen and carbon dioxide, respectively. The use of external monitoring devices in combination with the controller to provide adaptive control or closed-loop feedback to the system is also described in U.S. patent application Ser. No. 16/722,722, filed Dec. 20, 2019, and entitled "OXYGEN MIXING AND DELIVERY"; U.S. application Ser. No. 16/008,508 (now U.S. Pat. No. 10,514,662), filed Jun. 8, 2018, and entitled "OXYGEN MIXING AND DELIVERY"; and U.S. patent application Ser. No. 14/602,392 (now U.S. Pat. No. 10,007,238), filed Jan. 22, 2015, and entitled "OXYGEN MIXING AND DELIVERY", the entire contents of which are incorporated herein by reference.

Figure 12:
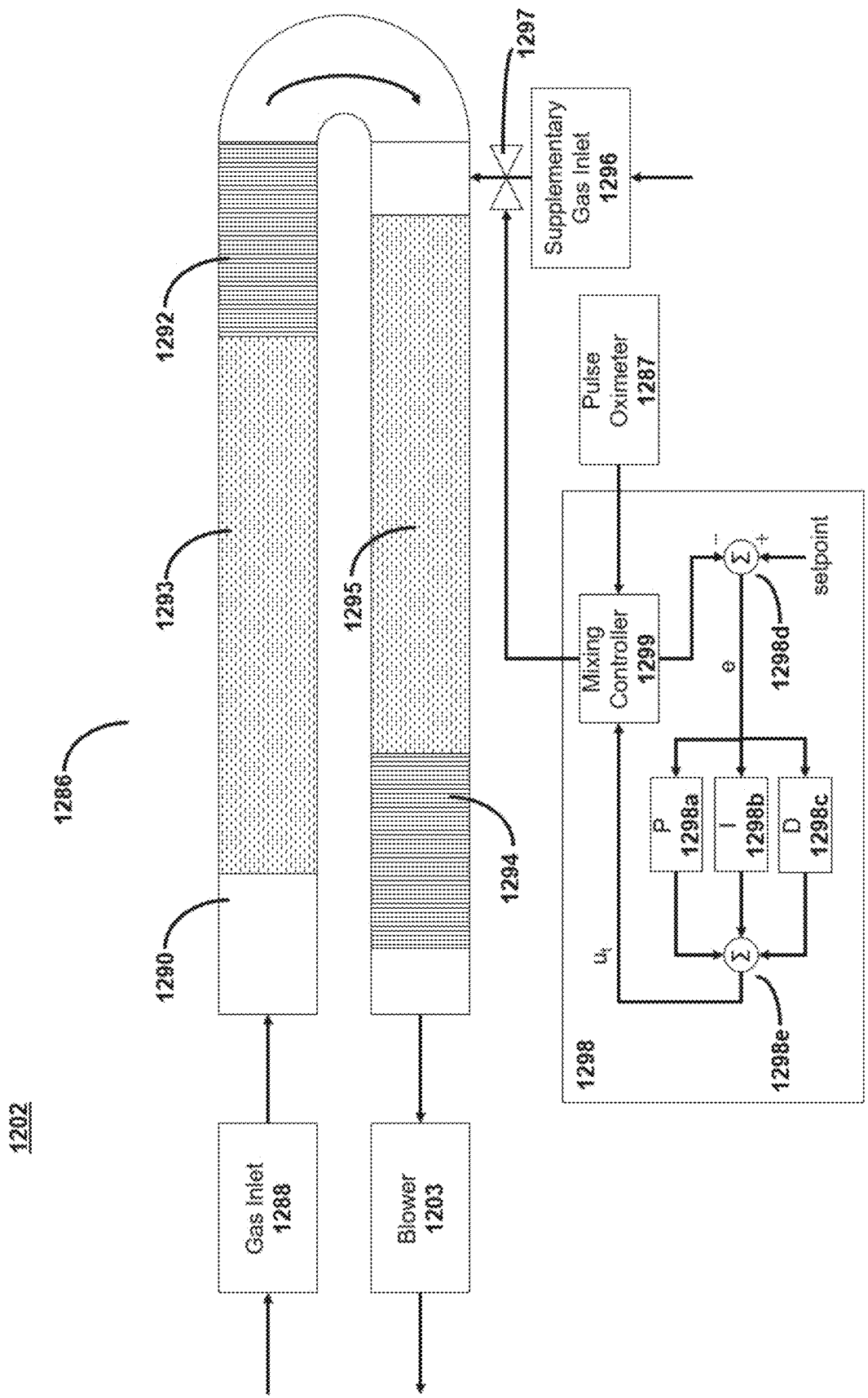
FIG. 12 shows a measurement device configured to receive a supplementary gas and coupled to a PID controller, according to an illustrative implementation.

FIG. 12 depicts a measurement device 1286 configured to receive breathing gas from gas inlet 1288 and supplementary gas from supplementary gas inlet 1296 via supplementary valve 1297, according to an illustrative implementation. Measurement device 1286 includes a conduit 1290 coupled to gas inlet 1288 and a blower 1203. A first flow sensor 1292 and a second flow sensor 1294 are disposed along conduit 1290. Conduit 1290 includes first segment 1293 and second segment 1295. Supplementary gas inlet 1296 is in fluid communication with conduit 1290 via supplementary valve 1297. Base unit 1202 includes a controller 1298 operatively coupled to valve 1297. Controller 1298 includes a mixing controller 1299, a proportional module 1298a, an integral module 1298b, a derivative module 1298c, an error module 1298d, and an output module 1298e. Mixing controller 1299 is coupled to supplementary valve 1297 and a pulse oximeter 1287.

Gas inlet 1288, conduit 1290, first flow sensor 1292, second flow sensor 1294, first segment 1293, second segment 1295, and blower 1203 may be the same as the corresponding components in FIGS. 10 and 11. Like measurement device 1186 of FIG. 11, measurement device 1286 allows for introduction of a supplementary gas from supplementary gas inlet 1296 via supplementary valve 1297 which is operatively coupled to controller 1298. In this implementation, pulse oximeter 1287 is configured to output to controller 1298 data indicative of a percentage of oxygen saturation ($SpO_2$) of a patient's blood. "$SpO_2$" is an acronym for "saturation of peripheral oxygen," and within the related technology, the term $SpO_2$ is often casually referred to as "blood oxygen", "blood oxygen saturation", and other similar terms. Some implementations herein use $SpO_2$ as an estimation of blood oxygen concentration and is usually measured with a pulse oximeter. A pulse oximeter is generally a photoelectric device that measures the amount of saturated hemoglobin in tissue capillaries by transmitting beams of light through the tissue to a light receiver. A pulse oximeter is generally configured so as to clip onto a fingertip or earlobe. The amount of saturated hemoglobin affects the wavelength and reflection or transmission of the light transmitted through the tissue. By analyzing the received light, $SpO_2$ may be deduced. Pulse oximeters may also allow for measurement of a pulse and generating various alarm condition signals. While photoelectric pulse oximeters have been described here, it is to be understood that other types of pulse oximeters may be substituted for pulse oximeter 1287.

In some implementations, controller 1298 is configured to actuate valve 1297 via mixing controller 1299 based on data from pulse oximeter 1287. Controller 1298 may also receive a target SpO$_2$ as an input, for example, via a computer interface or a display such as a display 430 of FIG. 4 which allows for user interaction. A target SpO$_2$ may also be stored in a memory (not shown). Controller 1298 may be configured to compare a measured SpO$_2$ from pulse oximeter 1287 with the target SpO$_2$ and determine an appropriate change in supplementary gas flowrate. For example, the comparison may reveal that the measured SpO$_2$ is below the target SpO$_2$, and the controller may calculate a target supplementary gas flowrate that would raise the patient's SpO$_2$ to the target SpO$_2$. The target supplementary gas flowrate may be implemented by actuating valve 1297 and calculating a difference in flowrate between a first flow measurement from first flow sensor 1292 and a second flow measurement from second flow sensor 1294, because the supplementary gas is introduced between first and second flow sensors 1292 and 1294. Controller 1298 may then further adjust valve 1297 if the calculated flowrate difference is different from the target supplementary gas flowrate.

Controller 1298 may be configured to adjust the flowrate of supplementary gas through valve 1297 in order to set an oxygen concentration in the mixed flow to a minimum oxygen concentration that is determined to have a therapeutic effect on the patient based on data received from pulse oximeter 1287. This capability may be especially advantageous when supplementary gas is supplied from an external tank that has a limited capacity. Controller 1298 may minimize the amount of supplementary gas needed in order to maximize the lifetime of the external tank, providing effective respiratory therapy to a patient for as long as possible given the constraint. Controller 1298 may generate for display one or more graphics indicative of the SpO$_2$, PaO$_2$, or FiO$_2$.

Controller 1298 includes various components allowing for proportional-integral-derivative (PID) control of the breathing gas and supplementary gas. PID controller 1298 allows for feedback-based control of various system parameters, such as the breathing gas flowrate, supplementary gas flowrate, and pump flowrate. Similar configurations are described in U.S. patent application Ser. No. 16/722,722, filed Dec. 20, 2019, and entitled "OXYGEN MIXING AND DELIVERY"; U.S. application Ser. No. 16/008,508 (now U.S. Pat. No. 10,514,662), filed Jun. 8, 2018, and entitled "OXYGEN MIXING AND DELIVERY"; and U.S. patent application Ser. No. 14/602,392 (now U.S. Pat. No. 10,007,238), filed Jan. 22, 2015, and entitled "OXYGEN MIXING AND DELIVERY". The entire contents of the above-referenced applications are incorporated herein by reference. A PID controller is a control loop feedback controller. A PID controller calculates an error value as the difference between a measured process variable and a desired value of the process variable (or set point). The controller operates to minimize the difference between the measured value and the set point. A PID controller accomplishes this by use of an algorithm that uses three separate parameters—proportional (P), integral (I), and derivative (D) values interpreted at discrete increments of time where P depends on the current error, I depends of the accumulation of past errors, and D predicts future errors. The weighted sum of these three actions is used to adjust a process-in this case the proportion of oxygen represented by FiO$_2$. Mathematically, these values are generally represented by the following equations:

$$P = K_p e(t) \qquad \text{Eq. 1}$$

$$I = K_i \int_0^\tau e(\tau) d\tau \qquad \text{Eq. 2}$$

$$D = K_d \frac{de(t)}{dt} \qquad \text{Eq. 3}$$

where a mixing control signal is derived from the PID controller output u$_t$:

$$u_t = P + I + D = K_p e(t) + K_i \int_0^\tau e(\tau) d\tau + K_d \frac{de(t)}{dt} \qquad \text{Eq. 4}$$

and where:
- K$_p$: proportional gain coefficient;
- K$_i$: integral gain coefficient;
- K$_d$: derivative gain coefficient;
- e: error, difference between measurement and target;
- t: time; and
- τ: integration variable, takes on values from time t=0 to present time t.

For purposes of this document, a controller may be referenced as a PID controller for convenience and by way of example, but in practice the controller may in fact not use all three of the elements of proportional, integral, and derivative control. Use of only one or two of the PID control functions is common and use of other feedback control mechanisms is also within the scope of the present teachings. For example, in other example implementations, a PI controller (proportional-integral) or other suitable feedback controller could alternatively be used.

In this aspect, controller 1298 includes modules for each PID control parameter. Module 1298a uses Eq. 1 for proportional control, module 1298b uses Eq. 2 for integral control, and module 1298c uses Eq. 3 for derivative control. The current value of PaO$_2$ (representing the measured SpO$_2$ from pulse oximeter 1287) is received by mixing controller 1299 and subtracted from the setpoint (i.e., the target value) at error module 1298d to produce the error signal e at the output of error module 1298d. This error signal e is then processed by the P, I, and D modules 1298a, 1298b, and 1298c, respectively, according to equations 1-3 above. The outputs of modules 1298a, 1298b, and 1298c are summed at output module 1298e to produce output u$_t$ which is provided to mixing controller 1299. Mixing controller 1299 processes output u$_t$ into an appropriate format to effect control of supplementary valve 1297 to establish an appropriate blend of breathing gas and supplementary gas dictated by PID controller 1298.

An example PID controller equation that may be used for this application is:

$$PaO_2 = (KL * FiO_2) + K2 \qquad \text{Eq. 5}$$

where KL is the lung function gain coefficient relating to the lung's ability to efficiently transfer oxygen and carbon dioxide. K2 is the offset relating to level of overall respiratory capability of a patient. Controller 1298 may use a relatively long sample period, for example, about 10 seconds, which serves as a type of low-pass filter to ensure accuracy of SpO$_2$ calculated from pulse oximeter 1287. Another type of low-pass filter can be provided by using, for example, 90% of old data (from a prior sample period) and adding in, for example, 10% of the new data (from a new sample period). Both filters enhance controller performance so that it is more responsive but not overly responsive.

Controller 1298 may also use an "initial" value of $O_2$ upon initiation of adaptive control. The initial value may be set by a user or operator and is used by controller 1298 to ensure the system starts in a relatively steady-state condition, for example, to avoid having PID control adjusting the patient's $O_2$ level up and down upon start-up.

To ensure the system starts operation in a steady-state condition, the system may be initialized using an initial KL calculated by:

$$KL_i = (PaO_2)_i/(FiO_2)_i \qquad \text{Eq. 6}$$

where $KL_i$, $(PaO_2)_i$, and $(FiO_2)_i$ are all initial values. Furthermore, within each sample period, controller 1298 may use an adaptation algorithm to form new PID gain coefficients. An example algorithm is:

$$KL_{new} = 0.9*KL_{old} + 0.1*(PaO_2/FiO_2) \qquad \text{Eq. 7}$$

where $KL_{new}$ may be used for calculating new PID gain coefficients.

Pulse oximeter 1287 measures $SpO_2$; however, controller 1298 may use $PaO_2$ for its calculations. The term "$PaO_2$" means partial pressure of arterial oxygen. Although, in other implementations, control signals may be more directly derived from $SpO_2$ or other measures of a patient's blood oxygen concentration without limitation. Conversion of $SpO_2$ to $PaO_2$ may be effected in a number of ways. In one example, measured $SpO_2$ is converted into the correlating partial pressure of arterial oxygen $PaO_2$ by using an oxyhemoglobin dissociation curve based on standard conditions of temperature equal to 37° C., pH equal to 7.4, and the Bohr effect is not present. The dissociation curve plots $PaO_2$ against $SpO_2$, allowing one to read the value of $PaO_2$ off the graph based on a known value of $SpO_2$. Oxyhemoglobin dissociation curves may be shifted to the left due to conditions causing high $O_2$ affinity and to the right due to conditions causing low $O_2$ affinity. The curve generally approximates a sigmoidal shape and various equations can be devised to closely model the shape of the curve using various curve fitting techniques. Using such equations, the value of $PaO_2$ may be calculated directly. Alternatively, data points from the dissociation curve can be cataloged into a lookup table stored in a storage or memory (not shown) which can be used by mixing controller 1299 to convert the value of $SpO_2$ to a value of $PaO_2$. If the exact value of $SpO_2$ is not on the table, then a linear or non-linear interpolation (any suitable interpolation such as polynomial, piecewise, spline, bilinear, extrapolation, etc.) can be performed to approximate the corresponding value of $PaO_2$. The more data points provided in the lookup table, the more accurate the interpolation, if necessary, will be.

An example workflow for adaptive control is as follows. Mixing controller 1298 receives pulse oximeter data from pulse oximeter 1287. The pulse oximeter data includes $SpO_2$ data and alarm condition signals. From the $SpO_2$ data, mixing controller 1299 determines $PaO_2$ data for calculation of an appropriate oxygen concentration of the mixed flow output to the patient. The $PaO_2$ data may be determined by referencing a stored lookup table, using interpolation if necessary, where the lookup table may be derived from an oxyhemoglobin dissociation curve. Controller 1298 and its components 1298*a-e* effect adaptive feedback control of the gas based on the $SpO_2$ data by mixing controller 1298 interfacing with valve 1297. Adaptive feedback control is provided by the PID control scheme. Controller 1298 may receive flowrate data or a flowrate signal indicating that the breathing gas delivered out of conduit 1290 has been manually changed. This flowrate data may be received from a user interface, such as a display like display 430 of FIG. 4, or from first or second flow sensors 1292 and 1294. Upon receiving the flowrate data or flowrate signal, controller 1298 may enter a manual override mode and halt adaptive feedback control (i.e. halt sending signals to valve 1297). Controller 1298 may be configured to compare measured $SpO_2$ data with alarm limits and initiate an alarm condition if the measured $SpO_2$ data is outside the alarm limits. An alarm condition may involve halting operation of base unit 1202 and/or generating for display an alert for the user (e.g., on a display like display 430 of FIG. 4).

Another example workflow involves mixing controller 1299 receiving pulse oximeter data from pulse oximeter 1287. The pulse oximeter data includes one or more signals indicative of a current blood oxygen level of the patient. Controller 1298 receives from first flow sensor 1292 and second flow sensor 1294 gas data indicative of measured breathing gas flowrates. The measured breathing gas flowrates may be subtracted to determine an amount of supplementary gas added between first and second flow sensors 1292 and 1294. Controller 1298 may calculate a concentration of oxygen (percentage oxygen) in the mixed flow (breathing gas and supplementary gas) based on the calculated added amount and the second measured breathing gas flowrate. Controller 1298 compares the one or more current blood oxygen level signals to a target blood oxygen level. The target may be stored in a memory in base unit 1202 or inputted by a user via a user interface. Controller 1298 calculates an appropriate change to the mixed flow to achieve a change in the oxygen concentration in the mixed flow. Mixing controller 1299 actuates valve 1297 to alter the oxygen concentration in the mixed flow (e.g., by increasing or decreasing supplementary gas flowrate, the supplementary gas possibly containing oxygen). Mixing controller 1299 may receive new signals from pulse oximeter 1287 indicative of a current blood oxygen level of the patient.

In some implementations, a transcutaneous carbon dioxide sensor is coupled to controller 1298 of base unit 1202, and the transcutaneous carbon dioxide sensor is configured to output to controller 1298 one or more signals indicative of $PaCO_2$. Transcutaneous carbon dioxide sensors generally measure the skin-surface partial pressure of carbon dioxide ($PtcCO_2$) to provide an estimate of the partial pressure of arterial carbon dioxide ($PaCO_2$). In some cases, both the sensor also measures partial pressure of oxygen (PtcO2) to estimate the partial pressure of arterial oxygen ($PaO_2$). Controller 1298 may be configured for closed-loop control of patient carbon dioxide based on the received signals, using the methods previously described for closed-loop oxygen control.

Using a sensor that measures both $PtcCO_2$ and $PtcO_2$, or using both a pulse oximeter and a transcutaneous carbon dioxide sensor, controller 1298 may be configured to receive both oxygen and carbon dioxide data and determine an appropriate therapy for the patient based on the received data. For example, controller 1298 may compare the measured oxygen data and the measured carbon dioxide data to a stored reference table which includes at least one reference oxygen value and at least one reference carbon dioxide value. Controller 1298 may compute differences between a current blood oxygen level and a reference oxygen level and between a current blood carbon dioxide level and a reference carbon dioxide level. Controller 1298 may be configured to determine to provide the patient with a high oxygen therapy (e.g., to increase blood oxygen levels) or a high flush therapy (e.g., to decrease blood carbon dioxide levels). For example, if the blood oxygen level difference is greater than the carbon dioxide level difference, controller 1298 may select the high oxygen therapy, or if the blood carbon dioxide level difference is greater than the oxygen level difference, controller 1298 may select the high flush therapy. Upon selecting high oxygen therapy, controller 1298 may direct mixing controller 1299 to actuate valve 1297 to increase the flowrate of supplementary gas into conduit 1290, for example, in cases where the supplementary gas contains a higher oxygen concentration than the breathing gas from gas inlet 1288. Upon selecting high flush therapy, controller 1298 may increase the breathing gas flowrate through gas inlet 1288 by, for example, increasing a suction pressure of blower 1203. Providing high flush therapy may involve increasing an output pressure or output flowrate of blower 1203.

Use with Aerosolized Medications

The systems described herein, including systems 100, 400, 500, 600, and 800 of FIGS. 1, 4-6, 8A, and 8B, may comprise or may be configured to connect to a device configured to produce aerosolized medication. For example, these systems include a nebulizer or aerosolizer. Liquid medicaments that are to be administered via inhalation may be aerosolized and introduced into the breathing gas supplied by these systems before being delivered to a patient. This configuration allows for treatment of some respiratory diseases by delivering breathing gas with entrained aerosolized medicament which is breathed in for direct transport to the lungs.

A nebulizer (pneumatic, mechanical, or electrical) may be connected at certain points in the system. For example, a delivery tube of the system, such as delivery tubes 406 and 706 of FIGS. 4 and 6, includes a port configured to attach a nebulizer, from which aerosolized medicament enters the delivery tube and becomes entrained in breathing gas flow. As another example, a patient connector or nasal cannula configured to the end of the delivery tube includes a port configured to attach the nebulizer. In other implementations, an auxiliary unit, such as auxiliary units 404, 504, 604, 704, 804, and 904 of FIGS. 4-9, includes a port configured to attach the nebulizer, from which aerosolized medicament enters the auxiliary unit and becomes entrained in breathing gas flow. In some implementations, the aerosol is introduced into the breathing gas before the breathing gas enters a vapor transfer unit for humidification. In other implementations, the aerosol is introduced into the breathing gas after the breathing gas is humidified by the vapor transfer unit. The system may be configured to adjust the vaporization rate in the vapor transfer unit based on the amount of aerosol entrained in the breathing gas, by monitoring the aerosol flow rate via a flow sensor or level sensor in the nebulizer or a flow sensor in the port or auxiliary unit.

An RFID tag or other tag, chip, or sensor in the auxiliary unit may store information about the type of nebulizer or medication to be introduced via the nebulizer. In some implementations, high viscosity fluids (i.e., >6 cP) are used in the nebulizer to be aerosolized and subsequently entrained. The RFID tag may be read, and the stored information is transmitted to a controller in the base unit. Based on the information, the controller may adjust the vaporization rate or heating rate in the auxiliary unit. The controller may also be operatively coupled to the nebulizer and use the information to adjust operation of the nebulizer. For example, if it is indicated that a high viscosity fluid will be nebulized, the controller adjusts the vibration frequency, pressure, force, or other parameter of the nebulizer to account for the high viscosity.

Methods of Treatment

Provided herein are systems and methods for respiratory therapy. In some aspects, these systems and methods are used to treat certain respiratory diseases or conditions. Operation of the systems provided herein may be attuned for the specific respiratory disease or condition being treated. For example, certain supplementary gases or aerosolized medicament is used for treatment of certain conditions.

In some implementations, the systems described herein are used for the treatment of coronavirus disease 2019 (COVID-19), caused by severe acute respiratory syndrome coronavirus 2 (SARS-COV-2). These systems configured with a high flow nasal cannula may be used for mechanical ventilation of patients with COVID-19 related respiratory failure. In some implementations, this form of therapy, using a high flow nasal cannula and the system parameters described in Table 1 or Table 2, can be performed without intubation. In some implementations, this method of treatment further utilizes a face mask to reduce the spread of aerosol particles or contaminants exhaled by the patient. Treatment of COVID-19 may involve introducing supplementary oxygen into the breathing gas via a supplementary gas inlet (e.g., supplementary gas inlets 1196 and 1296 of FIGS. 11 and 12). A pulse oximeter may be attached to the patient during treatment, such that $SpO_2$ is monitored and the flowrate of supplementary oxygen can be adjusted to provide enough oxygen to reach a therapeutic level of oxygen in the patient.

Mobile Use

The systems and methods described herein may be used in a mobile configuration. Systems 100, 400, 500, 600, and 800 of FIGS. 1, 4-6, 8A, and 8B can be used at home, in a vehicle, on a mobile platform or cart, or in a backpack. The systems and methods, using a blower, are configured to receive and pressurize ambient air, so they can operate without need of an external gas source like wall air or pressurized tanks. Furthermore, the systems and methods are configured to operate on battery power, so they do not require an external power source like an electrical outlet or generator. The battery has enough capacity to provide heated and humidified respiratory therapy for hours, e.g., >8 hours, >6 hours, >4 hours, >2 hours, >1 hour. For example, the respiratory therapy systems are configured on a rolling cart allowing a patient to move throughout their home or a hospital while receiving respiratory therapy from the system moving with them.

In another example, a patient in a vehicle (e.g., a personal vehicle, an ambulance, or a helicopter) receives respiratory therapy via a specific auxiliary unit (or a patient circuit including the specific auxiliary unit, delivery tube, and patient connector or nasal cannula) configured to a first base unit. Upon arriving at a medical facility, the specific auxiliary unit is removed from the first base unit. As discussed in the foregoing, the base unit may be configured to automatically stop operation when the auxiliary unit is removed. The first base unit remains in the vehicle, while the auxiliary unit is transported with the patient into the facility. The specific auxiliary unit may then be re-docked into a second base unit in the medical facility, resuming respiratory therapy via the second base unit. The second base unit must be set up again with the correct therapy and started up, consuming valuable time.

To hasten startup time of the second base unit, the auxiliary unit may comprise an RFID tag, as discussed above, that stores the previous operating conditions from when the auxiliary unit was used in the vehicle with the first base unit. The RFID tag may have data written to it by the first base unit. The data may indicate that the auxiliary unit was actively treating the patient and what therapy was being given. Upon re-docking in the second base unit, a reader in the second base unit reads the RFID tag, sending the data or information indicative of the previous therapy or operating conditions to the controller of the second base unit. The controller then sets parameters to match the previous operating conditions, allowing the patient to resume the same respiratory therapy. The same auxiliary unit is used for the patient, allowing the patient to be transferred from transport to the facility without replacing the auxiliary unit.

The data stored on the RFID tag may indicate: that the auxiliary unit was providing therapy, the time at which therapy was interrupted, the settings of the therapy (e.g., breathing gas flow rate, temperature, oxygen concentration, humidity, pump power, heating rate, valve settings), the state of the patient circuit (e.g., the actual temperature of the breathing gas as compared to a set point temperature), and patient data (e.g., age, height, weight, disease type, disease status, concomitant disease, concomitant therapy). Data may be stored continuously, such that ejecting the auxiliary unit from the base unit results in the latest settings being stored. In some implementations, the RFID tag has limited data storage or write operations, so the past data is overwritten with current data. An operator may initiate the write operation prior to stopping therapy, or the controller may be configured to automatically write the data upon receiving a user command to stop operation. The controller may be configured to include a switch that stores the data and prompts the user to remove the device. In some implementations, data is stored whenever setting are changed, storing the last known settings. Upon re-docking of the auxiliary unit, the controller of the second base unit may be configured to generate for display a prompt to the user to resume therapy if desired. In some implementations, the therapy has lapsed for an extended time or the actual temperature was lower than the set point, so the second base unit operates the heating elements to warm up the auxiliary unit before resuming therapy.

The first base unit used in transport may have limited functions, for example, without some or all of the following features: liquid heating, liquid circulation, full range of flow rates, full range of oxygen therapy, liquid level sensing, valve control, and user interface/display. The base unit may include features that provide the minimum therapy needed for the specific patient or specific transport operation. The auxiliary unit may be corresponding limited to function with only the features which the first base unit is limited to. Removing some of the features from the first base unit for transport allows for extended operation on battery power or low-power mode and for a more compact unit. When re-docking the auxiliary unit in the second base unit, if the first base unit is lacking certain features, the user may be prompted to adjust the settings appropriately.

Example of High Flow Therapy

Figure 13A:
FIGS. 13A and 13B show a graphical representations of carbon dioxide in a patient's airway during high flow therapy, according to an illustrative implementation.
Figure 13B:

FIGS. 13A and 13B show graphical representations (contour plots) of simulated amounts of carbon dioxide in a patient's airway during high flow therapy, according to an illustrative implementation. In these implementations, a blower-based respiratory therapy system is used, such as systems 100, 400, 500, 600, and 800 of FIGS. 1, 4-6, 8A, and 8B. A nasal cannula transfers breathing gas from the system into a nare of the patient. In both FIGS. 13A and 13B, the breathing gas flowrate through nasal cannula is 40 L/min, and the patient is breathing at 24 breaths per minute. The amount of $CO_2$ present in the patient's airway is captured in the contour plots when the patient is at peak expiratory flow, the maximum flowrate they reach during exhalation. Darker regions indicate a higher percentage of $CO_2$, and lighter regions indicate a lower percentage of $CO_2$.

The simulations differ in that FIG. 13A uses a large bore cannula, and FIG. 13B uses a small bore cannula. Using the large bore cannula (specifically having a 4.13 mm inner diameter), simulated in FIG. 13A, high flow therapy results in a large percentage $CO_2$ (up to 0.0486 mass fraction of $CO_2$) in the patient's upper airway. Patients typically rebreathe a third of previously expired tidal volume, where previously exhaled breath (low in oxygen and with some $CO_2$) is not fully exhaled and remains in the upper airway. As patients rebreathe, $CO_2$ in this upper airway reservoir is drawn into the lungs. Patients with acute respiratory failure rebreathe a larger percentage of gas, resulting in rebreathing larger amounts of carbon dioxide as they draw breaths from the upper airway reservoir. Accordingly, it is not desirable for the patient to have larger percentages of $CO_2$ in the reservoir, especially when higher amounts of oxygen are needed for a therapeutic effect.

FIG. 13B shows $CO_2$ percentages based on simulation of high flow therapy with a small bore cannula, specifically having a 2.64 mm inner diameter in accordance with the parameters of row 3 of Table 1 or row 3 of Table 2. Use of the small bore cannula, at otherwise the same operational parameters, leads to lower percentages of $CO_2$ in the patient's upper airway compared to the large bore cannula implementation. Continuous high flow therapy with the small bore cannula washes out the upper airway, because the smaller inner diameter of the nasal cannula prong induces a higher exit velocity of gas when operating at the same volumetric flowrate. A continuous high flow of fresh gas with this higher exit velocity, the upper airway of the patient is washed out, effectively creating a reservoir of oxygen in the upper airway (pharyngeal dead space) available for gas exchange during rebreathing. In this implementation, rebreathing of $CO_2$ is avoided, instead replacing $CO_2$ with oxygen-rich gas and improving breathing efficiency.

The foregoing is merely illustrative of the principles of the disclosure, and the apparatuses can be practiced by other than the described implementations, which are presented for purposes of illustration and not of limitation. It is to be understood that the apparatuses disclosed herein, while shown for use in high flow therapy systems, may be applied to systems to be used in other ventilation circuits.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

ILLUSTRATIVE EMBODIMENTS

A1. A system for providing respiratory therapy to a patient, the system comprising:
    a blower configured to:
        receive breathing gas from ambient air, a tank, or a wall outlet; and
        output pressurized breathing gas;

a conduit in fluid communication with the blower, wherein the conduit receives the breathing gas from the blower; and a nasal cannula having at least one nasal prong, the nasal cannula being in fluid communication with the conduit and configured to receive the breathing gas from the conduit, the at least one nasal prong being configured to provide the breathing gas to a nare of the patient;

wherein the nasal prong is configured to provide breathing gas at an exit velocity of at least about 40 m/s and less than about 75 m/s.

A2. The system according to A1, wherein the nasal prong has an inner diameter greater than or equal to about 1.4 mm and less than about 1.8 mm, and the system has a maximum flow setpoint greater than or equal to about 9 L/min and less than about 28 L/min.

A3. The system according to A1, wherein the at least one nasal prong has an inner diameter greater than or equal to about 1.8 mm and less than about 1.9 mm, and the system has a maximum flow setpoint greater than or equal to about 13 L/min and less than about 31 L/min.

A4. The system according to A1, wherein the at least one nasal prong has an inner diameter greater than or equal to about 1.9 mm and less than about 3 mm, and the system has a maximum flow setpoint greater than or equal to about 21 L/min and less than about 60 L/min.

A5. The system according to A1, wherein the at least one nasal prong has an inner diameter greater than or equal to about 3 mm and less than about 4 mm, and the system has a maximum flow setpoint greater than or equal to about 34 L/min and less than about 80 L/min.

A6. The system according to A1, wherein the at least one nasal prong has an inner diameter greater than or equal to about 1.1 mm and less than about 1.6 mm, and the nasal cannula has a pressure drop less than about 80 hPa when operating at a maximum flow setpoint of about 8 L/min.

A7. The system according to A1, wherein the at least one nasal prong has an inner diameter greater than or equal to about 1.5 mm and less than about 2 mm, and the nasal cannula has a pressure drop less than about 100 hPa when operating at a maximum flow setpoint of about 20 L/min.

A8. The system according to A1, wherein the at least one nasal prong has an inner diameter greater than or equal to about 1.9 mm and less than about 3.5 mm, and the nasal cannula has a pressure drop less than about 80 hPa when operating at a maximum flow setpoint of about 40 L/min.

A9. The system according to any of A1-A8, further comprising a controller and a processor configured to:
receive first data indicative of one or more dimensions of the nasal cannula;
receive second data indicative of a flowrate of breathing gas; and
calculate the exit velocity based on the first data and the second data.

A10. The system according to A9, further comprising a display, and wherein the processor is further configured to generate for display at least one of: the flowrate, the exit velocity, a maximum flow setpoint, and a pressure drop.

A11. The system according to any of A9 and A10, wherein the blower, controller, and processor are housed in a base unit, the system further comprising an attachable unit configured to reversibly connect to the base unit.

A12. The system according to A11, wherein the conduit is configured to reversibly connect to the attachable unit, wherein the nasal cannula is configured to reversibly connect to the conduit, and wherein the processor receives the first data when the attachable unit is connected to the base unit.

A13. The system according to A12, wherein the processor receives the first data from an RFID tag within the attachable unit.

A14. The system according to A9, wherein the first data comprises an inner diameter of the at least one nasal prong.

A15. The system according to A9, wherein the processor is configured to identify the nasal cannula based on the first data.

A16. The system according to any of A9-A15, further comprising at least one sensor configured to measure the flowrate of breathing gas and send the second data to the processor.

A17. The system according to any of A9-A16, wherein the processor is further configured to receive a user input to change at least one of:
the flowrate of breathing gas to a modified flowrate of breathing gas, or
the exit velocity to a modified velocity.

A18. The system according to A17, wherein the controller is configured to change the flowrate of breathing gas to the modified flowrate based on the user input.

A19. The system according to any of A17 and A18, wherein the processor is further configured to calculate a modified velocity based on the modified flowrate and the first data.

B1. A method for providing respiratory therapy to a patient, the method comprising:
outputting a flow of breathing gas from a blower through a conduit and into a nasal cannula; and
providing the breathing gas to a nare of the patient from at least one nasal prong of the nasal cannula, the nasal cannula being in fluid communication with the conduit and configured to receive the breathing gas from the conduit;
wherein the at least one nasal prong is configured to provide breathing gas from a distal end of the at least one nasal prong at an exit velocity of at least about 40 m/s and less than about 75 m/s.

B2. The method according to B1, wherein the at least one nasal prong has an inner diameter greater than or equal to about 1.4 mm and less than about 1.8 mm, and the blower has a maximum flow setpoint greater than or equal to about 9 L/min and less than about 28 L/min.

B3. The method according to B1, wherein the at least one nasal prong has an inner diameter greater than or equal to about 1.8 mm and less than about 1.9 mm, and the blower has a maximum flow setpoint greater than or equal to about 13 L/min and less than about 31 L/min.

B4. The method according to B1, wherein the at least one nasal prong has an inner diameter greater than or equal to about 1.9 mm and less than about 3 mm, and the blower has a maximum flow setpoint greater than or equal to about 21 L/min and less than about 60 L/min.

B5. The method according to B1, wherein the at least one nasal prong has an inner diameter greater than or equal to about 3 mm and less than about 4 mm, and the blower has a maximum flow setpoint greater than or equal to about 34 L/min and less than about 80 L/min.

B6. The method according to B1, wherein the at least one nasal prong has an inner diameter greater than or equal to about 1.1 mm and less than about 1.6 mm, and the nasal cannula has a pressure drop less than about 80 hPa when the blower operates at a maximum flow setpoint of about 8 L/min.

B7. The method according to B1, wherein the at least one nasal prong has an inner diameter greater than or equal to about 1.5 mm and less than about 2 mm, and the nasal cannula has a pressure drop less than about 100 hPa when the blower operates at a maximum flow setpoint of about 20 L/min.

B8. The method according to B1, wherein the at least one nasal prong has an inner diameter greater than or equal to about 1.9 mm and less than about 3.5 mm, and the nasal cannula has a pressure drop less than about 80 hPa when the blower operates at a maximum flow setpoint of about 40 L/min.

B9. The method according to any of B1-B8, further comprising:
receiving first data indicative of one or more dimensions of the nasal cannula;
receiving second data indicative of a flowrate of breathing gas; and
calculating the exit velocity based on the first data and the second data.

B10. The method according to B9, further comprising:
generating for display at least one selected from the group of: the flowrate, the exit velocity, a maximum flow setpoint, and a pressure drop.

B11. The method according to any of B9 and B10, comprising:
generating for display the flowrate and the exit velocity.

B12. The method according to any of B9-B11, further comprising:
receiving a user input to increase or decrease the flowrate of the breathing gas;
changing the flowrate to a modified flowrate of the breathing gas;
calculating a modified velocity based on the modified flowrate and the first data; and
generating for display at least one selected from the group of: the modified flowrate and the modified velocity.

C1. The system or method according to any of A1-A19 and B1-B12, wherein the breathing gas is configured to be humidified and heated.

C2. The system or method according to any of A1-A19 and B1-B12, wherein the exit velocity is at least about 40 m/s and less than about 70 m/s.

C3. The system or method according to any of A1-A19 and B1-B12, wherein the exit velocity is at least about 40 m/s and less than about 65 m/s.

C4. The system or method according to any of A1-A19 and B1-B12, wherein the exit velocity is at least about 40 m/s and less than about 60 m/s.

C5. The system or method according to any of A1-A19 and B1-B12, wherein the exit velocity is at least about 40 m/s and less than about 55 m/s.

C6. The system or method according to any of A1-A19 and B1-B12, wherein the exit velocity is at least about 40 m/s and less than about 50 m/s.

C7. The system or method according to any of A1-A19 and B1-B12, wherein the exit velocity is at least about 40 m/s and less than about 45 m/s.

C8. The system or method according to any of A1-A19 and B1-B12, wherein the exit velocity is about 40 m/s.

D1. A system for providing respiratory therapy to a patient, the system comprising:
a base unit comprising:
a blower configured to output breathing gas; and
a controller;
an auxiliary unit configured to be reversibly coupled to the base unit, wherein the auxiliary unit comprises an auxiliary unit outlet; and
a delivery tube configured to receive the breathing gas from the auxiliary unit outlet and transmit the breathing gas to the patient.

D2. The system according to D1, wherein the base unit further comprises a measurement device comprising:
a first flow sensor,
a second flow sensor, and
a device conduit in fluid communication with the blower,
wherein the first flow sensor and second flow sensor are positioned in series along the conduit.

D3. The system according to D2, wherein the device conduit is configured to:
receive breathing gas from a gas inlet of the base unit;
direct the breathing gas through the first flow sensor, wherein the first flow sensor is configured to output a first measurement of the breathing gas;
direct the breathing gas through the second flow sensor, wherein the second flow sensor is configured to output a second measurement of the breathing gas; and
output the breathing gas to the blower.

D4. The system according to D3, wherein the controller is configured to set a breathing gas flowrate of the blower based on at least one of the first measurement or the second measurement.

D5. The system according to any of D2-D4, wherein the first flow sensor and the second flow sensor are mass flow sensors.

D6. The system according to any of D2-D5, wherein the first flow sensor and the second flow sensor are each configured to be calibrated relative to the other.

D7. The system according to any of D2-D6, wherein the device conduit comprises a first segment configured to direct the breathing gas through the first flow sensor and a second segment configured to direct the breathing gas through the second flow sensor, wherein the first segment and the second segment are approximately straight.

D8. The system according to any of D2-D7, wherein the system comprises a supplementary gas inlet configured to receive a supplementary gas from an external gas source and add the supplementary gas to the breathing gas, wherein the supplementary gas inlet is in fluid communication with the device conduit and disposed between the first flow sensor and the second flow sensor.

D9. The system according to D8, further comprising a supplementary valve configured to control of flow of the supplementary gas through the supplementary gas inlet.

D10. The system according to D9, wherein the supplementary valve is a solenoid valve.

D11. The system according to any of D9 and D10, wherein the first flow sensor is configured to output a first measurement of the breathing gas, and wherein the second flow sensor is configured to output a second measurement of a mixture of the breathing gas and the supplementary gas.

D12. The system according to D11, wherein the controller is configured to calculate a flow difference between the first measurement and the second measurement, wherein the flow difference indicates an amount of one or more components of the supplementary gas added to the breathing gas, and wherein the controller is configured to calculate one or more concentrations of the one or more components in the mixture based on the flow difference and the second measurement.

D13. The system according to D12, wherein the controller is configured to operate the supplementary valve to control the added amount based on the calculated flow difference.

D14. The system according to D13, wherein the controller is configured to:
receive as an input a target concentration,
compare the one or more calculated concentrations to the target concentration, and
control the added amount based on the comparison.

D15. The system according to any of D12-D14, wherein the flow difference is less than about 5% of the first measurement.

D16. The system according to D15, wherein the flow difference is less than about 1% of the first measurement.

D17. The system according to any of D8-D16, wherein the external gas source is one selected from the group of: a wall gas outlet, a gas concentrator, and a gas tank.

D18. The system according to any of D8-D17, wherein the supplementary gas is oxygen, oxygen concentrated breathing gas, helium, nitric oxide, heliox, an anesthetic gas, or a gas containing aerosolized medicament.

D19. The system according to any of D8-D18, wherein the controller is configured to operate the supplementary valve to pause the flow of the supplementary gas and to calibrate the first flow sensor and the second flow sensor to each other while the supplementary gas flow is paused, wherein calibrating reduces an error of the calculated flow difference to an error of the second flow sensor.

D20. The system according to any of D8-D19, further comprising:
one or more additional supplementary gas inlets for adding one or more additional supplementary gas; and
one or more additional flow sensors, wherein the device comprises one additional flow sensor for each additional supplementary gas inlet.

D21. The system according to any of D1-D20, wherein the base unit comprises a seat configured to receive the auxiliary unit when the auxiliary unit is coupled to the base unit.

D22. The system according to D21, wherein the base unit comprises at least one alignment sensor, and the auxiliary unit comprises at least one alignment marker.

D23. The system according to D22, wherein the at least one alignment sensor is configured to transmit a first signal to the controller when the at least one alignment marker is aligned with the at least one alignment sensor.

D24. The system according to any of D22 and D23, wherein the at least one alignment sensor is configured to transmit a second signal to the controller when the at least one alignment marker is not aligned with the at least one alignment sensor.

D25. The system according to D24, wherein the controller is configured to halt operation of the system when the controller receives the second signal.

D26. The system according to any of D24 and D25, wherein the controller generates an alarm when the controller receives the second signal.

D27. The system according to D26, wherein the alignment of the at least one alignment marker with the at least one alignment sensor indicates that the auxiliary unit is fully seated in the seat.

D28. The system according to any of D21-D27, wherein the auxiliary unit comprises a spring return configured to eject the auxiliary unit from the seat.

D29. The system according to any of D21-D28, wherein the auxiliary unit comprises at least one tab configured to lock in a recess of the seat.

D30. The system according to any of D22-D29, wherein the at least one alignment marker is a magnet, and the at least one alignment sensor is a Hall effect sensor.

D31. The system according to any of D22-D29, wherein the at least one alignment marker is a RFID tag, and the at least one alignment sensor is a RFID reader.

D32. The system according to D31, wherein the RFID tag comprises information about the auxiliary unit.

D33. The system according to D32, wherein the information includes at least one selected from the group of: a use history of the auxiliary unit, a lifetime of the auxiliary unit, a remaining lifetime of the auxiliary unit, one or more functionalities of the auxiliary unit, embedded licensing, and recommended operating parameters.

D34. The system according to D33, wherein the one or more functionalities is at least one selected from the group of: low flow, high flow, aerosolization, humidification, oxygenation, nitric oxide, helium, and closed loop oxygen control.

D35. The system according to any of D32-D34, wherein the controller is configured to set a range of acceptable flowrates of the breathing gas based on the information.

D36. The system according to any of D1-D35, wherein the base unit further comprises a heat exchanger configured to cool the breathing gas outputted from the blower.

D37. The system according to D36, wherein the heat exchanger is configured to disperse heat radially from the outputted breathing gas.

D38. The system according to any of D36 and D37, wherein the heat exchanger is configured to lower a breathing gas temperature of the outputted breathing gas to a target breathing gas temperature.

D39. The system according to any of D1-D38, wherein the auxiliary unit is configured to be reversibly coupled to the base unit via one or more couplings, at least one coupling of the one or more couplings being configured to allow fluid communication of the breathing gas from the base unit to the auxiliary unit.

D40. The system according to D39, wherein the at least one coupling configured to allow fluid communication is an occluding valve.

D41. The system according to D40, wherein the occluding valve is operatively coupled to the controller, and wherein the occluding valve is configured to simultaneously control the outputted breathing gas and a liquid flow.

D42. The system according to D41, wherein occluding valve is configured to receive the liquid flow from an external liquid supply and direct the liquid flow into the auxiliary unit.

D43. The system according to any of D41 and D42, wherein occluding valve is configured to receive the breathing gas outputted from the blower and direct the breathing gas into the auxiliary unit.

D44. The system according to any of D40-D43, wherein the occluding valve comprises:
- an air path valve seal;
- a bellows; and
- a valve actuator;
- wherein the valve actuator is configured to expand and contract the bellows and raise and lower the air path valve seal.

D45. The system according to D44, wherein the valve actuator is a linearly actuated rod.

D46. The system according to any of D44 and D45, wherein the controller is configured to position the valve actuator in one of at least three actuator positions, and wherein the valve actuator is configured to position the air path valve seal in one of at least three air path positions.

D47. The system according to any of D44-D46, wherein the occluding valve further comprises a gas seal which forms an annular space around the air path valve seal.

D48. The system according to any of D44-D47, wherein the occluding valve further comprises a flexible diaphragm, wherein the air path valve seal actuates the flexible diaphragm to be in one of at least three diaphragm positions by abutting the flexible diaphragm when the air path valve seal is raised by the valve actuator.

D49. The system according to any of D46-D48, wherein the at least three actuator positions include a retracted position, a partially extended position, and a fully extended position.

D50. The system according to D49, wherein the retracted position blocks breathing gas and permits liquid flow, wherein the partially extended position permits both breathing gas and liquid flow through the occluding valve, and wherein the fully extended position permits breathing gas through the occluding valve and blocks liquid flow.

D51. The system according to any of D49 and D50, wherein when the valve actuator is in the fully extended position the flexible diaphragm occludes an outlet of a liquid inlet tube.

D52. The system according to any of D49-D51, wherein the controller is configured to position the valve actuator in the partially extended position or the fully extended position when the controlled receives the first signal.

D53. The system according to any of D49-D52, wherein the controller is configured to position the valve actuator in the retracted position when the controlled receives the second signal.

D54. The system according to any of D49-D53, wherein when the valve actuator is in the retracted position the air path valve seal prevents an ingress of liquid into the base unit.

D55. The system according to any of D1-D54, wherein the auxiliary unit comprises a liquid container and a vapor transfer cartridge (VTC) configured to humidify the breathing gas, wherein the liquid container comprises an outlet conduit in fluid communication with a cartridge inlet of the VTC.

D56. The system according to D55, wherein the base unit comprises a level sensor operatively coupled to the controller and configured to output at least one liquid level measurement indicating a liquid level in the liquid container.

D57. The system according to D56, wherein the controller is configured to calculate an output humidity of the VTC based on the at least one liquid level measurement and at least one flow measurement.

D58. The system according to D57, wherein the controller is configured to adjust the valve actuator based on the output humidity.

D59. The system according to any of D56-D58, wherein the controller is configured to compare the at least one liquid level measurement to a reference liquid level and at least one of generate an alarm or halt operation of the system.

D60. The system according to any of D56-D59, wherein the level sensor is a capacitive sensor.

D61. The system according to any of D1-D60, wherein the auxiliary unit comprises a heating plate in a heating section, and wherein the base unit comprises a heat actuator configured to be operatively coupled to the heating plate and is not in contact with the heating plate.

D62. The system according to D61, wherein the heat actuator is a coil that is configured to induce a current in the heating plate.

D63. The system according to D62, wherein the induced current generates heat in the heating plate due to a resistance of the heating plate.

D64. The system according to any of D61-D63, wherein the heating plate is configured to be immersed in liquid within the auxiliary unit and to heat the liquid.

D65. The system according to any of D61-D64, wherein the heating plate does not contact an external surface of the auxiliary unit.

D66. The system according to any of D61-D65, wherein the heating plate comprises a protruding tab, and wherein the base unit comprises a temperature sensor configured to output a temperature measurement of the protruding tab.

D67. The system according to D66, wherein the controller is configured to receive the temperature measurement and compare the temperature measurement to a reference temperature.

D68. The system according to D67, wherein, based on comparing the temperature measurement to the reference temperature, the controller is configured to at least one of halt operation of the system or generate an alarm.

D69. The system according to any of D61-D68, wherein the heat actuator is configured to operate while the system operates without an external power supply.

D70. The system according to any of D61-D69, wherein the heating plate is orientation specific relative to the heat actuator.

D71. The system according to any of D1-D70, wherein the auxiliary unit comprises a pump configured to pump the liquid in the auxiliary unit.

D72. The system according to D71, wherein the pump comprises a rotor cup, and wherein the base unit comprises a stator configured to be magnetically coupled to the rotor cup.

D73. The system according to any of D71 and D72, wherein the pump is configured to pump the liquid through a liquid loop of the auxiliary unit, wherein a bolus of the liquid in the liquid loop travels sequentially through the pump, the jacket, the VTC, the liquid container, and the heating section.

D74. The system according to any of D1-D73, wherein the delivery tube comprises a jacket in liquid communication with the auxiliary unit and a gas conduit in fluid communication with the VTC.

D75. The system according to D74, wherein the pump is configured to pump the liquid from the heating section to the jacket of the delivery tube.

D76. The system according to D75, wherein the jacket is configured to transmit heat from the liquid in the jacket to the breathing gas in the gas conduit.

D77. The system according to any of D55-D76, wherein a VTC temperature of the VTC is lower than a delivery temperature of the breathing gas in the gas conduit.

D78. The system according to D77, wherein the delivery temperature is greater than a dew point of the breathing gas in the delivery tube.

D79. The system according to any of D74-D48, wherein the delivery tube comprises one or more radial ribs extending through the jacket.

D80. The system according to D79, wherein the one or more radial ribs prevent kinking or blockage of the gas conduit when the delivery tube is bent.

D81. The system according to any of D74-D80, wherein the controller is configured to operate the pump to control a jacket flowrate of liquid in the jacket.

D82. The system according to any of D74-D81, wherein the jacket comprises:
a first section configured to receive the liquid from the auxiliary unit and transmit the liquid towards a distal end of the delivery tube, and
a second section configured to receive the liquid from the first section and transmit the liquid to the auxiliary unit,
wherein the jacket is configured to flow liquid through the first section and through the second section in opposite directions.

D83. The system according to any of D1-D82, wherein the breathing gas outputted by the blower is characterized by a gas velocity configured to prevent liquid buildup in the delivery tube.

D84. The system according to any of D1-D83, further comprising a nasal cannula configured to be coupled to a patient proximate end of the delivery tube, wherein the nasal cannula is configured to direct the breathing gas into at least one nare of the patient.

D85. The system according to any of D1-D84, wherein the auxiliary unit outlet has a bell shape configured to at least one of:
allow bending of the delivery tube at the auxiliary unit outlet,
prevent kinking of the delivery tube at the auxiliary unit outlet, or
prevent dislodging of the delivery tube at the auxiliary unit outlet.

D86. The system according to any of D73-D85, wherein the auxiliary unit comprises a delivery connector configured to connect an exit cap of the VTC to the gas conduit and a pump outlet to the jacket.

D87. The system according to any of D1-D86, wherein the auxiliary unit comprises a housing configured to confine breathing gas and liquid within the auxiliary unit.

D88. The system according to any of D1-D87, wherein the base unit comprises a removable battery and a reserve battery.

D89. The system according to D88, wherein the controller is configured to initiate a low power mode for the system when the removable battery is removed.

D90. The system according to any of D88 and D89, wherein the system is configured to operate without the removable battery.

D91. The system according to any of D88-D90, wherein the reserve battery is configured to provide power to the blower and the controller.

D92. The system according to D91, wherein the reserve battery is configured to provide power for at least about one hour.

D93. The system according to any of D89-D92, wherein the lower power mode allows for operation of one or more alarms and the blower.

D94. The system according to any of D1-D93, wherein the base unit comprises one or more interfaces configured to operatively couple one or more external devices to the controller.

D95. The system according to D94, wherein the one or more external devices include a pulse oximeter configured to output data to the controller.

D96. The system according to D95, wherein the controller is configured for a closed-loop control of patient oxygen based on the pulse oximeter data.

D97. The system according to any of D95 and D96, wherein the controller is configured to adjust the flow rate of supplementary gas through the supplementary gas inlet based on the pulse oximeter data, wherein the supplementary gas comprises oxygen.

D98. The system according to D97, wherein the flow rate of supplementary gas is adjusted to set an oxygen concentration of the breathing gas provided to the patient to a minimum oxygen concentration that is determined to have a therapeutic effect on the patient based on the pulse oximeter data.

D99. The system according to any of D95 and D96, wherein the data from the pulse oximeter includes $SpO_2$ data and alarm condition signals, and wherein the controller is configured to:
receive the pulse oximeter data through a pulse oximeter interface;
from the $SpO_2$ data, determine $PaO_2$ data for calculation of an appropriate oxygen concentration of the breathing gas;
effect adaptive feedback control of the breathing gas based on the $SpO_2$ level signals by a gas interface, wherein the adaptive feedback control is provided by a proportional integral derivative (PID) controller;
receive data via the gas interface including a signal indicating that the breathing gas delivered by the measurement device has been manually changed; and
upon receipt of the signal via the gas interface, enter a manual override mode and halt sending adaptive feedback control signals to the gas interface.

D100. The system according to D99, wherein the controller is configured to compare measured data with alarm limits and to initiate an alarm condition if the measured data is outside the alarm limits.

D101. The system according to any of D99 and D100, wherein the gas interface is operatively coupled to the supplementary valve, and wherein the adaptive feedback control of the breathing gas comprises adjusting the flow rate of supplementary gas through the supplementary gas inlet by actuating the supplementary valve.

D102. The system according to any of D99-D101, wherein the controller comprises a memory configured to store a lookup table, wherein the controller determines the $PaO_2$ data by referencing the lookup table, and wherein the controller is configured to convert a received $SpO_2$ value to a $PaO_2$ value by interpolation upon determining the received $SpO_2$ value is not present in the lookup table.

D103. The system according to D102, wherein the lookup table is derived from a sigmoid shaped oxyhemoglobin dissociation curve.

D104. The system according to any of D95-D103, wherein the pulse oximeter data includes one or more signals indicative of a current blood oxygen level of the patient, and wherein the controller is configured to:
receive via a pulse oximeter interface the one or more signals indicative of the current blood oxygen level;
receive via a gas interface data indicative of the mixture of breathing gas and supplementary gas;
compare the one or more signals indicative of current blood oxygen level to a target blood oxygen level;
calculate an appropriate change to the mixture to achieve a change in a percentage of oxygen in the mixture;
alter the percentage of oxygen in the mixture by actuating the supplementary valve; and
receive new signals from the pulse oximeter interface indicative of a current blood oxygen level of the patient.

D105. The system according to any of D95-D104, wherein the one or more external devices include a transcutaneous carbon dioxide sensor configured to output to the controller at least one patient carbon dioxide measurement.

D106. The system according to D105, wherein the controller is configured for a closed-loop control of patient carbon dioxide based on the at least one patient carbon dioxide measurement.

D107. The system according to any of D95-D106, wherein the one or more external devices includes a pulse oximeter and a transcutaneous carbon dioxide sensor, wherein the pulse oximeter is configured to output oxygen data to the controller, and wherein the transcutaneous carbon dioxide sensor is configured to output carbon dioxide data to the controller.

D108. The system according to D107, wherein the controller is configured to:
receive, via the one or more interfaces, the oxygen data from the pulse oximeter and the carbon dioxide data from the transcutaneous carbon dioxide sensor;
compare the oxygen data and the carbon dioxide data to a reference table which includes at least one reference oxygen value and at least one reference carbon dioxide value; and
determine to provide the patient with high oxygen therapy or high flush therapy.

D109. The system according to D108, wherein the controller is further configured to, upon determining to provide the patient with high oxygen therapy, increase the flow rate of the supplementary gas through the supplementary gas inlet by actuating the supplementary valve.

D110. The system according to D108, wherein the controller is further configured to, upon determining to provide the patient with high flush therapy, increase the breathing gas flowrate of the blower.

D111. The system according to any of D1-D110, wherein the base unit comprises a front computer operatively coupled to the controller and a display operatively coupled to the front computer.

E1. A method of measuring breathing gas flow in a respiratory therapy device, the method comprising:
generating a first measurement of the breathing gas flow using a first flow sensor;
generating a second measurement of the breathing gas flow using a second flow sensor; and
adjusting one or more parameters of the respiratory therapy device based on at least one of the flow measurement or the second measurement.

E2. The method according to E1, wherein the first flow sensor and the second flow sensor are mass flow sensors, and the first measurement and the second measurement indicate mass flow rates of the breathing gas flow.

E3. The method according to any of E1 and E2, wherein adjusting one or more parameters comprises adjusting a gas flow rate of the breathing gas flow based on the second measurement.

E4. The method according to E3, wherein adjusting the gas flow rate comprises controlling a blower configured to output the breathing gas flow.

E5. The method according to any of E1-E4, further comprising calibrating each of the first flow sensor and the second flow sensor relative to the each other.

E6. The method according to any of E1-E5, further comprising mixing the breathing gas flow with supplementary gas flow to form a mixed flow after measuring the first measurement.

E7. The method according to E6, further comprising calculating a flow difference between the first measurement and the second measurement, wherein the second measurement is indicative of the mixed flow.

E8. The method according to E7, further comprising calculating a concentration of one or more components of the mixed flow based on the flow difference and the second measurement.

E9 The method according to E8, further comprising:
receiving as an input a target concentration, and
comparing the concentration to the target concentration.

E10. The method according to E9, wherein adjusting one or more parameters comprises adjusting a flow rate of the supplementary gas flow based on comparing the concentration to the target concentration.

E11. The method according to E10, wherein adjusting the supplementary gas flow rate comprises actuating a solenoid valve.

E12. The method according to any of E7-E11, wherein the flow differences is less than about 1% of the first measurement.

E13. The method according to any of E7-E12, further comprising:
pausing the flow of the supplementary gas; and
calibrating the first flow sensor and the second flow sensor to each other while the supplementary gas flow is paused, wherein calibrating reduces an error of the calculated flow difference to an error of the second flow sensor.

E14. The method according to any of E6-E13, further comprising:
receiving pulse oximeter data from a pulse oximeter; and
adjusting the flow rate of the supplementary gas flow based on the pulse oximeter data, wherein the supplementary gas comprises oxygen.

E15. The method according to E14, further comprising:
  determining a minimum oxygen concentration that has a therapeutic effect on the patient based on the pulse oximeter data; and
  adjusting the flow rate of the supplementary gas flow by setting an oxygen concentration of the breathing gas.
E16. The method according to any of E14 and E15, wherein the data from the pulse oximeter includes $SpO_2$ data and alarm condition signals, and further comprising:
  from the $SpO_2$ data, determining $PaO_2$ data;
  calculating an appropriate oxygen concentration of the breathing gas;
  effecting adaptive feedback control of the breathing gas based on the $SpO_2$ level signals, wherein the adaptive feedback control is provided by a proportional integral derivative (PID) controller;
  receiving a signal indicating that the breathing gas delivered by the measurement device has been manually changed; and
  upon receipt of the signal, entering a manual override mode and halting adaptive feedback control.
E17. The method according to E16, further comprising:
  comparing measured data with alarm limits; and
  initiating an alarm condition if the measured data is outside the alarm limits.
E18. The method according to any of E16 and E17, wherein the adaptive feedback control of the breathing gas comprises adjusting the flow rate of the supplementary gas flow by actuating the supplementary valve.
E19. The method according to any of E16-E18, wherein determining the $PaO_2$ data comprises referencing a lookup table, and further comprising converting a received $SpO_2$ value to a $PaO_2$ value by interpolation upon determining the received $SpO_2$ value is not present in the lookup table.
E20. The method according to E19, wherein the lookup table is derived from a sigmoid shaped oxyhemoglobin dissociation curve.
E21. The method according to any of E6-E20, wherein the pulse oximeter data includes one or more signals indicative of a current blood oxygen level of the patient, and wherein the method further comprises:
  receiving the one or more signals indicative of the current blood oxygen level;
  receiving data indicative of the mixture of breathing gas and supplementary gas;
  comparing the one or more signals indicative of current blood oxygen level to a target blood oxygen level;
  calculating an appropriate change to the mixture to achieve a change in a percentage of oxygen in the mixture;
  altering the percentage of oxygen in the mixture; and
  receiving new signals indicative of a current blood oxygen level of the patient.
E22. The method according to any of E1-E21, further comprising:
  receiving at least one patient carbon dioxide measurement, and
  controlling the breathing gas flow rate based on the at least one patient carbon dioxide measurement.
E23. The method according to any of E6-E22, further comprising:
  receiving oxygen data from a pulse oximeter and carbon dioxide data from a transcutaneous carbon dioxide sensor;
  comparing the oxygen data and the carbon dioxide data to a reference table which includes at least one reference oxygen value and at least one reference carbon dioxide value; and
  determining to provide the patient with high oxygen therapy or high flush therapy.
E24. The method according to E23, further comprising, upon determining to provide the patient with high oxygen therapy, increasing the flow rate of the supplementary gas flow.
E25. The method according to E23, further comprising, upon determining to provide the patient with high flush therapy, increasing the gas flow rate.
E26. The method according to any of E1-E25 using the system according to any of D1-D111.
F1. A method for controlling operation of a respiratory therapy unit, the method comprising:
  receiving a first signal from an alignment sensor in a base unit of the respiratory therapy unit, the first signal being indicative of an alignment the alignment sensor with an alignment marker of an auxiliary unit of the respiratory therapy unit;
  initiating operation of the respiratory therapy unit;
  receiving a second signal from the alignment sensor, the second signal being indicative of a misalignment of the alignment sensor with the alignment marker; and
  halting operation of the respiratory therapy unit.
F2. The method according to F1, further comprising generating an alarm after receiving the second signal.
F3. The method according to any of F1 and F2, wherein the alignment sensor is an RFID reader, and wherein the alignment marker is an RFID tag.
F4. The method according to any of F1 and F2, wherein the alignment sensor is a Hall effect sensor, and wherein the alignment marker is a magnet.
F5 The method according to any of F1-F4 using the system according to any of D1-D111.
G1. A method for controlling operation of a respiratory therapy unit, the method comprising:
  receiving a temperature measurement from a temperature sensor in a heating section of the respiratory therapy unit;
  comparing the temperature measurement to a reference temperature; and
  if the temperature measurement is greater than the reference temperature, halting operation of the respiratory therapy unit.
G2. The method according to G1, further comprising generating an alarm if the temperature measurement is greater than the reference temperature.
G3. The method according to any of G1 and G2 using the system according to any of D1-D111.
H1. A method for controlling power in a respiratory therapy unit, the method comprising:
  receiving a first signal indicating that a removable battery has been removed from the respiratory therapy unit;
  switching operation of the respiratory therapy unit from a regular power mode to a low power mode; and
  operating the respiratory therapy unit using a reserve battery in the respiratory therapy unit.
H2. The method according to H1, further comprising:
  receiving a second signal indicating that the removable battery has been replaced in the respiratory therapy unit;

switching operation of the respiratory therapy unit from the low power mode to the regular power mode; and operating the respiratory therapy unit using the replaced removable battery.

H3. The method according to any of H1 and H2, wherein operating the respiratory therapy unit using the reserve battery lasts at least about one hour.

H4. The method according to any of H1-H3 using the system according to any of D1-D111.

I1. A method for operating a respiratory therapy unit, the method comprising:
receiving at least one liquid level measurement from a level sensor, the at least one liquid level measurement indicating at least one liquid level in a liquid container of the respiratory therapy unit;
receiving at least one flow measurement from a flow sensor, the at least one flow measurement indicating a flow rate of breathing gas in the respiratory therapy unit; and
calculating a humidity of the breathing gas based on at least the at least one liquid level measurement and the at least one flow measurement.

I2. The method according to I1, further comprising actuating a valve based on the humidity, wherein the valve controls the flow rate of the breathing gas.

I3. The method according to any of I1 and I2, further comprising:
comparing calculated humidity to a reference humidity; and
generating an alarm if the calculated humidity is below the reference humidity.

I4. The method according to any of I1-I3, further comprising:
comparing the at least one liquid level measurement to a reference liquid level;
generating an alarm; and
halting operation of the respiratory therapy unit.

I5. The method according to any of I1-I4, wherein the level sensor is a capacitive sensor.

I6. The method according to any of I1-I5 using the system according to any of D1-D111.

J1. A method for providing respiratory therapy to a patient using the system according to any of D1-D111, the method comprising:
outputting a flow of breathing gas from the blower through the delivery tube and into a nasal cannula; and
providing the breathing gas to a nare of the patient from at least one nasal prong of the nasal cannula, the nasal cannula being in fluid communication with the conduit and configured to receive the breathing gas from the delivery tube;
wherein the at least one nasal prong is configured to provide breathing gas from a distal end of the at least one nasal prong at an exit velocity of at least about 40 m/s and less than about 75 m/s.

J2. The method according to J1, wherein the at least one nasal prong has an inner diameter greater than or equal to about 1.4 mm and less than about 1.8 mm, and the blower has a maximum flow setpoint greater than or equal to about 9 L/min and less than about 28 L/min.

J3. The method according to J1, wherein the at least one nasal prong has an inner diameter greater than or equal to about 1.8 mm and less than about 1.9 mm, and the blower has a maximum flow setpoint greater than or equal to about 13 L/min and less than about 31 L/min.

J4. The method according to J1, wherein the at least one nasal prong has an inner diameter greater than or equal to about 1.9 mm and less than about 3 mm, and the blower has a maximum flow setpoint greater than or equal to about 21 L/min and less than about 60 L/min.

J5. The method according to J1, wherein the at least one nasal prong has an inner diameter greater than or equal to about 3 mm and less than about 4 mm, and the blower has a maximum flow setpoint greater than or equal to about 34 L/min and less than about 80 L/min.

J6. The method according to J1, wherein the at least one nasal prong has an inner diameter greater than or equal to about 1.1 mm and less than about 1.6 mm, and the nasal cannula has a pressure drop less than about 80 hPa when the blower operates at a maximum flow setpoint of about 8 L/min.

J7. The method according to J1, wherein the at least one nasal prong has an inner diameter greater than or equal to about 1.5 mm and less than about 2 mm, and the nasal cannula has a pressure drop less than about 100 hPa when the blower operates at a maximum flow setpoint of about 20 L/min.

J8. The method according to J1, wherein the at least one nasal prong has an inner diameter greater than or equal to about 1.9 mm and less than about 3.5 mm, and the nasal cannula has a pressure drop less than about 80 hPa when the blower operates at a maximum flow setpoint of about 40 L/min.

J9. The method according to any of J1-J8, further comprising:
receiving first data indicative of one or more dimensions of the nasal cannula;
receiving second data indicative of a flowrate of breathing gas; and
calculating the exit velocity based on the first data and the second data.

J10. The method according to J9, further comprising:
generating for display at least one selected from the group of: the flowrate, the exit velocity, a maximum flow setpoint, and a pressure drop.

J11. The method according to any of J9 and J10, comprising generating for display the flowrate and the exit velocity.

J12. The method according to any of J9-J11, further comprising:
receiving a user input to increase or decrease the flowrate of the breathing gas;
changing the flowrate to a modified flowrate of the breathing gas;
calculating a modified velocity based on the modified flowrate and the first data; and
generating for display at least one selected from the group of: the modified flowrate and the modified velocity.

J13. The method according to any of J1-J12, wherein the exit velocity is at least about 40 m/s and less than about 70 m/s.

J14. The method according to any of J1-J13, wherein the exit velocity is at least about 40 m/s and less than about 65 m/s.

J15. The method according to any of J1-J14, wherein the exit velocity is at least about 40 m/s and less than about 60 m/s.

J16. The method according to any of J1-J15, wherein the exit velocity is at least about 40 m/s and less than about 55 m/s.

J17. The method according to any of J1-J16, wherein the exit velocity is at least about 40 m/s and less than about 50 m/s.

J18. The method according to any of J1-J17, wherein the exit velocity is at least about 40 m/s and less than about 45 m/s.

J19. The method according to any of J1-J18, wherein the exit velocity is about 40 m/s.

K1. A respiratory therapy unit comprising:
a blower configured to output breathing gas;
a controller;
a removable battery; and
a reserve battery.

K2. The respiratory therapy unit according to K1, wherein the controller is configured to initiate a low power mode for the system when the removable battery is removed.

K3. The respiratory therapy unit according to any of K1 and K2, wherein the system is configured to operate without the removable battery.

K4. The respiratory therapy unit according to any of K1-K3, wherein the reserve battery is configured to provide power to the blower and the controller.

K5. The respiratory therapy unit according to K4, wherein the reserve battery is configured to provide power for at least about one hour.

K6. The respiratory therapy unit according to K2, wherein the low power mode allows for operation of one or more alarms and the blower.

L1. A measurement device for a respiratory therapy unit, the measurement device comprising:
a first flow sensor,
a second flow sensor, and
a conduit in fluid communication with the respiratory therapy unit,
wherein the first flow sensor and second flow sensor are positioned in series along the conduit.

L2. The measurement device according to L1, wherein the conduit is configured to:
receive breathing gas from an inlet of the respiratory therapy unit;
direct the breathing gas through the first flow sensor, wherein the first flow sensor is configured to output a first measurement of the breathing gas;
direct the breathing gas through the second flow sensor, wherein the second flow sensor is configured to output a second measurement of the breathing gas; and
output the breathing gas to the respiratory therapy unit.

L3. The measurement device according to L2, further comprising a controller operatively coupled to the respiratory therapy unit, and wherein the controller is configured to set a breathing gas flowrate of the respiratory therapy unit based on at least one of the first measurement or the second measurement.

L4. The measurement device according to any of L2 and L3, wherein the first flow sensor and the second flow sensor are mass flow sensors.

L5. The measurement device according to any of L2-L4, wherein the controller is configured to calibrate each of the first flow sensor and the second flow sensor are relative to the other.

L6. The measurement device according to any of L1-L5, wherein the conduit comprises a first segment configured to direct the breathing gas through the first flow sensor and a second segment configured to direct the breathing gas through the second flow sensor, wherein the first segment and the second segment are approximately straight.

L7. The measurement device according to any of L1-L6, further comprising a supplementary gas inlet configured to receive a supplementary gas from an external gas source and add the supplementary gas to the breathing gas, wherein the supplementary gas inlet is disposed between the first flow sensor and the second flow sensor.

L8. The measurement device according to L7, further comprising an inlet valve configured to control a flow rate of the supplementary gas through the supplementary gas inlet.

L9. The measurement device according to L8, wherein the inlet valve is a solenoid valve.

L10. The measurement device according to any of L8 and L9, wherein the first flow sensor is configured to output a first measurement of the breathing gas, and wherein the second flow sensor is configured to output a second measurement of a mixture of the breathing gas and the supplementary gas.

L11. The measurement device according to L10, wherein the controller is configured to calculate a flow difference between the first measurement and the second measurement, wherein the flow difference indicates an amount of one or more components of the supplementary gas added to the breathing gas, and wherein the controller is configured to calculate one or more concentrations of the one or more components in the mixture based on the flow difference and the second measurement.

L12. The measurement device according to L11, wherein the controller is configured to operate the inlet valve to control the added amount based on the calculated flow difference.

L13. The measurement device according to L12, wherein the controller is configured to:
receive as an input a target concentration,
compare the one or more calculated concentrations to the target concentration, and control the added amount based on the comparison.

L14. The measurement device according to any of L11-L13, wherein the flow difference is less than about 5% of the first measurement.

L15. The measurement device according to L14, wherein the flow difference is less than about 1% of the first measurement.

L16. The measurement device according to any of L7-L15, wherein the external gas source is one selected from the group of: a wall gas outlet, a gas concentrator, and a gas tank.

L17. The measurement device according to any of L7-L16, wherein the supplementary gas is oxygen, oxygen concentrated breathing gas, helium, nitric oxide, heliox, an anesthetic gas, or a gas containing aerosolized medicament.

L18. The measurement device according to any of L11-L17, wherein the controller is configured to operate the inlet valve to pause the flow of the supplementary gas and to calibrate the first flow sensor and the second flow sensor to each other while the supplementary gas flow is paused, wherein calibrating reduces an error of the calculated flow difference to an error of the second flow sensor.

L19. The measurement device according to any of L7-L18, further comprising:
   one or more additional supplementary gas inlets for adding one or more additional supplementary gas; and
   one or more additional flow sensors, wherein the device comprises one additional flow sensor for each additional supplementary gas inlet.

L20. The measurement device according to any of L7-L19, wherein the supplementary gas comprises oxygen, and wherein the controller is configured to adjust the flow rate of supplementary gas through the supplementary gas inlet based on pulse oximeter data received from a pulse oximeter.

L21. The measurement device according to L20, wherein the flow rate of supplementary gas is adjusted to set an oxygen concentration of the breathing gas provided to the patient to a minimum oxygen concentration that is determined to have a therapeutic effect on the patient based on the pulse oximeter data.

L22. The measurement device according to any of L20 and L21, wherein the data from the pulse oximeter includes $SpO_2$ data and alarm condition signals, and wherein the controller is configured to:
   receive the pulse oximeter data;
   from the $SpO_2$ data, determine $PaO_2$ data for calculation of an appropriate oxygen concentration of the breathing gas;
   effect adaptive feedback control of the breathing gas based on the $SpO_2$ level signals by a device interface, wherein the adaptive feedback control is provided by a proportional integral derivative (PID) controller;
   receive data via the device interface including a signal indicating that the breathing gas delivered by the measurement device has been manually changed; and
   upon receipt of the signal via the device interface, enter a manual override mode and halt sending adaptive feedback control signals to the device interface.

L23. The measurement device according to L22, wherein the controller is configured to compare measured data with alarm limits and to initiate an alarm condition if the measured data is outside the alarm limits.

L24. The measurement device according to any of L22 and L23, wherein the device interface is operatively coupled to the supplementary valve, and wherein the adaptive feedback control of the breathing gas comprises adjusting the flow rate of supplementary gas through the supplementary gas inlet by actuating the supplementary valve.

L25. The measurement device according to any of L22-L24, wherein the controller comprises a memory configured to store a lookup table, wherein the controller determines the $PaO_2$ data by referencing the lookup table, and wherein the controller is configured to convert a received $SpO_2$ value to a $PaO_2$ value by interpolation upon determining the received $SpO_2$ value is not present in the lookup table.

L26. The measurement device according to L25, wherein the lookup table is derived from a sigmoid shaped oxyhemoglobin dissociation curve.

L27. The measurement device according to any of L20-L26, wherein the pulse oximeter data includes one or more signals indicative of a current blood oxygen level of the patient, and wherein the controller is configured to:
   receive via a pulse oximeter interface the one or more signals indicative of the current blood oxygen level;
   receive via a device interface data indicative of the mixture of breathing gas and supplementary gas;
   compare the one or more signals indicative of current blood oxygen level to a target blood oxygen level;
   calculate an appropriate change to the mixture to achieve a change in a percentage of oxygen in the mixture;
   alter the percentage of oxygen in the mixture by actuating the supplementary valve; and receive new signals from the pulse oximeter interface indicative of a current blood oxygen level of the patient.

L28. The measurement device according to any of L7-L27, wherein the controller is configured to:
   receive, via the one or more interfaces, oxygen data from a pulse oximeter and carbon dioxide data from a transcutaneous carbon dioxide sensor;
   compare the oxygen data and the carbon dioxide data to a reference table which includes at least one reference oxygen value and at least one reference carbon dioxide value; and
   determine to provide the patient with high oxygen therapy or high flush therapy.

L29. The measurement device according to L28, wherein the controller is further configured to, upon determining to provide the patient with high oxygen therapy, increase the flow rate of the supplementary gas through the supplementary gas inlet by actuating the supplementary valve.

L30. The measurement device according to L28, wherein the controller is further configured to, upon determining to provide the patient with high flush therapy, increase the breathing gas flowrate of the blower.

M1. A respiratory therapy system comprising:
   an auxiliary unit having a heating section and a heating plate disposed in the heating section; and
   a base unit having a heat actuator configured to be operatively coupled to the heating plate and is not in contact with the heating plate.

M2. The respiratory therapy system according to M1, wherein the heat actuator is a coil that is configured to induce a current in the heating plate.

M3. The respiratory therapy system according to M2, wherein the induced current generates heat in the heating plate due to a resistance of the heating plate.

M4. The respiratory therapy system according to any of M1-M3, wherein the heating plate is configured to be immersed in a liquid within the auxiliary unit and to heat the liquid.

M5. The respiratory therapy system according to any of M1-M4, wherein the heating plate does not contact an external surface of the auxiliary unit.

M6. The respiratory therapy system according to any of M1-M5, wherein the heating plate comprises a protruding tab, and wherein the base unit comprises a temperature sensor configured to output a temperature measurement of the protruding tab.

M7. The respiratory therapy system according to M6, further comprising a controller configured to receive the temperature measurement and compare the temperature measurement to a reference temperature.

M8. The respiratory therapy system according to M7, wherein, based on comparing the temperature measurement to the reference temperature, the controller is configured to at least one of halt operation of the respiratory therapy system or generate an alarm.

M9. The respiratory therapy system according to any of M1-M8, wherein the heat actuator is configured to operate while the respiratory therapy unit operates without an external power supply.

M10. The respiratory therapy system according to any of M1-M9, wherein the heating plate is orientation specific relative to the heat actuator.

N1. A respiratory therapy system comprising:
a base unit configured to output breathing gas; and
an auxiliary unit configured to receive the outputted breathing gas, the auxiliary unit comprising:
a liquid container; and
a vapor transfer cartridge (VTC) configured to humidify the breathing gas;
wherein the liquid container comprises an outlet conduit in fluid communication with a cartridge inlet of the VTC.

N2. The respiratory therapy system according to N1, wherein the base unit comprises a level sensor configured to output at least one liquid level measurement indicating a liquid level in the liquid container.

N3. The respiratory therapy system according to N2, further comprising a controller, wherein the controller is configured to:
receive the at least one liquid level measurement from the level sensor;
calculate an output humidity of the VTC based on at least in part the at least one liquid level measurement.

N4. The respiratory therapy system according to N3, further comprising a gas valve configured to actuate a gas flow rate of the outputted breathing gas from the base unit to the auxiliary unit, wherein the controller is configured to control the gas valve based on the output humidity.

N5. The respiratory therapy system according to any of N2-N4, wherein the controller is configured to compare the at least one liquid level measurement to a reference liquid level and at least one of generate an alarm or halt operation of the system.

N6. The respiratory therapy system according to any of N2-N5, wherein the level sensor is a capacitive sensor.

O1. The method according to any of B1-B12 and C1-C8, wherein the respiratory therapy is used for treatment of coronavirus disease 2019 (COVID-19).

O2. The method according to O1, wherein the breathing gas comprises supplementary oxygen.

O3. The method according to any of O1 and O2, wherein the nasal cannula is surrounded by a mask configured to minimize spread of aerosols from exhaled air.

P1. The system, device, or method according to any of A1-A19, B1-B12, C1-C8, D1-D111, E1-E26, F1-F5, G1-G3, H1-H4, I1-I6, J1-J19, K1-K6, L1-L30, M1-M10, N1-N6, and O1-O3, wherein a nebulizer is configured to introduce aerosolized medicament into the breathing gas via an adaptor or port.

P2. The system, device, or method according to P1, wherein the nebulizer is configured to connect to one of: the delivery tube, the nasal cannula, or the auxiliary unit.

Q1. The system, device, or method according to any of A1-A19, B1-B12, C1-C8, D1-D111, E1-E26, F1-F5, G1-G3, H1-H4, I1-I6, J1-J19, K1-K6, L1-L30, M1-M10, N1-N6, O1-O3, and P1-P2, wherein respiratory therapy is provided via a mobile platform.

Q2. The system, device, or method according to Q1, wherein the mobile platform is a rolling cart or a vehicle.

Q3. The system, device, or method according to any of Q1 and Q2, wherein the mobile platform allows for continuous operation of the system during transportation.

Q4. The system, device, or method according to any of Q1-Q3, wherein respiratory therapy is provided in a patient's home or in an ambulance.

Q5. The system, device, or method according to any of Q1-Q4, wherein the blower intakes ambient air and operates using power from an internal battery.

R1. The system, device, or method according to any of A1-A19, B1-B12, C1-C8, D1-D111, E1-E26, F1-F5, G1-G3, H1-H4, I1-I6, J1-J19, K1-K6, L1-L30, M1-M10, N1-N6, O1-O3, P1-P2, and Q1-Q5, wherein the base unit is a first base unit, and wherein the auxiliary unit is configured to be removed from the first base unit and transferred to a second base unit.

R2. The system, device, or method according to R1, wherein a tag in the auxiliary unit is configured to store data indicative of a therapy provided to the patient using the first base unit.

R3. The system, device, or method according to R2, wherein the tag is configured to store the data prior to or during removal of the auxiliary unit from the first base unit.

R4. The system, device, or method according to any of R2 and R3, wherein the tag is configured to transmit the data to a controller of the second base unit.

R5. The system, device, or method according to any of R2-R4, wherein the second base unit is configured to resume the therapy provided to the base unit when the auxiliary unit is transferred.

R6. The system, device, or method according to any of R2-R5, wherein the data is indicative of at least one of: that the auxiliary unit was providing therapy, a time at which therapy is stopped, a breathing gas flowrate, a breathing gas temperature, a breathing gas oxygen concentration, a breathing gas humidity, an actual temperature relative to a setpoint temperature, a patient age, a patient height, a patient weight, a patient disease, a disease status, and one or more concomitant therapies.

We claim:

1. A system for providing respiratory therapy to a patient, the system comprising:
an attachable auxiliary unit;
a base unit comprising a recess sized and shaped to receive the attachable auxiliary unit, the base unit comprising an inner wall, the inner wall comprising a first surface that partly defines the recess and a second surface that is opposite from the first surface, the second surface partly defining an interior space of the base unit;
a low-pressure blower having an operational gauge pressure limit of less than 270 hPa, the blower configured to:
receive breathing gas from ambient air, a tank, or a wall outlet; and
output pressurized breathing gas at a pressure up to the operational gauge pressure limit;
a humidifier in fluid communication with the low-pressure blower, wherein the humidifier receives the pressurized breathing gas from the low-pressure blower and humidifies the breathing gas, wherein the humidifier further comprises:

an internal reservoir in the attachable auxiliary unit configured to contain a volume of a liquid;

a non-contact heat actuator of the base unit configured to heat the liquid in the internal reservoir when the attachable auxiliary unit is seated within the recess of the base unit, the heat actuator comprising a magnetic coil configured to heat, via induction, a plate disposed in the internal reservoir, wherein the heat is generated in the plate by the non-contact heat actuator by inducing eddy currents in the plate, the non-contact heat actuator positioned in the interior space and adjacent to the second surface; and a level sensor of the base unit configured to measure a level of the liquid in the internal reservoir, the level sensor disposed in the interior space of the base unit alongside the internal reservoir and comprising a capacitive sensing circuit configured to measure change in capacitance of the liquid as the level of liquid changes when the attachable auxiliary unit is seated within the recess of the base unit;

a conduit in fluid communication with the humidifier and configured to receive heated and humidified breathing gas from the humidifier;

a non-sealing nasal cannula having at least one nasal prong, the nasal cannula being in fluid communication with the conduit and configured to receive the heated and humidified breathing gas from the conduit, the at least one nasal prong having a distal opening and being configured to provide the heated and humidified breathing gas through the distal opening to a nare of the patient;

wherein the at least one nasal prong is configured such that heated and humidified breathing gas exits the distal opening at an exit velocity of at least 40 m/s and less than 75 m/s and at a flowrate of at least 8 L/min and less than 80 L/min; and a controller and a processor configured to:
receive first data indicative of one or more dimensions of the nasal cannula;
receive second data indicative of a flowrate of breathing gas; and
calculate the exit velocity based on the first data and the second data.

2. The system of claim 1, wherein the at least one nasal prong has an inner diameter greater than or equal to 1.4 mm and less than 1.8 mm, and the system has a maximum flow setpoint greater than or equal to 9 L/min and less than 28 L/min.

3. The system of claim 1, wherein the at least one nasal prong has an inner diameter greater than or equal to 1.8 mm and less than 1.9 mm, and the system has a maximum flow setpoint greater than or equal to 13 L/min and less than 31 L/min.

4. The system of claim 1, wherein the at least one nasal prong has an inner diameter greater than or equal to 1.9 mm and less than 3 mm, and the system has a maximum flow setpoint greater than or equal to 21 L/min and less than 60 L/min.

5. The system of claim 1, wherein the at least one nasal prong has an inner diameter greater than or equal to 3 mm and less than 4 mm, and the system has a maximum flow setpoint greater than or equal to 34 L/min and less than 80 L/min.

6. The system of claim 1, wherein the at least one nasal prong has an inner diameter greater than or equal to 1.1 mm and less than 1.6 mm, and the nasal cannula has a pressure drop less than 80 hPa when operating at a maximum flow setpoint of about 8 L/min.

7. The system of claim 1, wherein the at least one nasal prong has an inner diameter greater than or equal to 1.5 mm and less than 2 mm, and the nasal cannula has a pressure drop less than 100 hPa when operating at a maximum flow setpoint of about 20 L/min.

8. The system of claim 1, wherein the at least one nasal prong has an inner diameter greater than or equal to 1.9 mm and less than 3.5 mm, and the nasal cannula has a pressure drop less than 80 hPa when operating at a maximum flow setpoint of about 40 L/min.

9. The system of claim 1, further comprising a display, and wherein the processor is further configured to generate for display at least one of: the flowrate, the exit velocity, a maximum flow setpoint, and a pressure drop.

10. The system of claim 1, wherein the processor receives the first data from an RFID tag within the attachable auxiliary unit and the second data from a sensor within the base unit.

11. The system of claim 1, wherein the first data comprises an inner diameter of the at least one nasal prong.

12. The system of claim 1, wherein the processor is further configured to receive a user input to change at least one of: the flowrate of breathing gas to a modified flowrate of breathing gas or the exit velocity to a modified velocity.

13. The system of claim 12, wherein the controller is configured to change the flowrate of breathing gas to the modified flowrate based on the user input.

14. The system of claim 1, wherein the humidifier is one of a vapor transfer cartridge or a hot pot humidifier.

15. The system of claim 1, wherein the exit velocity is at least 40 m/s and less than 70 m/s.

16. The system of claim 1, wherein the exit velocity is at least 40 m/s and less than 60 m/s.

17. The system of claim 1, wherein the exit velocity is at least 40 m/s and less than about 50 m/s.

18. The system of claim 1, wherein the exit velocity is about 40 m/s.

19. The system of claim 1, wherein the controller and the processor are configured to:
receive, from the level sensor of the base unit, signals indicating the changes in the liquid level;
compute, based on the signals, a vaporization rate of the liquid; and
compute, based on the vaporization rate, humidity of the breathing gas exiting the humidifier.

20. The system of claim 19, wherein the controller is further configured to adjust the flowrate of the breathing gas or a flowrate of the liquid based on the computed humidity.

21. A method for providing respiratory therapy to a patient by a high velocity respiratory therapy system, the method comprising:
receiving a flow of breathing gas from a low-pressure blower into a humidifier, wherein the low-pressure blower has an operational gauge pressure limit of less than 270 hPa, and wherein the humidifier further comprises:
an internal reservoir in an attachable auxiliary unit configured to contain a volume of a liquid;
heating the liquid in the internal reservoir using a non-contact heat actuator of a base unit, wherein the base unit comprises a recess sized and shaped to receive the attachable auxiliary unit, the base unit comprising an inner wall, the inner wall comprising a first surface that partly defines the recess and a second surface that is opposite from the first surface, the second surface partly defining an interior space of the base unit, the non-contact heat actuator of the base unit positioned in the interior space, adjacent to the second surface, the non-contact heat actuator comprising a magnetic coil, by heating, via induction, a plate disposed in the internal reservoir, wherein the heat is generated in the plate by the non-contact heat actuator when the attachable auxiliary unit is seated within the recess of the base unit by inducing eddy currents in the plate;

measuring a level of the liquid in the internal reservoir using a level sensor of the base unit disposed in the interior space of the base unit, alongside the internal reservoir and comprising a capacitive sensing circuit measuring change in capacitance of the liquid as the level of the liquid changes when the attachable auxiliary unit is seated within the recess of the base unit;

outputting heated and humidified breathing gas from the humidifier through a conduit and into a non-sealing nasal cannula at a pressure up to the operational gauge pressure limit;

providing the heated and humidified breathing gas to a nare of the patient through a distal opening of at least one nasal prong of the nasal cannula, the nasal cannula being in fluid communication with the conduit and configured to receive the heated and humidified breathing gas from the conduit;

wherein the at least one nasal prong is configured such that heated and humidified breathing gas exits from the distal opening of the at least one nasal prong at an exit velocity of at least 40 m/s and less than 75 m/s and at a flowrate of at least 8 L/min and less than 80 L/min; and receiving, at a controller, first data indicative of one or more dimensions of the nasal cannula;

receiving, at the controller, second data indicative of a flowrate of breathing gas; and calculating, by a processor, the exit velocity based on the first data and the second data.

22. The method of claim 21, wherein the at least one nasal prong has an inner diameter greater than or equal to 1.4 mm and less than 1.8 mm, and the low-pressure blower has a maximum flow setpoint greater than or equal to 9 L/min and less than 28 L/min.

23. The method of claim 21, wherein the at least one nasal prong has an inner diameter greater than or equal to 1.8 mm and less than 1.9 mm, and the low-pressure blower has a maximum flow setpoint greater than or equal to 13 L/min and less than 31 L/min.

24. The method of claim 21, wherein the at least one nasal prong has an inner diameter greater than or equal to 1.9 mm and less than 3 mm, and the low-pressure blower has a maximum flow setpoint greater than or equal to 21 L/min and less than 60 L/min.

25. The method of claim 21, wherein the at least one nasal prong has an inner diameter greater than or equal to 3 mm and less than 4 mm, and the low-pressure blower has a maximum flow setpoint greater than or equal to 34 L/min and less than 80 L/min.

26. The method of claim 21, wherein the at least one nasal prong has an inner diameter greater than or equal to 1.1 mm and less than 1.6 mm, and the nasal cannula has a pressure drop less than 80 hPa when the low-pressure blower operates at a maximum flow setpoint of about 8 L/min.

27. The method of claim 21, wherein the at least one nasal prong has an inner diameter greater than or equal to 1.5 mm and less than 2 mm, and the nasal cannula has a pressure drop less than 100 hPa when the low-pressure blower operates at a maximum flow setpoint of about 20 L/min.

28. The method of claim 21, wherein the at least one nasal prong has an inner diameter greater than or equal to 1.9 mm and less than 3.5 mm, and the nasal cannula has a pressure drop less than 80 hPa when the low-pressure blower operates at a maximum flow setpoint of about 40 L/min.

29. The method of claim 21, further comprising:
generating for display at least one selected from the group of: the flowrate, the exit velocity, a maximum flow setpoint, and a pressure drop.

30. The method of claim 21, further comprising:
receiving a user input to increase or decrease the flowrate of the breathing gas;
changing the flowrate to a modified flowrate of the breathing gas;
calculating a modified velocity based on the modified flowrate and the first data; and
generating for display at least one selected from the group of: the modified flowrate and the modified velocity.

31. The method of claim 21, further comprising:
receiving at the controller, from the level sensor of the base unit, signals indicating the changes in the liquid level;
computing, by the processor, based on the signals, a vaporization rate of the liquid; and
computing, by the processor, based on the vaporization rate, humidity of the breathing gas exiting the humidifier.

32. The method of claim 31, further comprising adjusting, by the controller, the flowrate of the breathing gas or a flowrate of the liquid based on the computed humidity.

33. A system for providing respiratory therapy to a patient, the system comprising:
an attachable auxiliary unit:
a base unit comprising a recess sized and shaped to receive the attachable auxiliary unit, the base unit comprising an inner wall, the inner wall comprising a first surface that partly defines the recess and a second surface that is opposite from the first surface, the second surface partly defining an interior space of the base unit;
a low-pressure blower having an operational gauge pressure limit of less than 270 hPa, the blower configured to:
receive breathing gas from ambient air, a tank, or a wall outlet; and
output pressurized breathing gas at a pressure up to the operational gauge pressure limit;
a humidifier in fluid communication with the low-pressure blower, wherein the humidifier receives the pressurized breathing gas from the low-pressure blower and humidifies the breathing gas, wherein the humidifier further comprises:
an internal reservoir in the attachable auxiliary unit configured to contain a volume of a liquid;
a non-contact heat of the base unit actuator configured to heat the liquid in the internal reservoir when the attachable auxiliary unit is seated within the recess of the base unit, the heat actuator comprising a magnetic coil configured to heat, via induction, a plate disposed in the internal reservoir, wherein the heat is generated in the plate by the non-contact heat actuator by inducing eddy currents in the plate, the non-contact heat actuator positioned in the interior space and adjacent to the second surface; and a level sensor of the base unit configured to measure a level of the liquid in the internal reservoir, the level sensor disposed in the interior space of the base unit alongside the internal reservoir and comprising a capacitive sensing circuit configured to measure change in capacitance of the liquid as the level of the liquid changes when the attachable auxiliary unit is seated within the recess of the base unit;

a conduit in fluid communication with the humidifier and configured to receive heated and humidified breathing gas from the humidifier;

a non-sealing nasal cannula having at least one nasal prong, the nasal cannula being in fluid communication with the conduit and configured to receive the heated and humidified breathing gas from the conduit, the at least one nasal prong having a distal opening and being configured to provide the heated and humidified breathing gas through the distal opening to a nare of the patient;

wherein the at least one nasal prong is configured such that heated and humidified breathing gas exits the distal opening at an exit velocity of at least 40 m/s and less than 75 m/s and at a flowrate of at least 8 L/min and less than 80 L/min; and a controller and a processor configured to:

receive first data indicative of one or more dimensions of the nasal cannula;

receive second data indicative of a flowrate of breathing gas;

calculate the exit velocity based on the first data and the second data; and receive a user input to change the exit velocity to a modified velocity.

* * * * *